(12) United States Patent
Ma et al.

(10) Patent No.: US 9,761,807 B2
(45) Date of Patent: Sep. 12, 2017

(54) ORGANIC LIGHT EMITTING DIODE MATERIALS

(71) Applicant: Universal Display Corporation, Ewing, NJ (US)

(72) Inventors: Bin Ma, Plainsboro, NJ (US); Walter Yeager, Yardley, PA (US); Edward Barron, Hamilton, NJ (US); Kwang-Ohk Cheon, Holland, PA (US); Lichang Zeng, Lawrenceville, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 482 days.

(21) Appl. No.: 14/174,396

(22) Filed: Feb. 6, 2014

(65) Prior Publication Data
US 2015/0014649 A1 Jan. 15, 2015

Related U.S. Application Data

(60) Provisional application No. 61/846,100, filed on Jul. 15, 2013.

(51) Int. Cl.
*H01L 51/50* (2006.01)
*H01L 51/00* (2006.01)
*C07D 405/10* (2006.01)
*C07D 409/04* (2006.01)
*C07D 409/10* (2006.01)
*C07D 409/14* (2006.01)

(52) U.S. Cl.
CPC ........ *H01L 51/0054* (2013.01); *C07D 405/10* (2013.01); *C07D 409/04* (2013.01); *C07D 409/10* (2013.01); *C07D 409/14* (2013.01); *H01L 51/0072* (2013.01); *H01L 51/0073* (2013.01); *H01L 51/0074* (2013.01); *H01L 51/0081* (2013.01); *H01L 51/0085* (2013.01); *H01L 51/5016* (2013.01)

(58) Field of Classification Search
None
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1725079 11/2006
(Continued)

OTHER PUBLICATIONS

Extended European Search Report dated Nov. 6, 2014 for corresponding EP Application No. 14176384.7.
(Continued)

*Primary Examiner* — Gregory Clark
(74) *Attorney, Agent, or Firm* — Duane Morris LLP

(57) ABSTRACT

The present invention relates to novel organic compounds containing a triphenylene and a carbazole. The compounds are useful for organic light-emitting diodes. The compounds are also useful for charge-transport and charge-blocking layers, and as hosts in the light-emissive layer for organic light emitting devices (OLEDs).

18 Claims, 3 Drawing Sheets

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0237334 A1 | 9/2010 | Ma et al. |
| 2013/0049576 A1* | 2/2013 | Katakura ............... C09K 11/06 313/504 |
| 2013/0060037 A1 | 3/2013 | Lin et al. |
| 2013/0087776 A1 | 4/2013 | Lee et al. |
| 2013/0112952 A1* | 5/2013 | Adamovich ........ H01L 51/0054 257/40 |
| 2013/0207092 A1 | 8/2013 | Huh et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 0215654 | 2/2002 |
| WO | 0340257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | WO 2011/136755 * | 3/2011 ............. H01I 50/00 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Left., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

(56) References Cited

OTHER PUBLICATIONS

Gao, Zhicliang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4",4"-Tris(3-methylphenylphenyl-amino) triphenylamine (m-MTDATA), as Hole-Transport Materials," Adv. Mater., 6(9) 677-679 (1994).
Kwong, Raymond C. et al., "High Operational Stability of Electrophosphorescent Devices," Appl. Phys. Left., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10)1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes containing N^C^N Nacan-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. And VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula IV

ORGANIC LIGHT EMITTING DIODE MATERIALS

This application claims priority to U.S. Provisional Application No. 61/846,100, filed Jul. 15, 2013, which is incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic compounds comprising a triphenylene and a carbazole. The compounds are useful as host materials for organic light-emitting diodes. The compounds are also useful for charge-transport and charge-blocking layers, and as hosts in the light-emissive layer for organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices, organic phototransistors, organic photovoltaic cells, and organic photodetectors. For OLEDs, the organic materials may have performance advantages over conventional materials.

For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

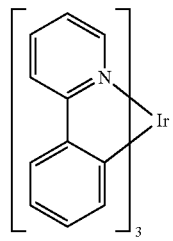

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

BRIEF SUMMARY OF THE INVENTION

A new class of compounds containing a triphenylene and a carbazole is provided.

The present invention provides a compound having formula I:

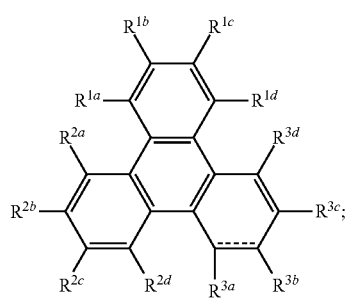

(I)

wherein at least one of $R^{3a}$, $R^{3b}$, $R^{3c}$, or $R^{3d}$ has formula II:

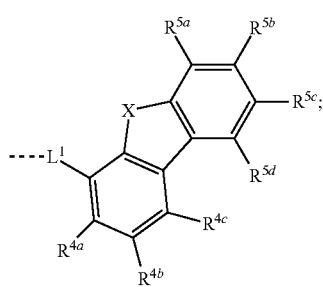

(II)

wherein at least one of $R^{4a}$, $R^{4b}$, $R^{4c}$, $R^{5a}$, $R^{5b}$, $R^{5c}$, or $R^{5d}$ has formula III:

-L²-G (III);

wherein $L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof;

wherein X is selected from the group consisting of O, S, and Se;

wherein G is a carbazole which may be optionally substituted;

wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, G is connected to $L^2$ at the nitrogen atom of the 9-position of carbazole.

In some embodiments, G is connected to $L^2$ at a carbon atom at the 1-, 2-, 3-, or 4-position of carbazole.

In some embodiments, $L^1$ is a direct bond.

In some embodiments, one of $R^{4b}$, $R^{5a}$, or $R^{5c}$ is $L^2$-G.

In some embodiments, $L^1$ and $L^2$ are independently selected from the group consisting of a direct bond, a phenyl group, and a biphenyl group.

In some embodiments, $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, aryl, heteroaryl, and combinations thereof, $R^{3a}$, $R^{3b}$, $R^{3c}$, and $R^{3d}$ that are not formula II are each independently selected from the group consisting of hydrogen, deuterium, aryl, heteroaryl, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, aryl, heteroaryl, and combinations thereof.

In some embodiments, $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, $R^{3a}$, $R^{3b}$, $R^{3c}$, and $R^{3d}$ that are not formula II are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof.

In some embodiments, $R^{1a}$, $R^{1b}$, $R^{1c}$, $R^{1d}$, $R^{2a}$, $R^{2b}$, $R^{2c}$, and $R^{2d}$ are hydrogen, $R^{3a}$, $R^{3b}$, $R^{3c}$, and $R^{3d}$ that are not formula II are hydrogen, and $R^{4a}$, $R^{4b}$, $R^{4c}$, $R^{5a}$, $R^{5b}$, $R^{5c}$, and $R^{5d}$ that are not formula III are hydrogen.

In some embodiments, X is O.

In some embodiments, X is S.

In some embodiments, X is S, $L^1$ and $L^2$ are a direct bond, and $R^{5a}$ is $L^2$-G.

In some embodiments, X is S, $L^1$ is a direct bond, $L^2$ is phenyl, and $R^{5a}$ is $L^2$-G.

In some embodiments, G is substituted with one or more substituents selected from the group consisting of deuterium, hydrogen, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphine, and combinations thereof.

In some embodiments, the compound of the present invention has formula IV:

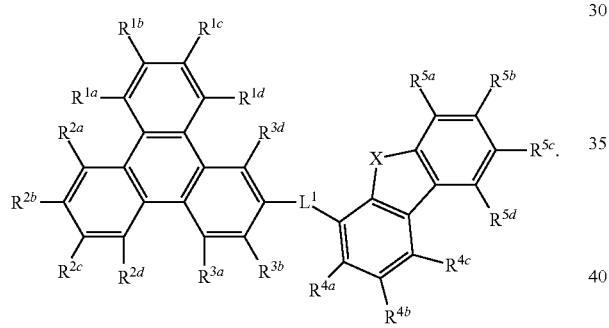

(IV)

In some embodiments, the compound of the present invention has formula V:

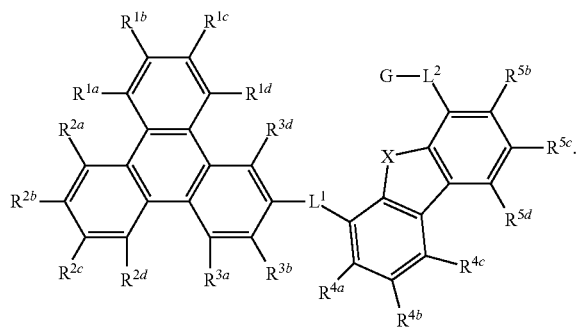

(V)

In some embodiments, the compound is selected from the group consisting of:

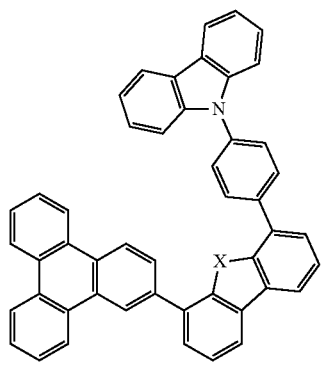

Compound 1-X

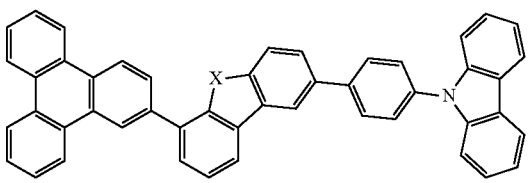

Compound 2-X

-continued
Compound 3-X
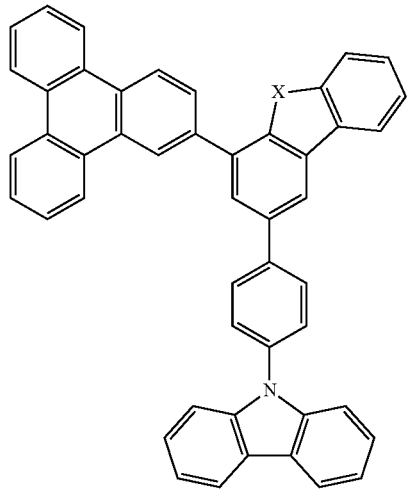
Compound 4-X
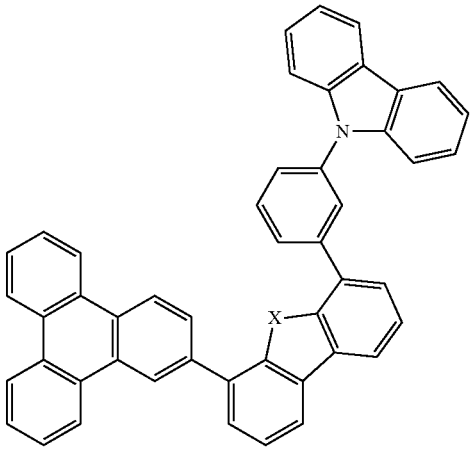
Compound 5-X
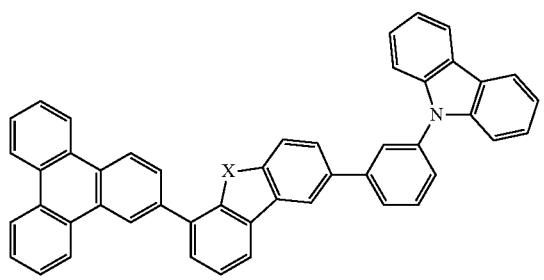
Compound 6-X
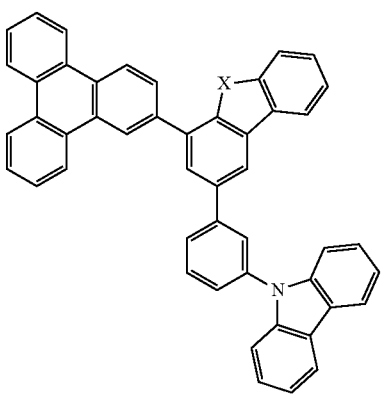
Compound 7-X
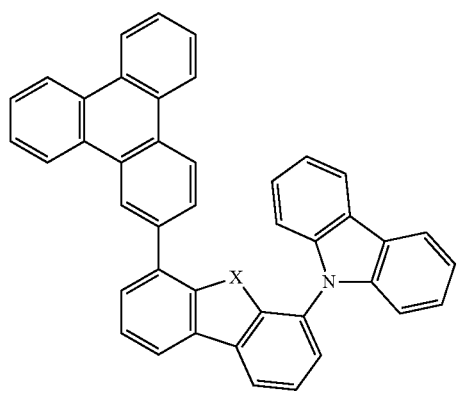
Compound 8-X
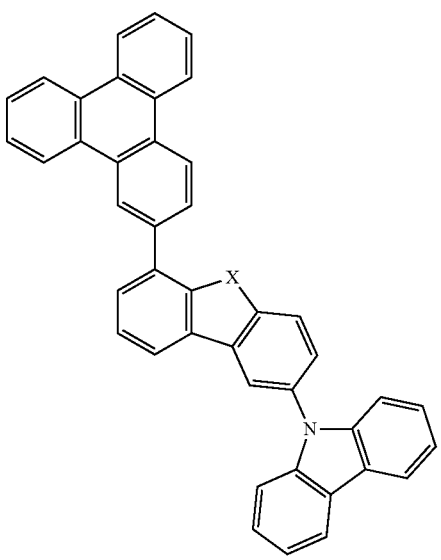

-continued
Compound 9-X
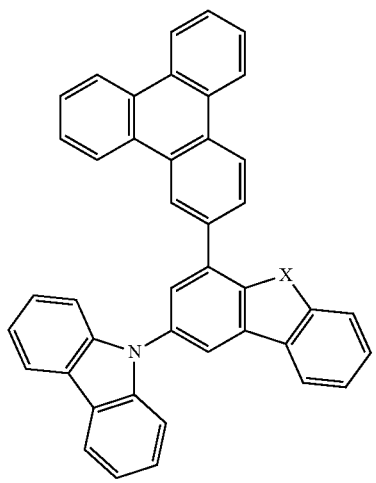
Compound 10-X
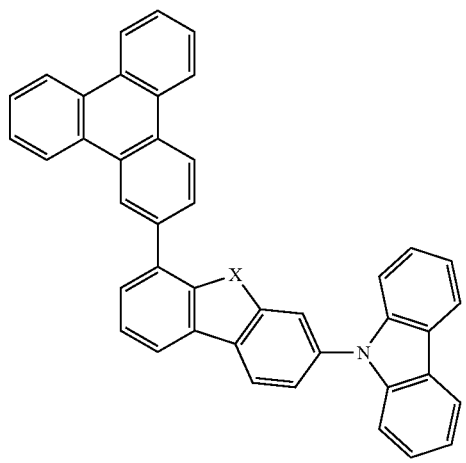
Compound 11-X
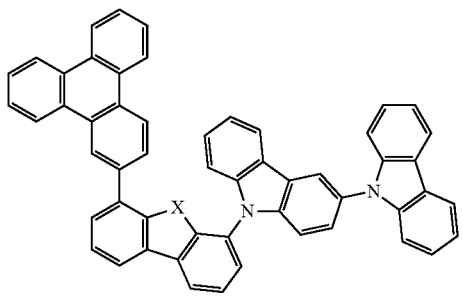
Compound 12-X
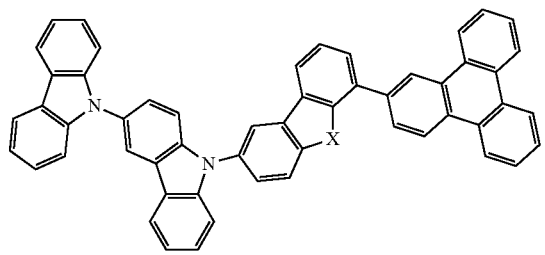
Compound 13-X
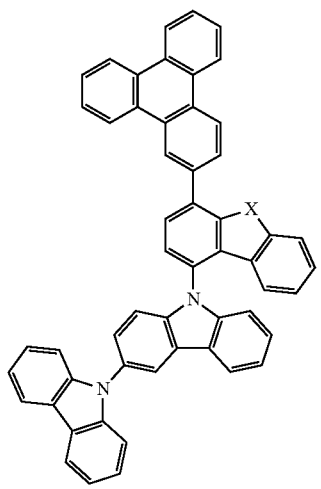
Compound 14-X
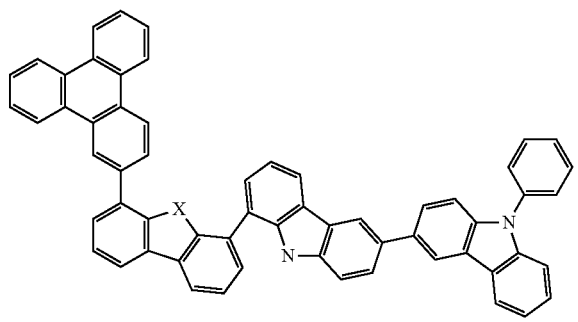

-continued
Compound 15-X
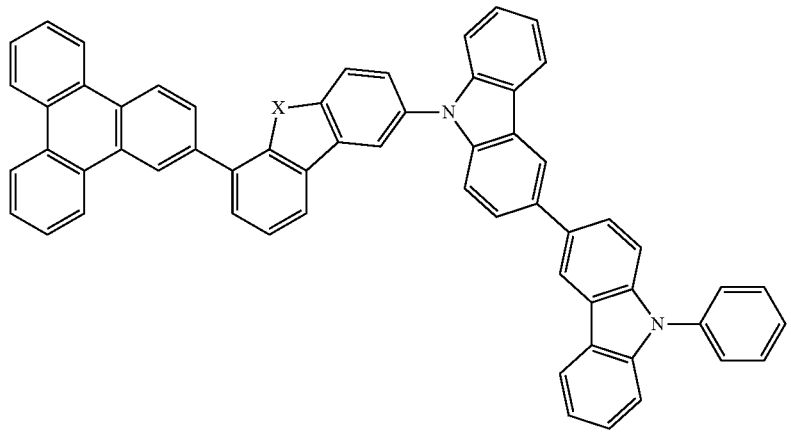
Compound 16-X
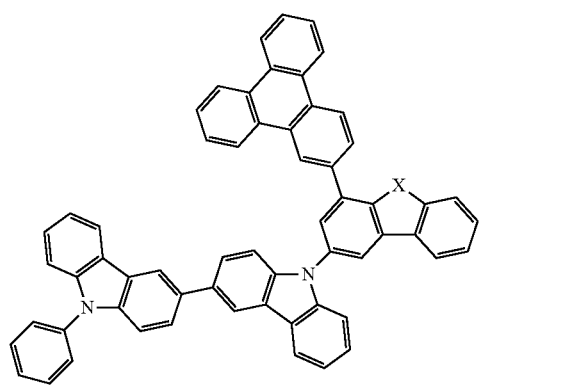
Compound 17-X
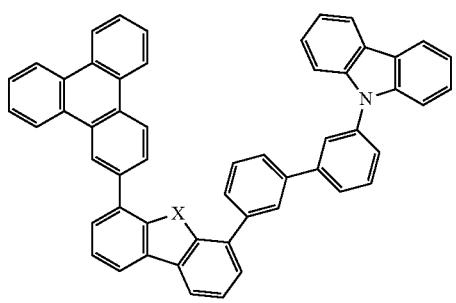
Compound 18-X
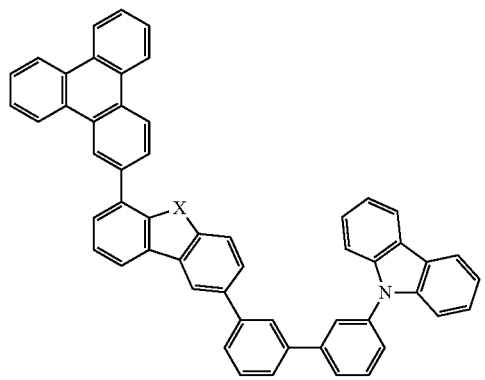
Compound 19-X
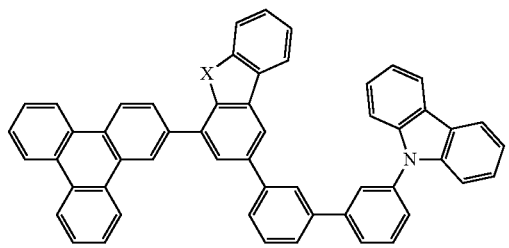
Compound 20-X
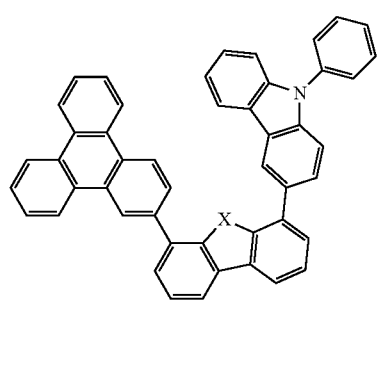
Compound 21-X -continued
Compound 22-X        Compound 23-X
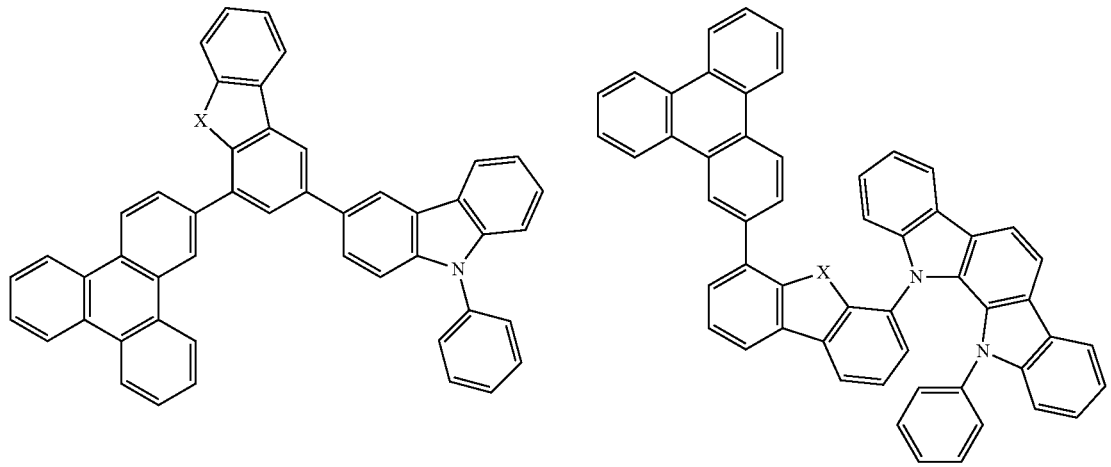
Compound 24-X        Compound 25-X
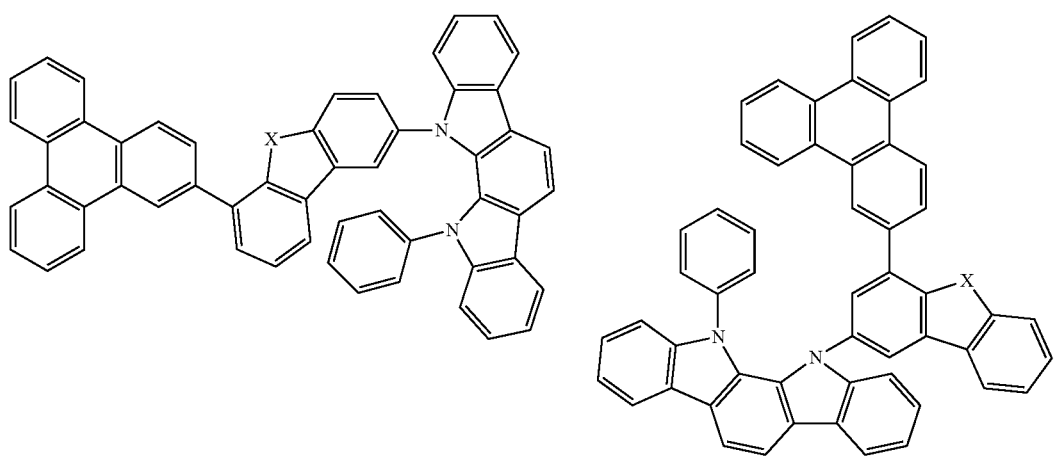
Compound 26-X        Compound 27-X
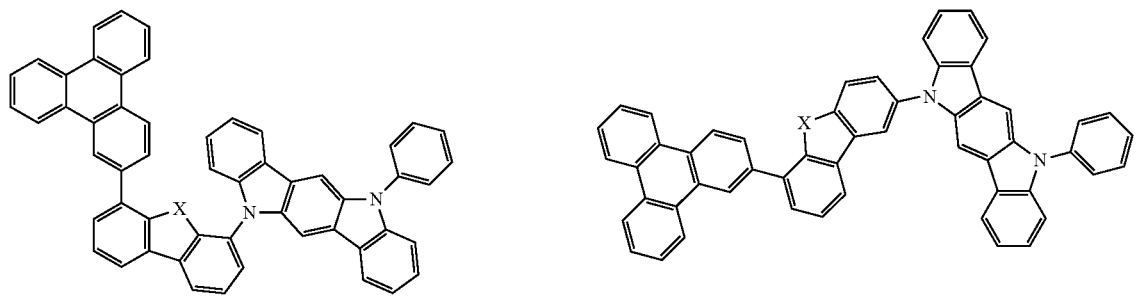

-continued
Compound 28-X
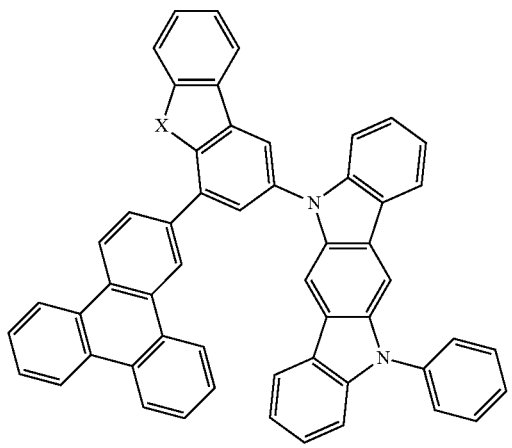
Compound 29-X
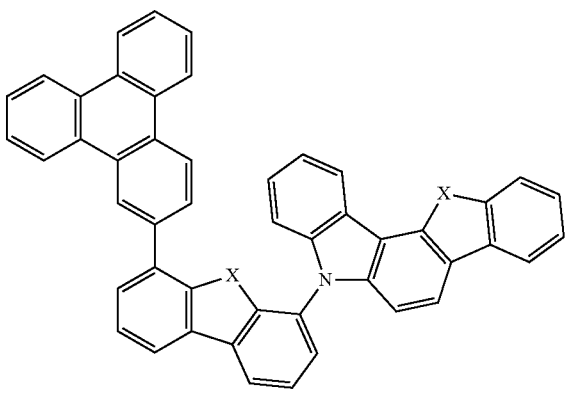
Compound 30-X
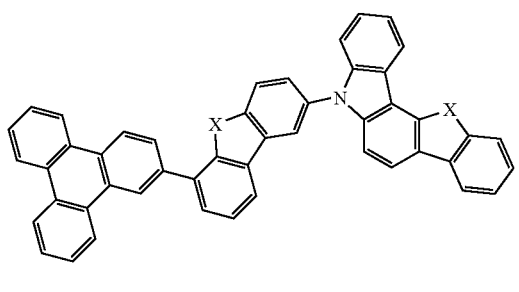
Compound 31-X
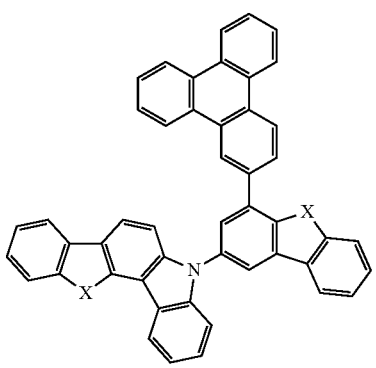
Compound 32-X
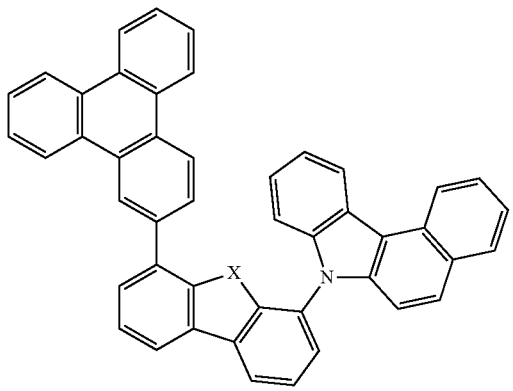
Compound 33-X
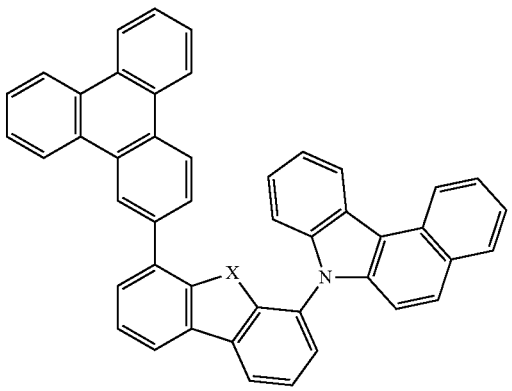
Compound 34-X
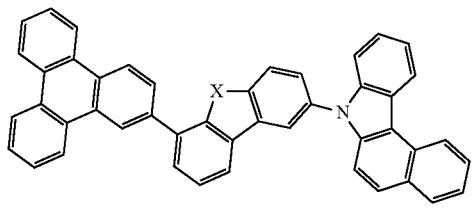
Compound 35-X
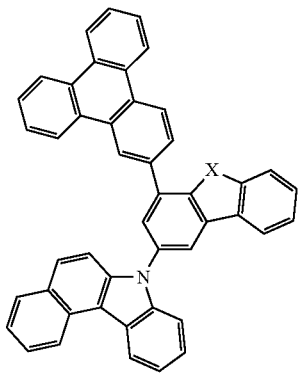

-continued
Compound 36-X
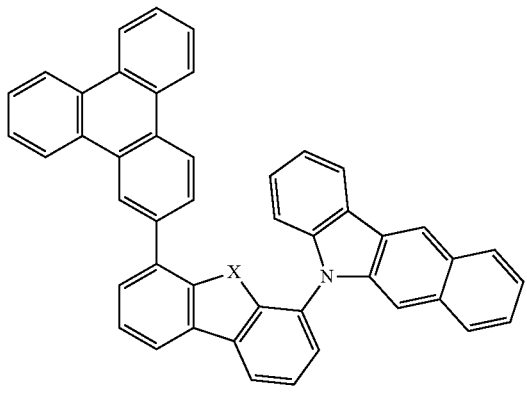
Compound 37-X
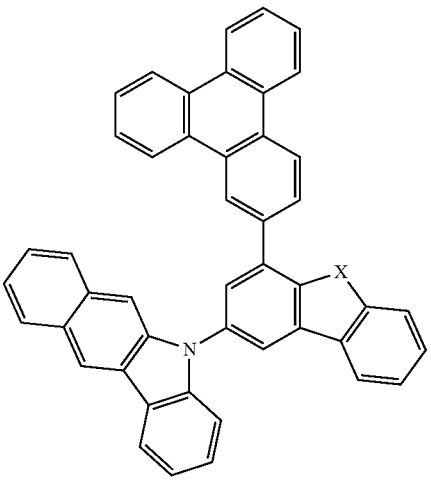
Compound 38-X
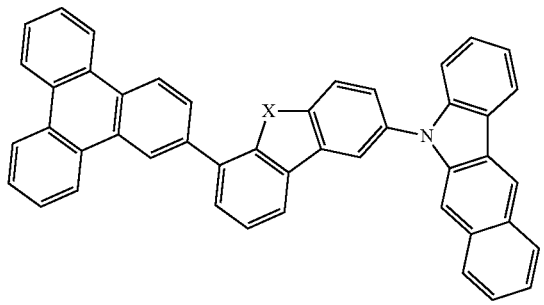
Compound 39-X
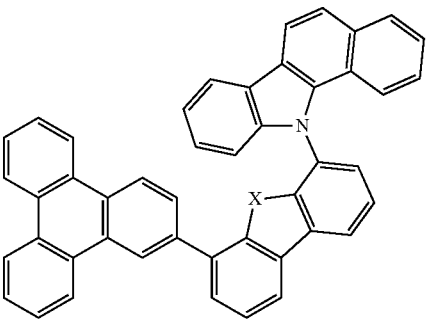
Compound 40-X
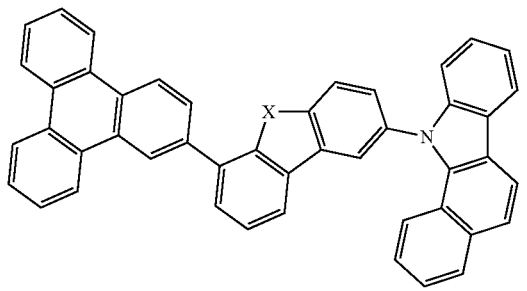
Compound 41-X
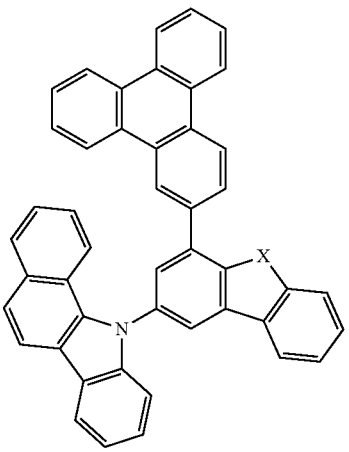

-continued

Compound 42-X

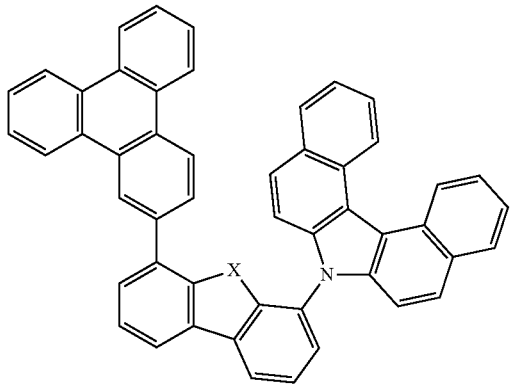

Compound 43-X

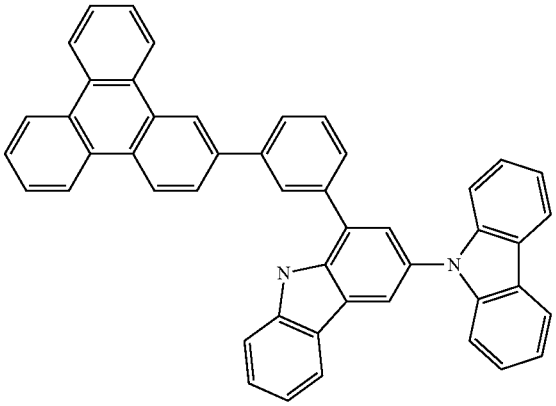

Compound 44-X

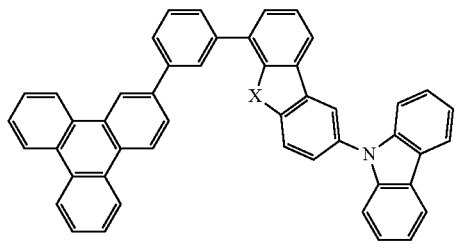

Compound 45-X

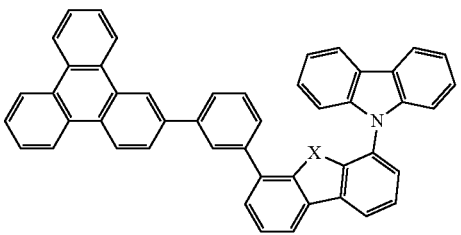

and

Compound 46-X

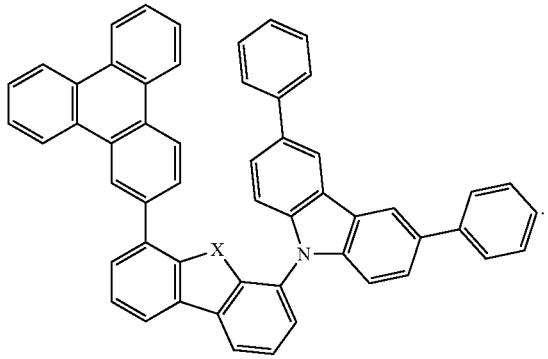

The present invention also provides an organic light emitting device. The organic light emitting device comprises:
an anode;
a cathode;
an organic layer, disposed between the anode and the cathode, wherein the organic layer comprises a compound having formula I:

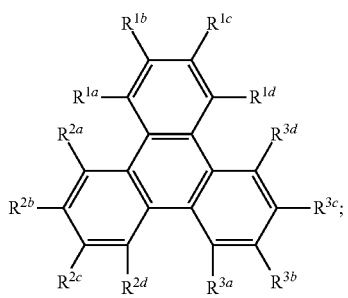

(I)

wherein at least one of $R^{3a}$, $R^{3b}$, $R^{3c}$, or $R^{3d}$ has formula II:

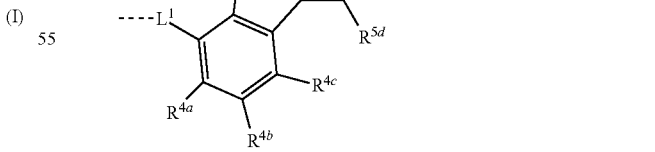

(II)

wherein at least one of $R^{4a}$, $R^{4b}$, $R^{4c}$, $R^{5a}$, $R^{5b}$, $R^{5c}$, or $R^{5d}$ has formula III:

-L²-G        (III);

wherein $L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof;

wherein X is selected from the group consisting of O, S, and Se;

wherein G is a carbazole which may be optionally substituted; and wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

The present invention also provides a formulation comprising a compound of formula I.

BRIEF DESCRIPTION OF THE DRAWINGS

The accompanying drawings, which are incorporated herein and form a part of the specification, illustrate embodiments of the present invention and, together with the description, further serve to explain the principles of the invention and to enable a person skilled in the pertinent art to make and use the invention.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
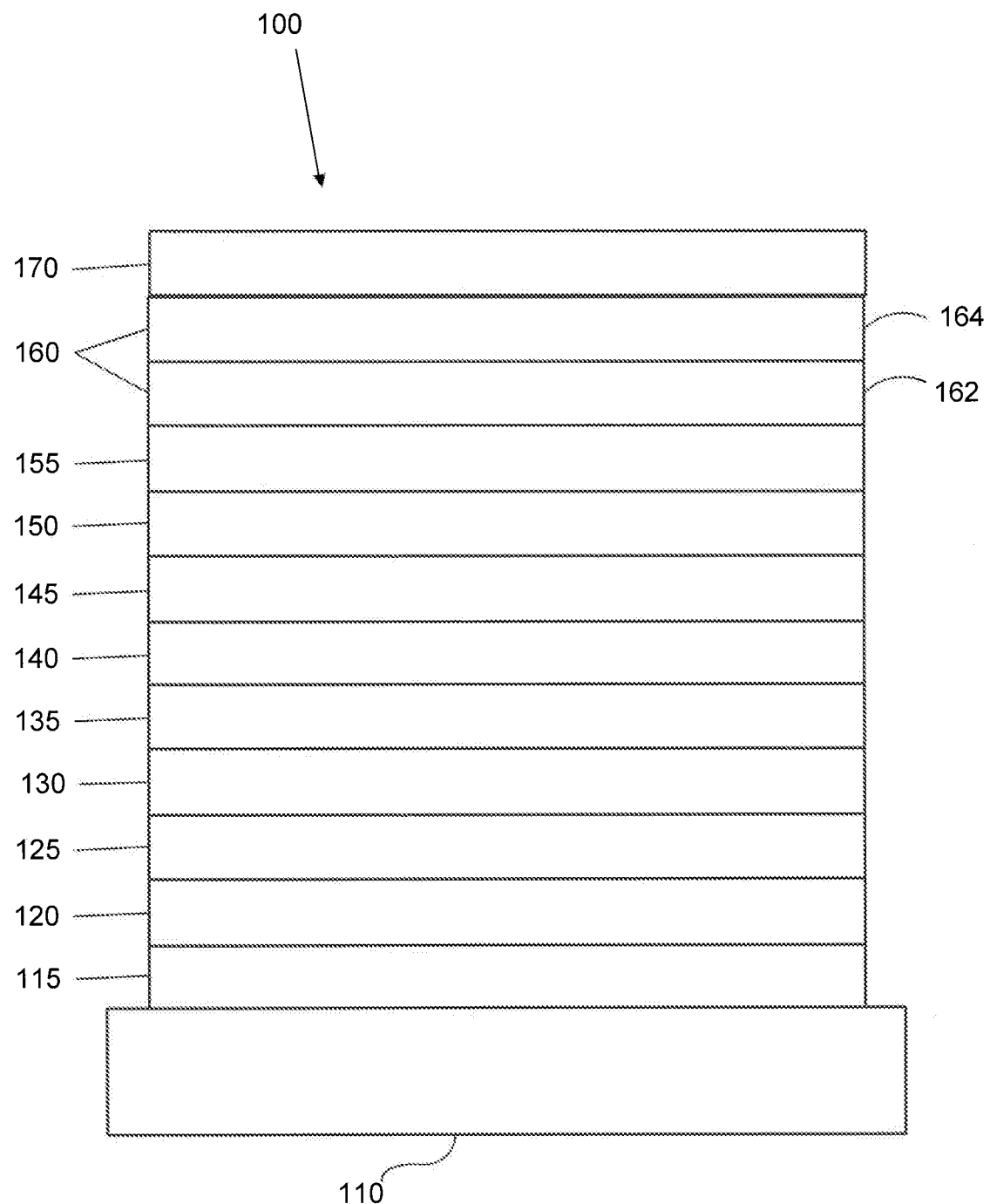
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
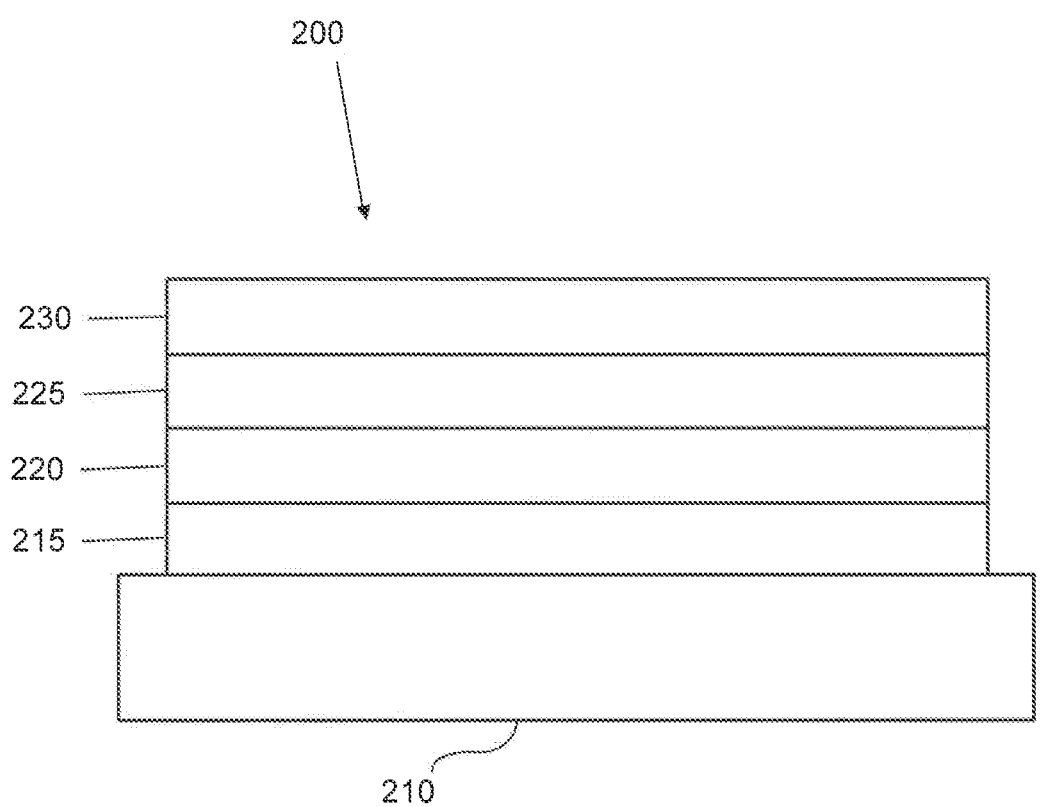
FIG. 2 shows an inverted organic light emitting device that does not have a separate electron transport layer.
Figure 3:
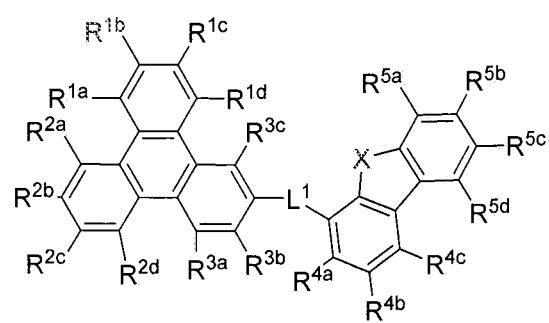
FIG. 3 shows a compound of Formula IV.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In some embodiments, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C to 30 degrees C, and more preferably at room temperature (20-25 degrees C), but could be used outside this temperature range, for example, from −40 degree C to +80 degrees C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein contemplates an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

As used herein, the term "substituted" indicates that a substituent other than hydrogen is bonded to the relevant carbon or nitrogen atom. Thus, where $R^1$ is mono-substituted, then one $R^1$ must be other than hydrogen. Similarly, where $R^1$ is di-substituted, then two of $R^1$ must be other than hydrogen. Similarly, where $R^1$ "represents no substitution," $R^1$ is hydrogen for all available positions.

The "aza" designation in the fragments described herein, i.e., aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g., naphthalene, dibenzofuran). As used herein, these different ways of designating a substituent or attached fragment are considered to be equivalent.

A wide variety of carbazole-containing compounds have been developed as organic electroluminescent materials. Depending on the unique ways building blocks are connected, these compounds have different energy levels, molecular packing, and charge-transport properties, all of which heavily influence device performance. This invention discloses a new class of compounds comprising a triphenylene and a carbazole. Unexpectedly, phosphorescent OLED devices using the compounds of the invention as host materials demonstrate superior stability compared to the compounds reported in the literature.

In some embodiments, a compound having formula I:

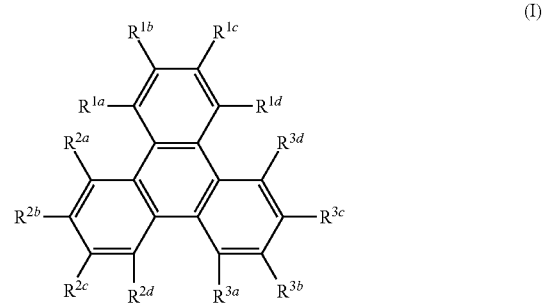

(I)

is provided. In the compound of formula I, at least one of $R^{3a}$, $R^{3b}$, $R^{3c}$, or $R^{3d}$ has formula II:

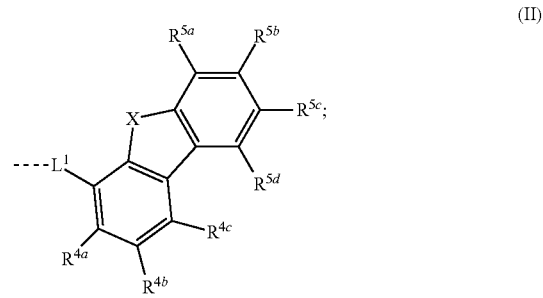

(II)

at least one of $R^{4a}$, $R^{4b}$, $R^{4c}$, $R^{5a}$, $R^{5b}$, $R^{5c}$, or $R^{5d}$ has formula III:

-$L^2$-G          (III);

L¹ and L² are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof; X is selected from the group consisting of O, S, and Se; G is a carbazole which may be optionally substituted; $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, G is connected to L² at the nitrogen atom of the 9-position of carbazole.

In some embodiments, G is connected to L² at a carbon atom at the 1-, 2-, 3-, or 4-position of carbazole.

In some embodiments, L¹ is a direct bond.

In some embodiments, one of $R^{4b}$, $R^{5a}$, or $R^{5c}$ is L²-G.

In some embodiments, L¹ and L² are independently selected from the group consisting of a direct bond, a phenyl group, and a biphenyl group.

In some embodiments, $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, aryl, heteroaryl, and combinations thereof, $R^{3a}$, $R^{3b}$, $R^{3c}$, and $R^{3d}$ that are not formula II are each independently selected from the group consisting of hydrogen, deuterium, aryl, heteroaryl, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, aryl, heteroaryl, and combinations thereof.

In some embodiments, $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, $R^{3a}$, $R^{3b}$, $R^{3c}$, and $R^{3d}$ that are not formula II are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof.

In some embodiments, $R^{1a}$, $R^{1b}$, $R^{1c}$, $R^{1d}$, $R^{2a}$, $R^{2b}$, $R^{2c}$, and $R^{2d}$ are hydrogen, $R^{3a}$, $R^{3b}$, $R^{3c}$, and $R^{3d}$ that are not formula II are hydrogen, and $R^{4a}$, $R^{4b}$, $R^{4c}$, $R^{5a}$, $R^{5b}$, $R^{5c}$, and $R^{5d}$ that are not formula III are hydrogen.

In some embodiments, X is O.

In some embodiments, X is S.

In some embodiments, X is S, L¹ and L² are a direct bond, and $R^{5a}$ is L²-G.

In some embodiments, X is S, L¹ is a direct bond, L² is phenyl, and $R^{5a}$ is L²-G.

In some embodiments, G is substituted with one or more substituents selected from the group consisting of deuterium, hydrogen, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphine, and combinations thereof.

In some embodiments, a compound having formula IV:

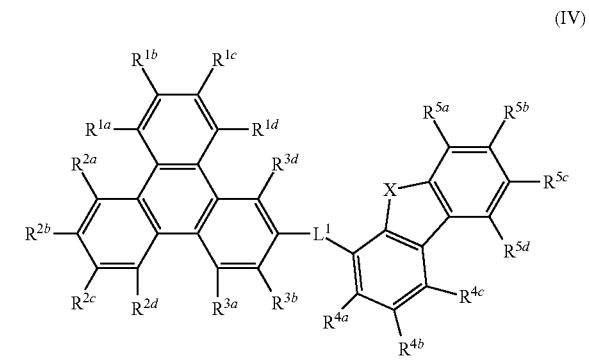

(IV)

is provided. In the compound of formula IV, at least one of $R^{4a}$, $R^{4b}$, $R^{4c}$, $R^{5a}$, $R^{5b}$, $R^{5c}$, or $R^{5d}$ has formula:

-L²-G    (III);

L¹ and L² are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof; X is selected from the group consisting of O, S, and Se; G is a carbazole which may be optionally substituted; $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, and $R^{3d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, G is connected to $L^2$ at the nitrogen atom of the 9-position of carbazole.

In some embodiments, G is connected to $L^2$ at a carbon atom at the 1-, 2-, 3-, or 4-position of carbazole.

In some embodiments, $L^1$ is a direct bond.

In some embodiments, one of $R^{4b}$, $R^{5a}$, or $R^{5c}$ is $L^2$-G.

In some embodiments, $L^1$ and $L^2$ are independently selected from the group consisting of a direct bond, a phenyl group, and a biphenyl group.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, and $R^{3d}$ are each independently selected from the group consisting of hydrogen, deuterium, aryl, heteroaryl, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, aryl, heteroaryl, and combinations thereof.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, and $R^{3d}$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, and $R^{3d}$ are hydrogen and $R^{4a}$, $R^{4b}$, $R^{4c}$, $R^{5a}$, $R^{5b}$, $R^{5c}$, and $R^{5d}$ that are not formula III are hydrogen.

In some embodiments, X is O.

In some embodiments, X is S.

In some embodiments, X is S, $L^1$ and $L^2$ are a direct bond, and $R^{5a}$ is $L^2$-G.

In some embodiments, X is S, $L^1$ is a direct bond, $L^2$ is phenyl, and $R^{5a}$ is $L^2$-G.

In some embodiments, G is substituted with one or more substituents selected from the group consisting of deuterium, hydrogen, halogen, alkyl, cycloalkyl, heteroalkyl, aralkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphine, and combinations thereof.

In some embodiments, a compound having formula V:

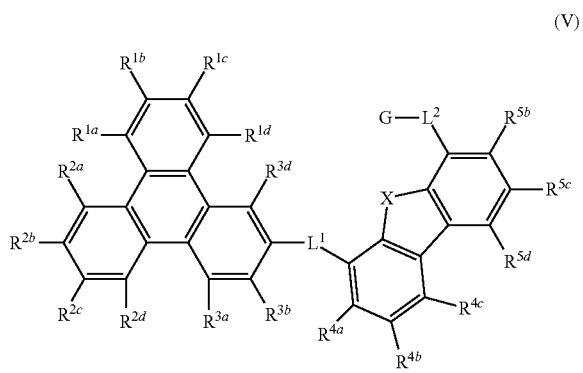

(V)

is provided. In the compound of formula V, $L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, and combinations thereof; X is selected from the group consisting of O, S, and Se; G is a carbazole which may be optionally substituted; $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3d}$, $R^{4a}$, $R^{4b}$, $R^{4c}$, $R^{5b}$, $R^{5c}$, and $R^{5d}$ are each independently selected from the group consisting of hydrogen, deuterium, halogen, alkyl, cycloalkyl, heteroalkyl, aralkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, G is connected to $L^2$ at the nitrogen atom of the 9-position of carbazole.

In some embodiments, G is connected to $L^2$ at a carbon atom at the 1-, 2-, 3-, or 4-position of carbazole.

In some embodiments, $L^1$ is a direct bond.

In some embodiments, $L^1$ and $L^2$ are independently selected from the group consisting of a direct bond, a phenyl group, and a biphenyl group.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3d}$, $R^{4a}$, $R^{4b}$, $R^{4c}$, $R^{5b}$, $R^{5c}$, and $R^{5d}$ are each independently selected from the group consisting of hydrogen, deuterium, aryl, heteroaryl, and combinations thereof.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3d}$, $R^{4a}$, $R^{4b}$, $R^{4c}$, $R^{5b}$, $R^{5c}$, and $R^{5d}$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof.

In some embodiments, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3d}$, $R^{4a}$, $R^{4b}$, $R^{4c}$, $R^{5b}$, $R^{5c}$, and $R^{5d}$ are hydrogen.

In some embodiments, X is O.

In some embodiments, X is S.

In some embodiments, X is S and $L^1$ and $L^2$ are a direct bond.

In some embodiments, X is S, $L^1$ is a direct bond, and $L^2$ is phenyl.

In some embodiments, G is substituted with one or more substituents selected from the group consisting of deuterium, hydrogen, halogen, alkyl, cycloalkyl, heteroalkyl, aralkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphine, and combinations thereof.

In some embodiments, the compound is selected from the group consisting of:

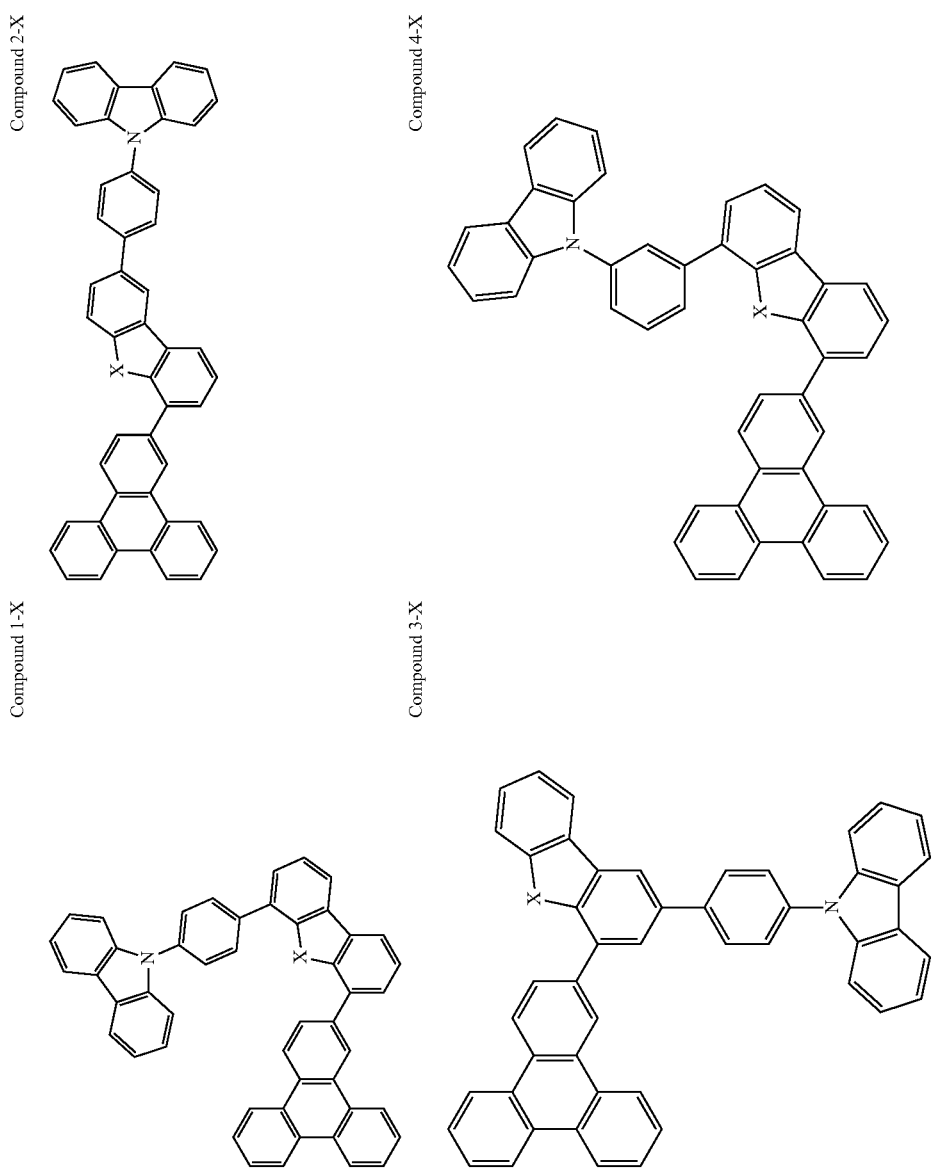

-continued
Compound 5-X
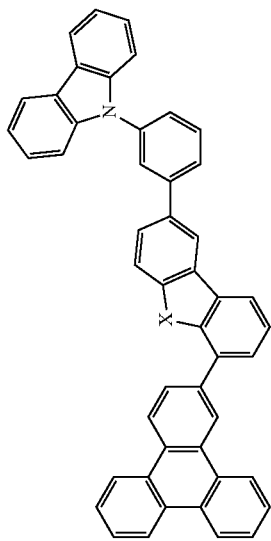
Compound 6-X
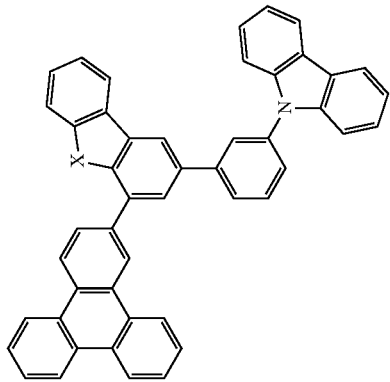
Compound 8-X
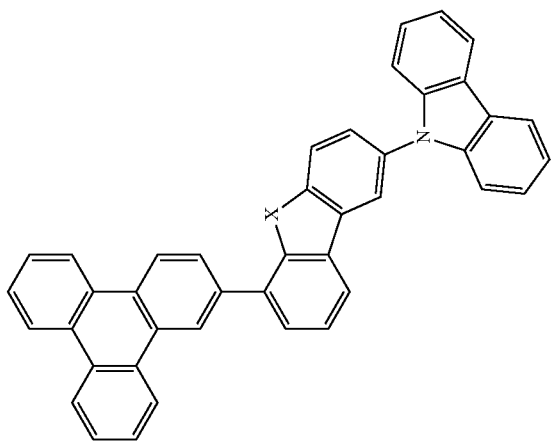
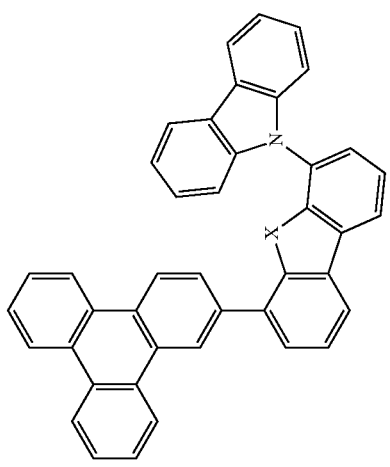

-continued
Compound 9-X
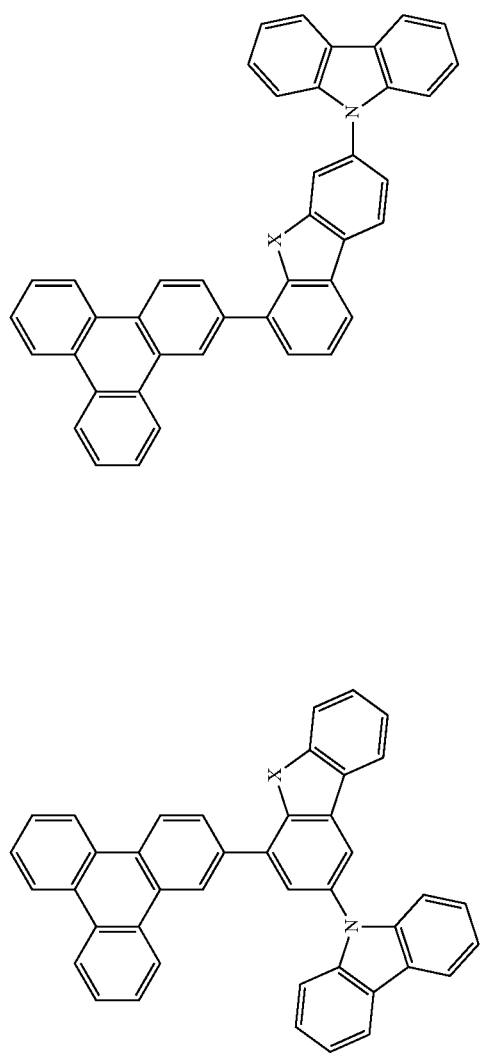
Compound 10-X
Compound 11-X
Compound 12-X

-continued
Compound 13-X
Compound 14-X
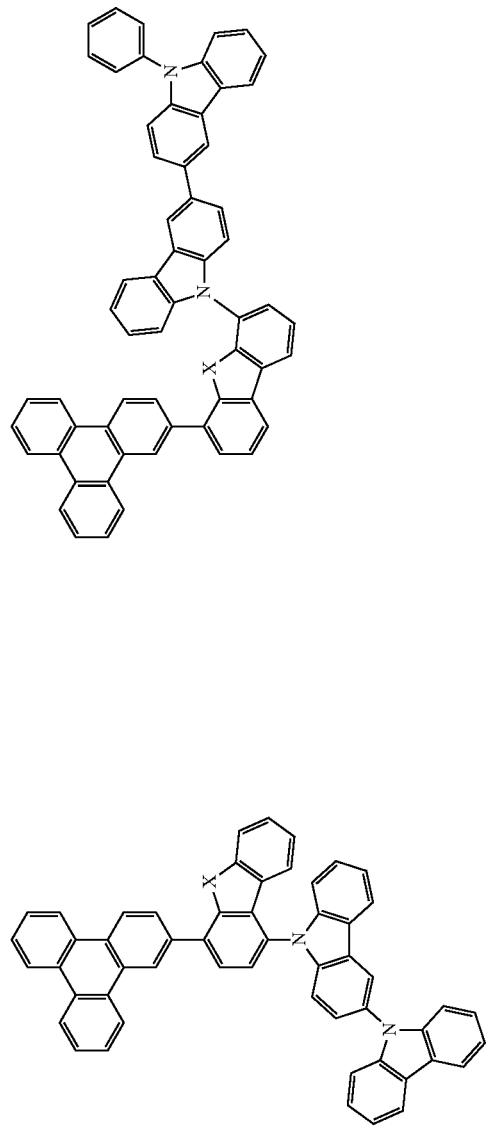
Compound 15-X
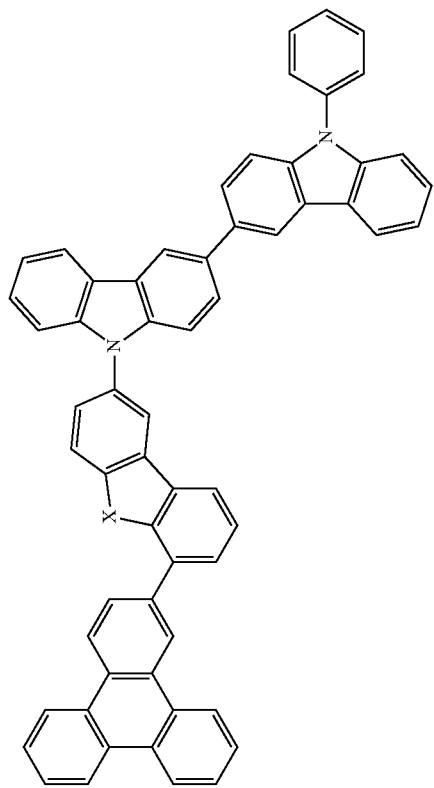

-continued
Compound 16-X
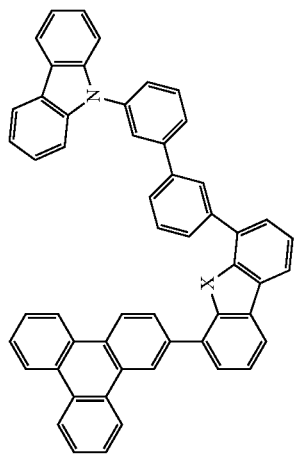
Compound 17-X
Compound 18-X
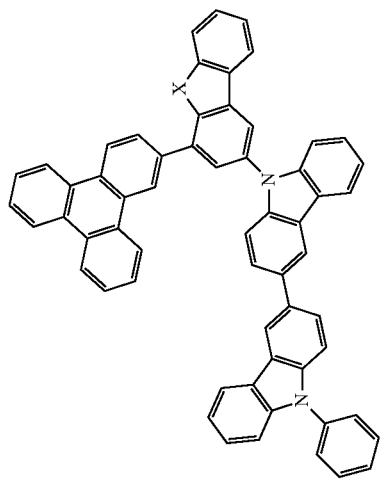
Compound 19-X
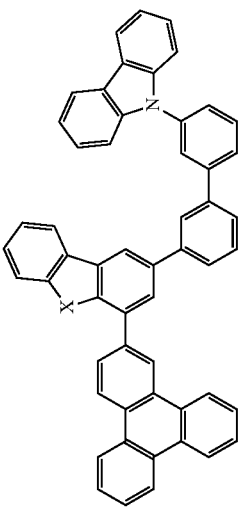
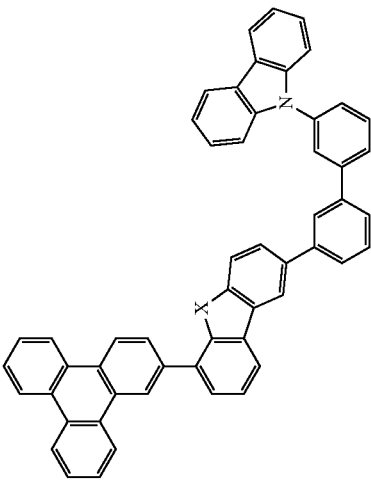

-continued
Compound 20-X
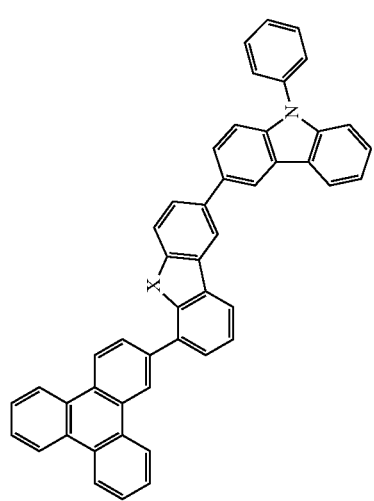
Compound 21-X
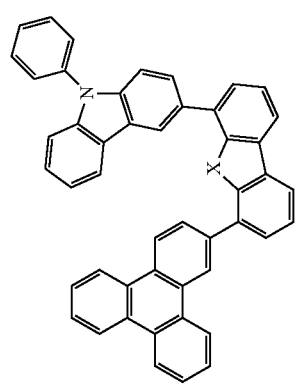
Compound 22-X
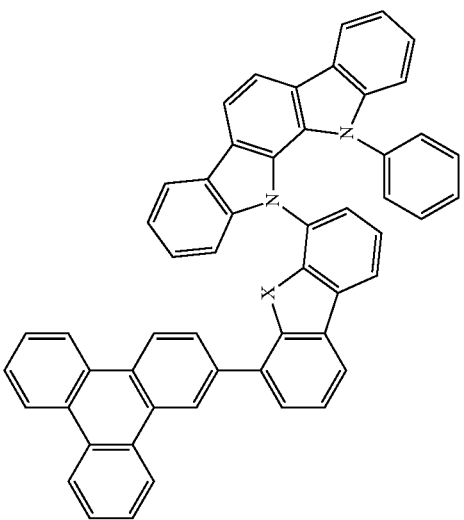
Compound 23-X
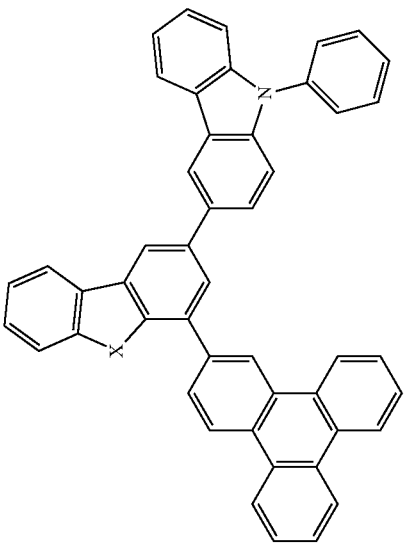

-continued
Compound 24-X
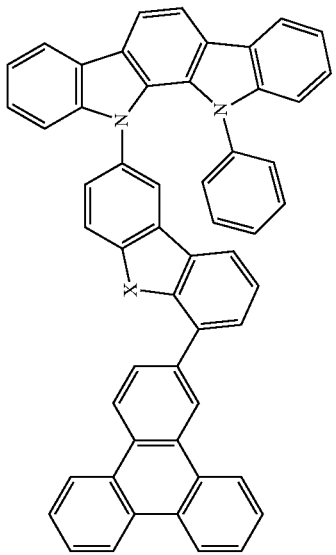
Compound 25-X
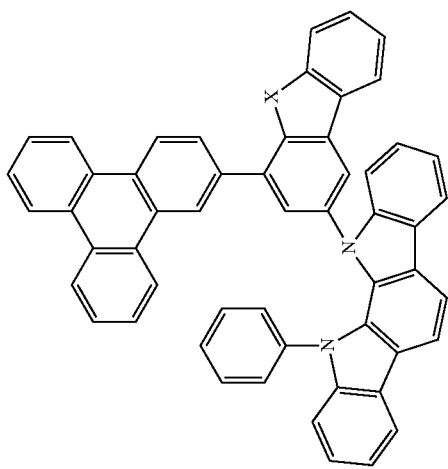
Compound 26-X
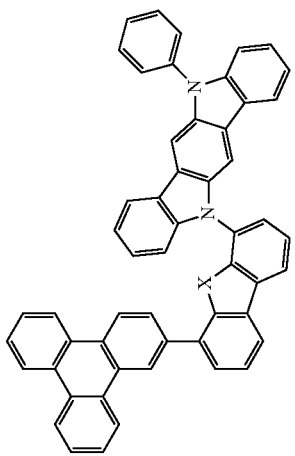
Compound 27-X
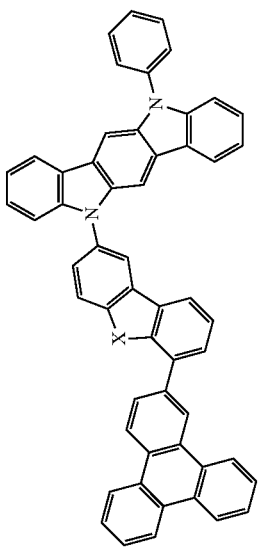

-continued
Compound 28-X
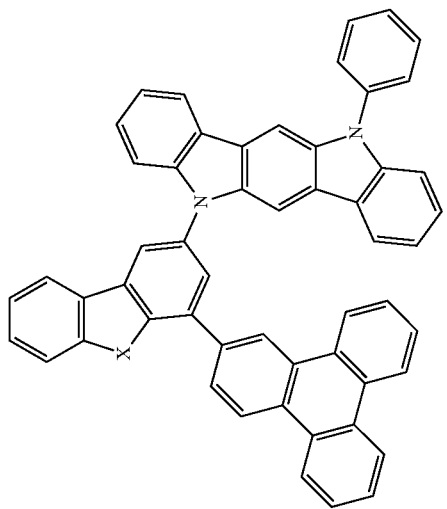
Compound 29-X
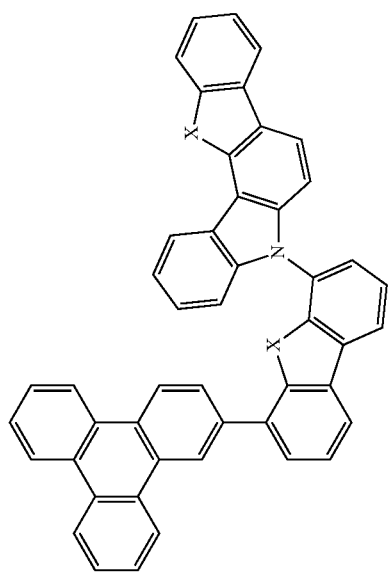
Compound 30-X
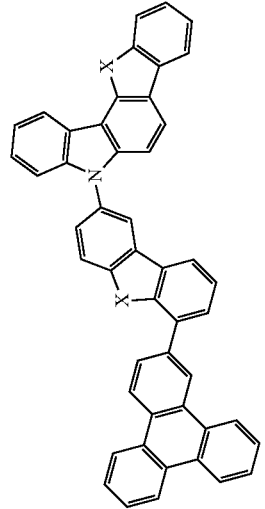
Compound 31-X
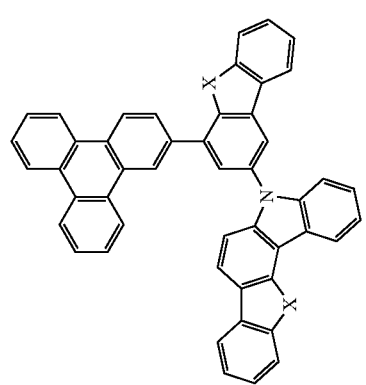

-continued
Compound 32-X
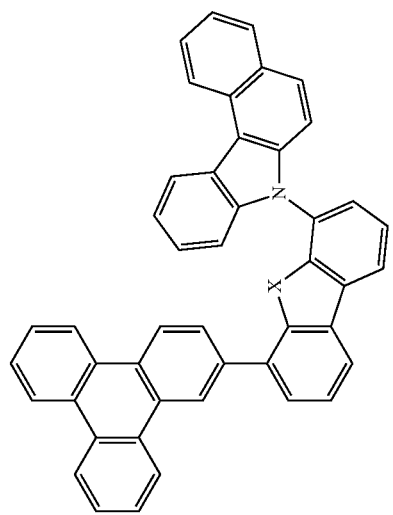
Compound 33-X
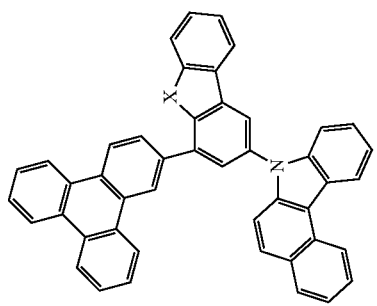
Compound 34-X
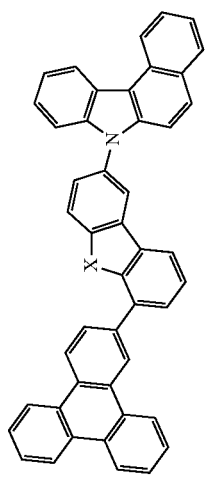
Compound 35-X
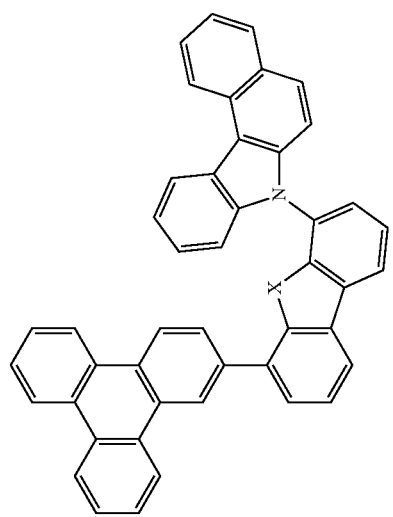

-continued
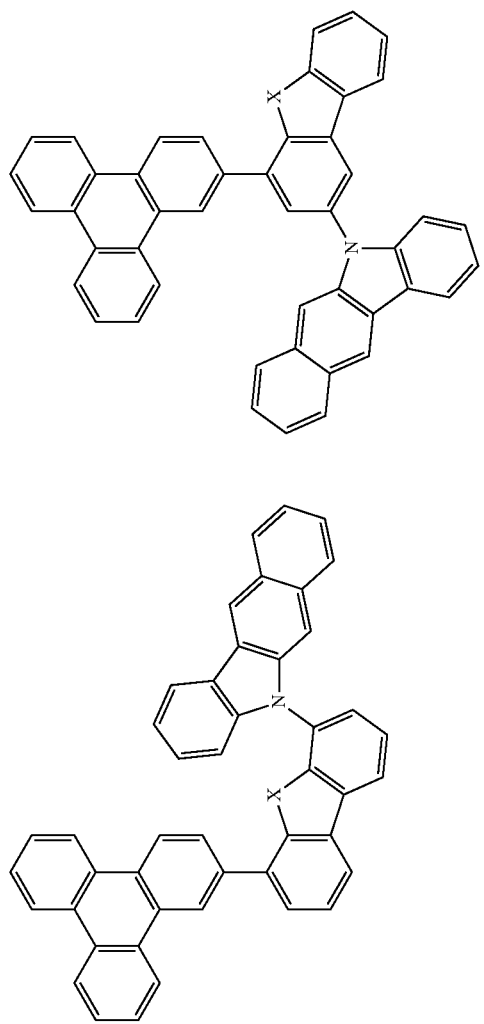
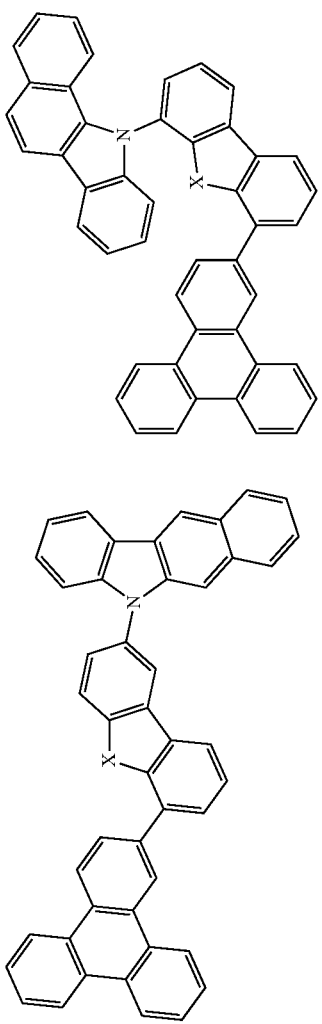

-continued
Compound 40-X
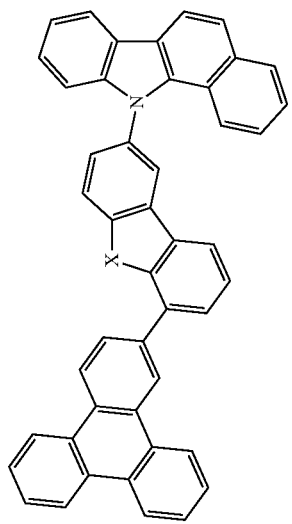
Compound 41-X
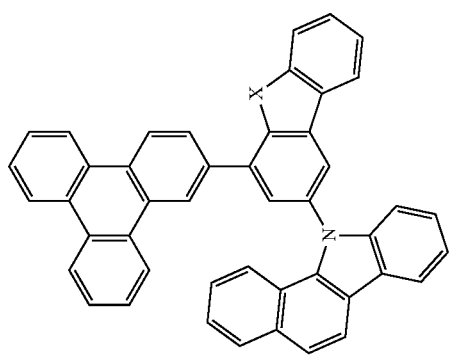
Compound 42-X
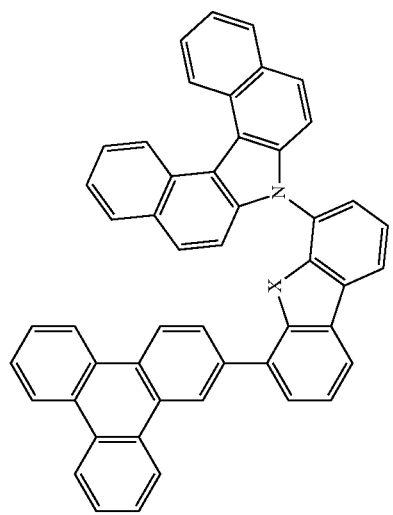
Compound 43-X
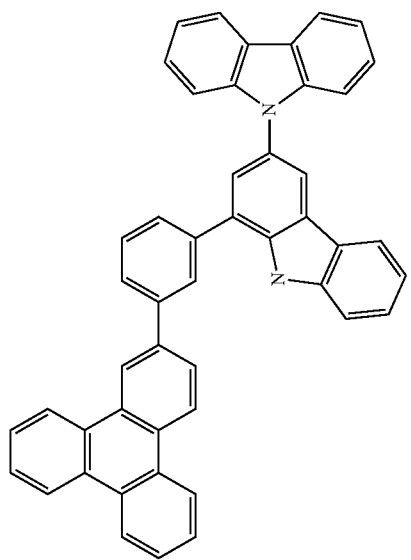

-continued
Compound 44-X
Compound 45-X
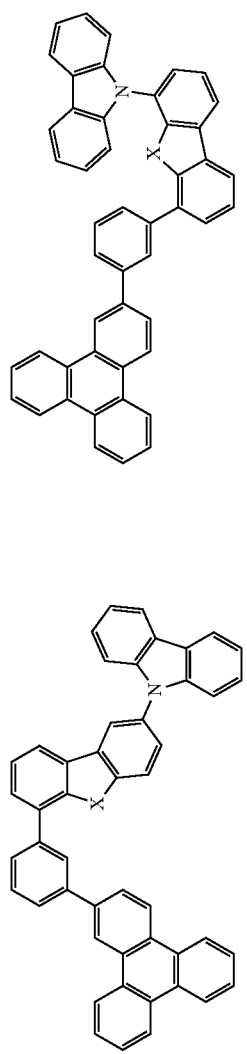
and
Compound 46-X
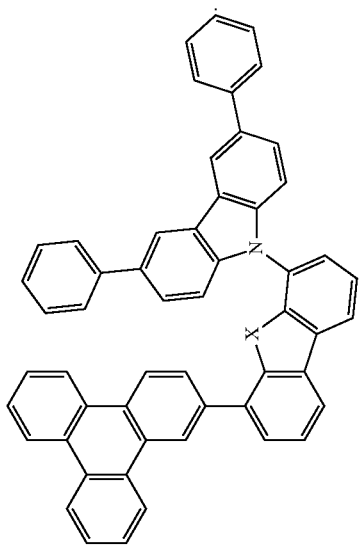

In some embodiments, an organic light emitting device is provided. In some embodiments, the organic light emitting device comprises:
an anode;
a cathode;
an organic layer, disposed between the anode and the cathode, wherein the organic layer comprises a compound having formula I:

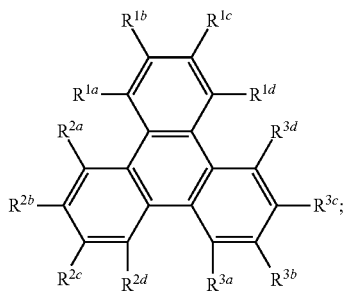

(I)

wherein at least one of $R^{3a}$, $R^{3b}$, $R^{3c}$, or $R^{3d}$ has formula II:

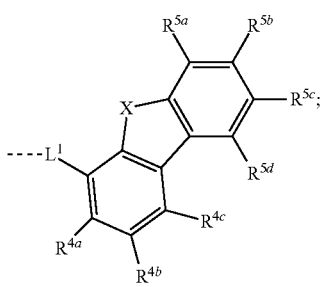

(II)

wherein at least one of $R^{4a}$, $R^{4b}$, $R^{4c}$, $R^{5a}$, $R^{5b}$, $R^{5c}$, or $R^{5d}$ has formula II:

-L²-G    (III);

wherein $L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof; wherein X is selected from the group consisting of O, S, and Se; wherein G is a carbazole which may be optionally substituted; wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, an organic light emitting device is provided. In some embodiments, the organic light emitting device comprises:
an anode;
a cathode;
an organic layer, disposed between the anode and the cathode, wherein the organic layer comprises a compound having formula IV:

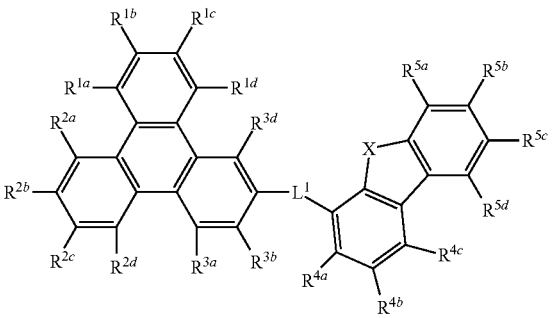

(IV)

wherein at least one of $R^{4a}$, $R^{4b}$, $R^{4c}$, $R^{5a}$, $R^{5b}$, $R^{5c}$, or $R^{5d}$ has formula III:

-L²-G    (III);

$L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, and combinations thereof; X is selected from the group consisting of O, S, and Se; G is a carbazole which may be optionally substituted; $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, and $R^{3d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, an organic light emitting device is provided. In some embodiments, the organic light emitting device comprises:
an anode;
a cathode;

an organic layer, disposed between the anode and the cathode, wherein the organic layer comprises a compound having formula V:

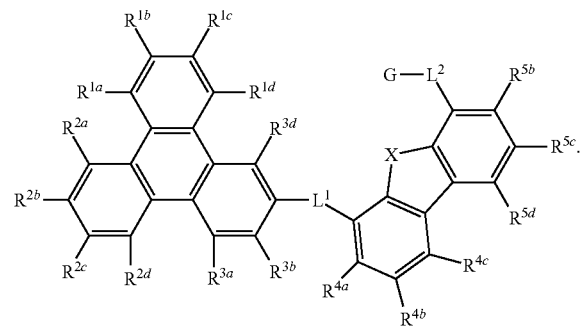

(V)

$L^1$ and $L^2$ are independently selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof; X is selected from the group consisting of O, S, and Se; G is a carbazole which may be optionally substituted; $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3d}$, $R^{4a}$, $R^{4b}$, $R^{4c}$, $R^{5b}$, $R^{5c}$, and $R^{5d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, the organic layer of the device is an emissive layer and the compound of formula I is a host. In some embodiments, the organic layer of the device is an emissive layer and the compound of formula IV is a host. In some embodiments, the organic layer of the device is an emissive layer and the compound of formula V is a host.

In some embodiments, the organic layer of the device further comprises a phosphorescent emissive dopant. In some embodiments, the phosphorescent emissive dopant is a transition metal complex having at least one ligand or part of the ligand if the ligand is more than bidentate selected from the group consisting of:

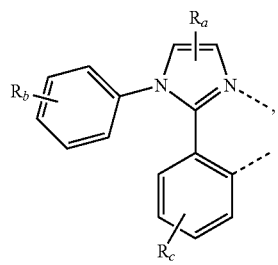

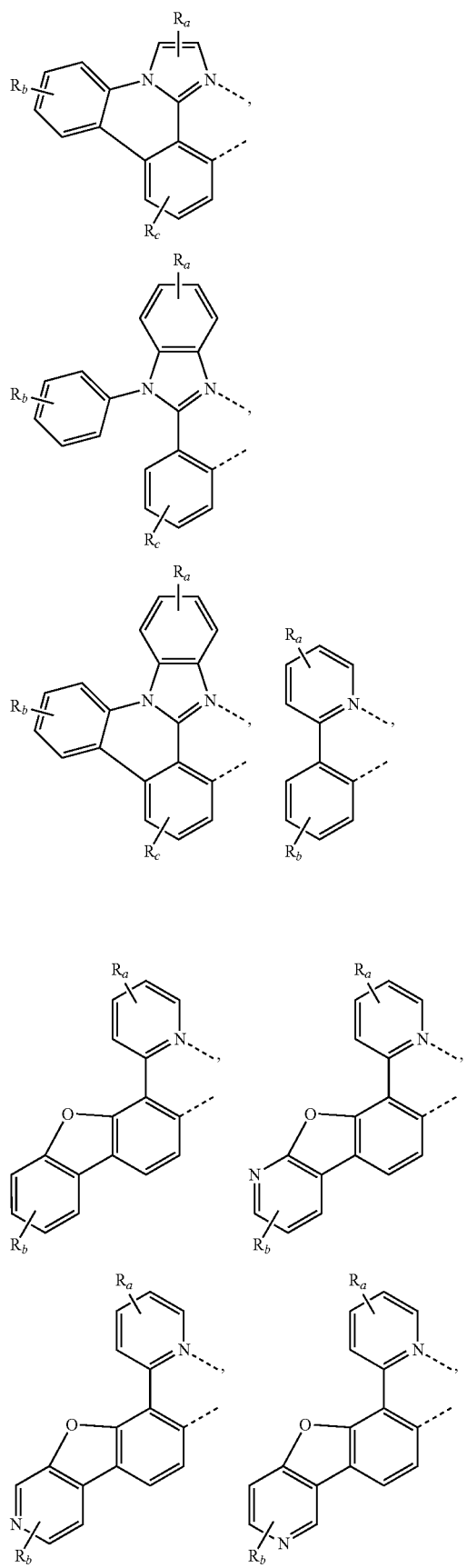

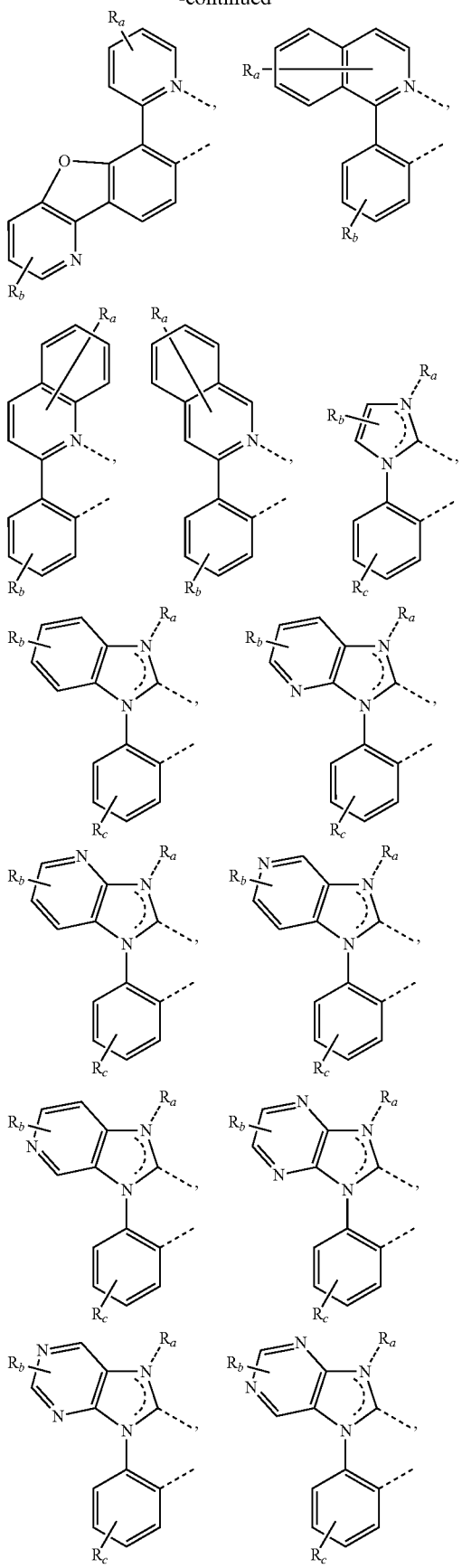

wherein $R_a$, $R_b$, $R_c$, and $R_d$ may represent mono, di, tri, or tetra substitution, or no substitution; and wherein $R_a$, $R_b$, $R_c$, and $R_d$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In some embodiments, the organic layer of the device is a blocking layer and the compound is a blocking material in the organic layer.

In some embodiments, the device is a consumer product. In some embodiments, the device is an organic light-emitting device. In some embodiments, the device comprises a lighting panel.

In some embodiments, the compounds described herein are provided in a formulation with other materials present in the device. For example, the compounds of the invention may be provided in a formulation in conjunction with a wide variety of hosts, transport layers, blocking layers, injection layers, electrodes, or other layers.

In some embodiments, a formulation comprising a compound of formula I is provided. In some embodiments, a formulation comprising a compound of formula IV is provided. In some embodiments, a formulation comprising a compound of formula V is provided.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and cross-linkable compounds.

Examples of aromatic amine derivatives used in HIL or HTL include, but are not limited to the following general structures:

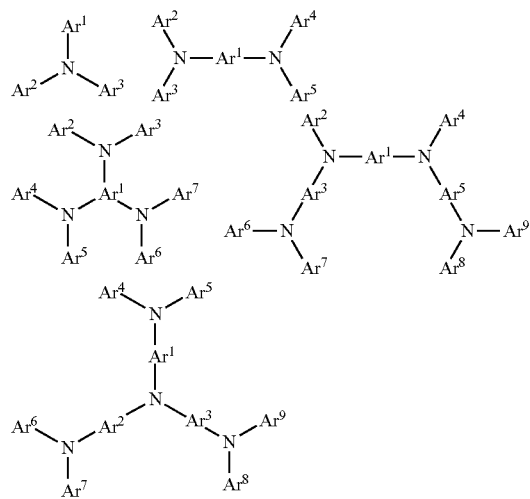

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some embodiments, $Ar^1$ to $Ar^9$ is independently selected from the group consisting of:

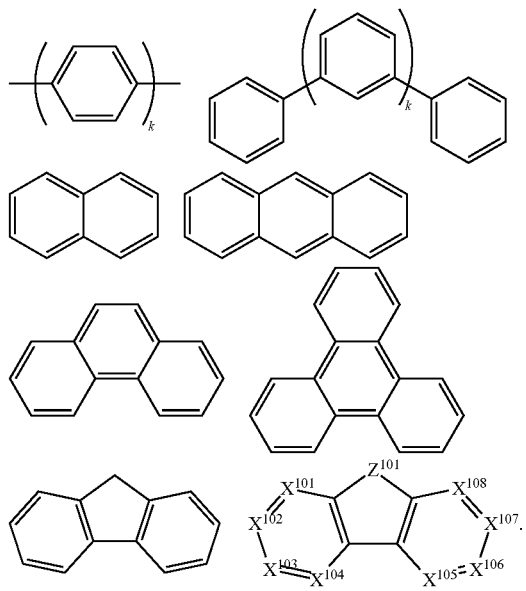

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

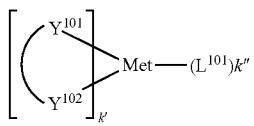

Met is a metal; $(Y^{101}-Y^{102})$ is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k'' is the maximum number of ligands that may be attached to the metal.

In some embodiments, $(Y^{101}-Y^{102})$ is a 2-phenylpyridine derivative.

In some embodiments, $(Y^{101}-Y^{102})$ is a carbene ligand.

In some embodiments, Met is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

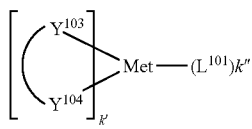

Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In some embodiments, the metal complexes are:

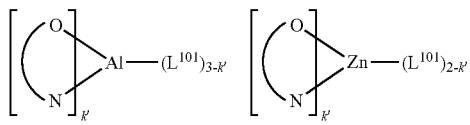

(O—N) is a bidentate ligand, having metal coordinated to atoms O and N.

In some embodiments, Met is selected from Ir and Pt.

In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some embodiments, the host compound contains at least one of the following groups in the molecule:

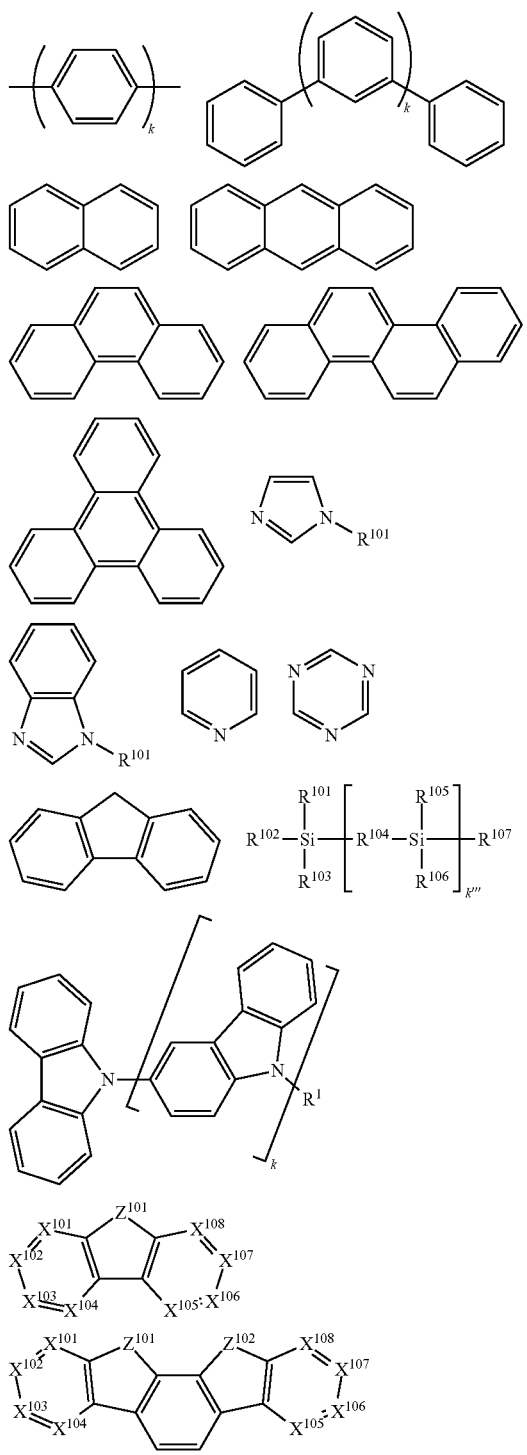

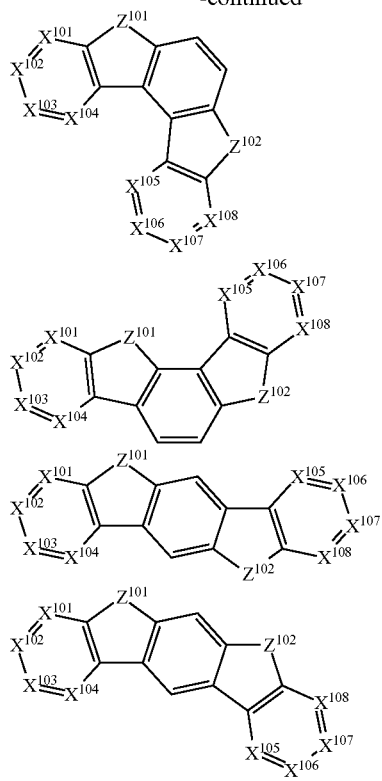

$R^{101}$ to $R^{107}$ is independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.
$X^{101}$ to $X^{108}$ is selected from C (including CH) or N.
$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In some embodiments, compound used in HBL contains the same molecule or the same functional groups used as host described above.

In some embodiments, compound used in HBL contains at least one of the following groups in the molecule:

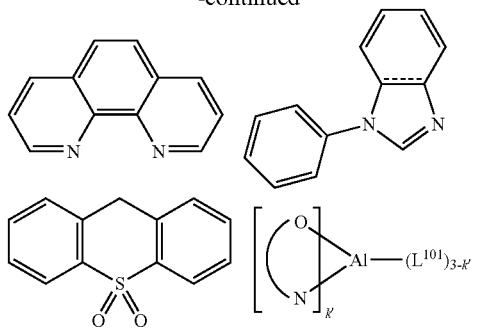

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In some embodiments, compound used in ETL contains at least one of the following groups in the molecule:

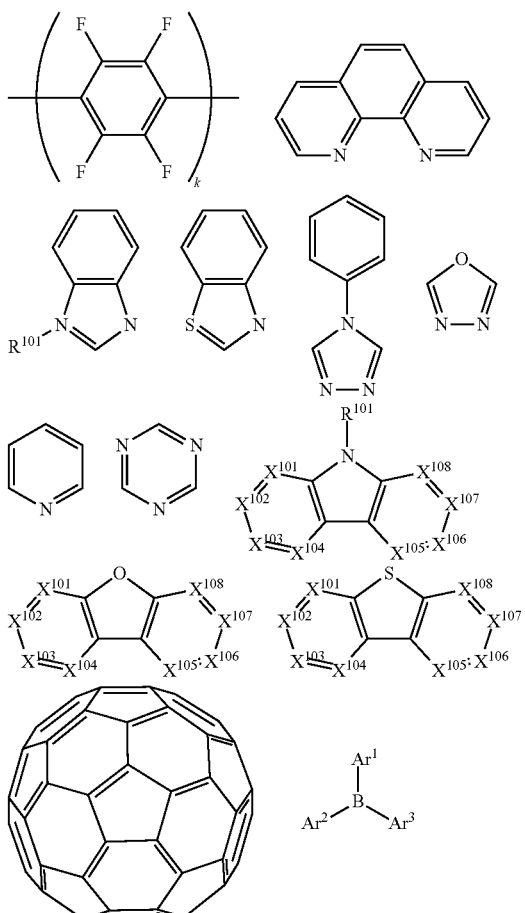

$R^{101}$ is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In some embodiments, the metal complexes used in ETL contains, but are not limited to the following general formula:

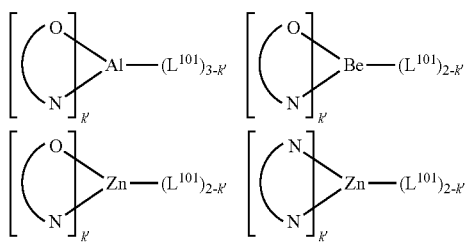

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in TABLE 1 below. TABLE 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |

TABLE 1-continued
| MATERIAL | EXAMPLES OF MATERIAL | PUBLICATIONS |
| --- | --- | --- |
| CF$_x$ Fluorohydrocarbon polymer | 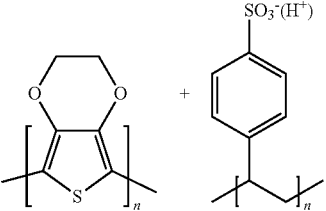 | Appl. Phys. Lett. 78, 673 (2001) |
| Conducting polymers (e.g., PEDOT:PSS, polyaniline, polythiophene) | 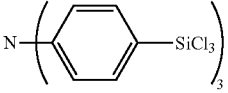 | Synth. Met. 87, 171 (1997) WO2007002683 |
| Phosphonic acid and silane SAMs | 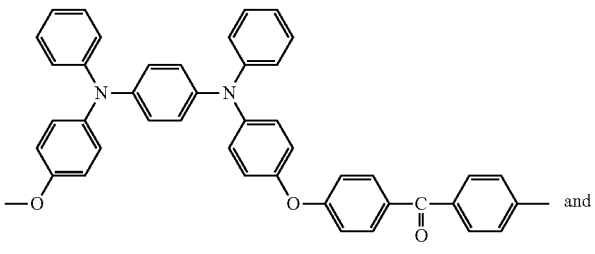 | US20030162053 |
| Triarylamine or polythiophene polymers with conductivity dopants | 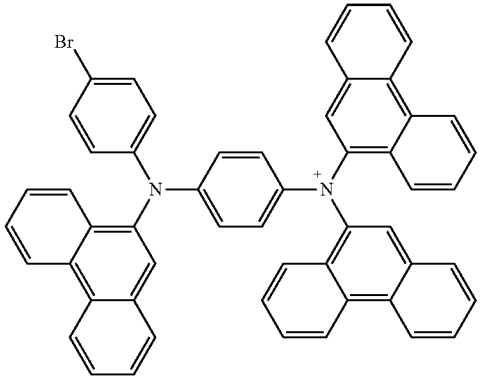 [SMILES: Brc1ccc(N(c2ccc(N(c3cc4ccccc4c4ccccc34)c3cc4ccccc4c4ccccc34)cc2)c2cc3ccccc3c3ccccc23)cc1]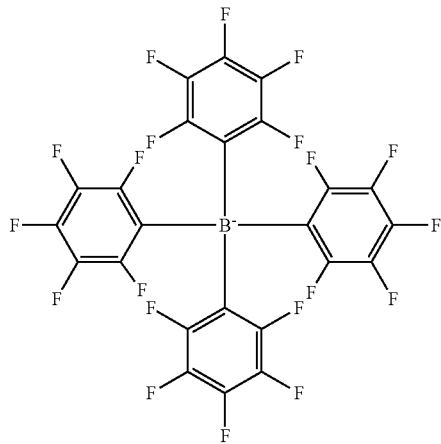 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |

TABLE 1-continued
| MATERIAL | EXAMPLES OF MATERIAL | PUBLICATIONS |
|---|---|---|
| Organic compounds with conductive inorganic compounds, such as molybdenum and tungsten oxides | 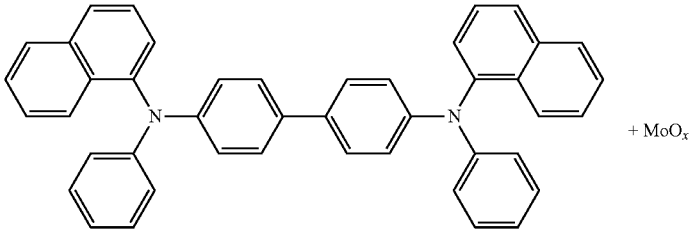 [SMILES: c1ccc(N(c2ccc(-c3ccc(N(c4ccccc4)c4cccc5ccccc45)cc3)cc2)c2cccc3ccccc23)cc1] + MoO$_x$ | US20050123751<br>SID Symposium Digest, 37, 923 (2006)<br>WO2009018009 |
| n-type semiconducting organic complexes | 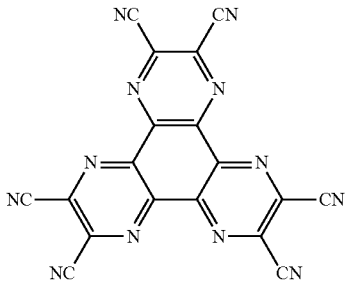 [SMILES: N#Cc1nc2c3nc(C#N)c(C#N)nc3c3nc(C#N)c(C#N)nc3c2nc1C#N] | US20020158242 |
| Metal organometallic complexes | 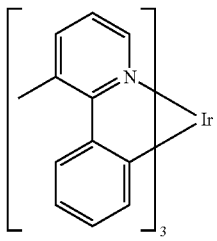 | US20060240279 |
| Cross-linkable compounds | 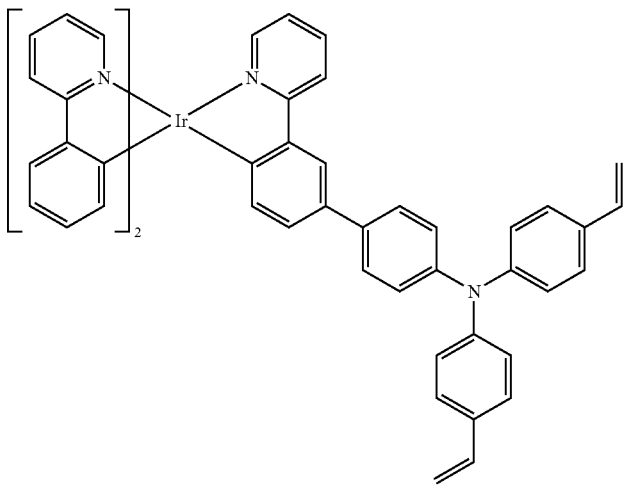 | US20080220265 |

TABLE 1-continued

| MATERIAL | EXAMPLES OF MATERIAL | PUBLICATIONS |
| --- | --- | --- |
| Polythiophene based polymers and copolymers | | WO 2011075644<br>EP2350216 |
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

TABLE 1-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |

TABLE 1-continued
| MATERIAL | EXAMPLES OF MATERIAL | PUBLICATIONS |
|---|---|---|
| Arylamine carbazole compounds | 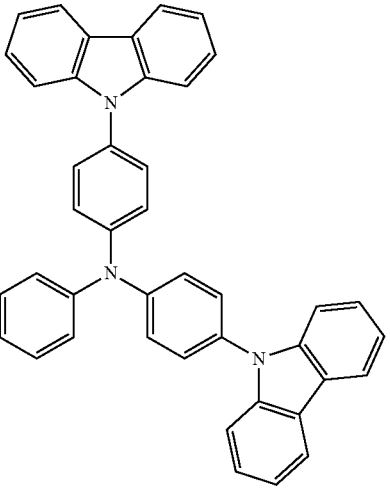 | Adv. Mater. 6, 677 (1994), US20080124572 |
| Triarylamine with (di)benzothiophene/ (di)benzofuran | 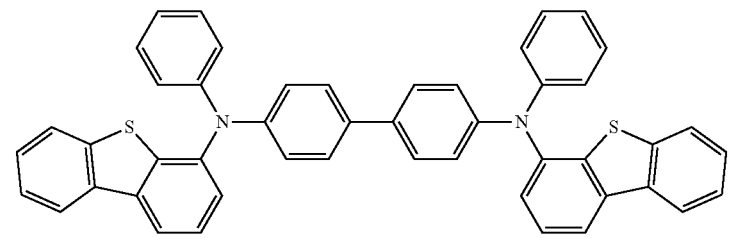 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 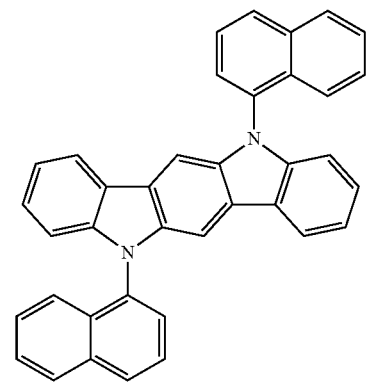 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 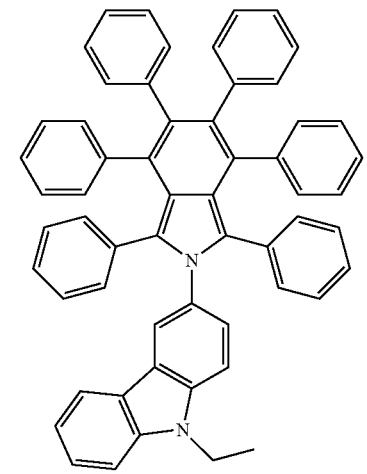 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 1-continued

| MATERIAL | EXAMPLES OF MATERIAL | PUBLICATIONS |
| --- | --- | --- |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |

TABLE 1-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Green hosts | | |
| Arylcarbazoles | | Appl. Phys. Lett. 78, 1622 (2001) |

TABLE 1-continued
| MATERIAL | EXAMPLES OF MATERIAL | PUBLICATIONS |
|---|---|---|
| | 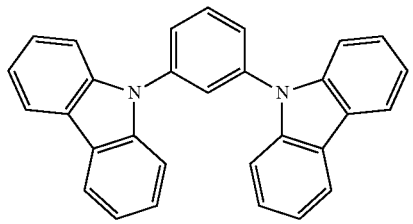 [SMILES: c1cc(-n2c3ccccc3c3ccccc32)cc(-n2c3ccccc3c3ccccc32)c1] | US20030175553 |
| | 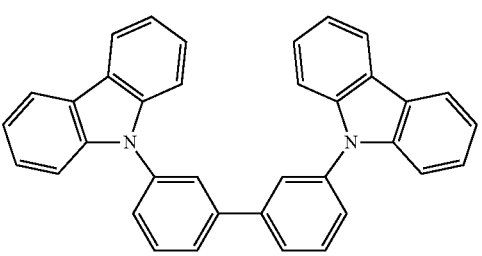 [SMILES: c1cc(-c2cccc(-n3c4ccccc4c4ccccc43)c2)cc(-n2c3ccccc3c3ccccc32)c1] | WO2001039234 |
| Aryltriphenylene compounds | 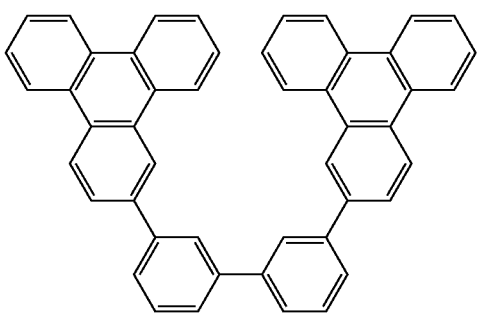 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 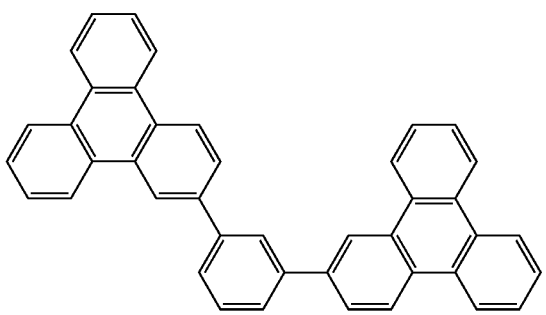 [SMILES: c1cc(-c2ccc3c4ccccc4c4ccccc4c3c2)cc(-c2ccc3c4ccccc4c4ccccc4c3c2)c1] | US20060280965 |
| | 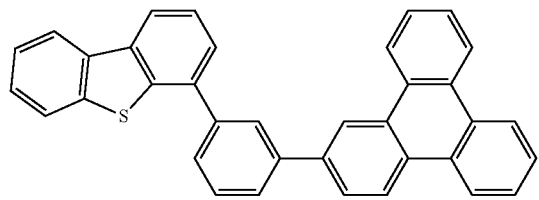 [SMILES: c1cc(-c2ccc3c4ccccc4c4ccccc4c3c2)cc(-c2cccc3c2sc2ccccc23)c1] | WO2009021126 |

TABLE 1-continued
| MATERIAL | EXAMPLES OF MATERIAL | PUBLICATIONS |
|---|---|---|
| Poly-fused heteroaryl compounds | 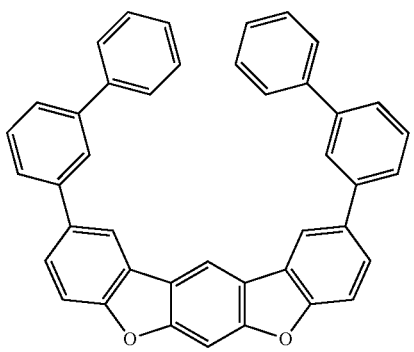 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 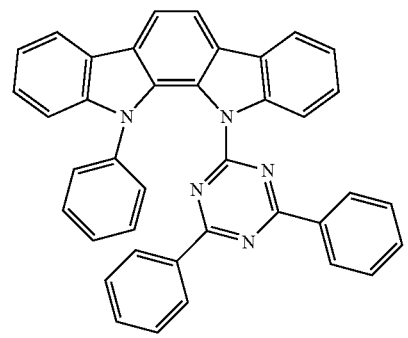 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 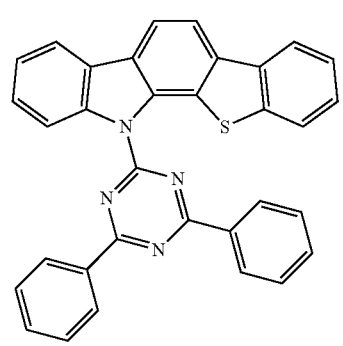 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 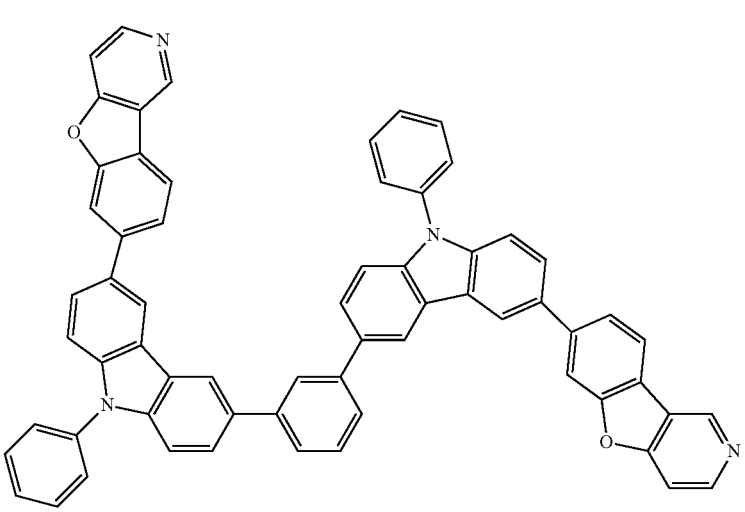 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

| MATERIAL | EXAMPLES OF MATERIAL | PUBLICATIONS |
|---|---|---|
| | 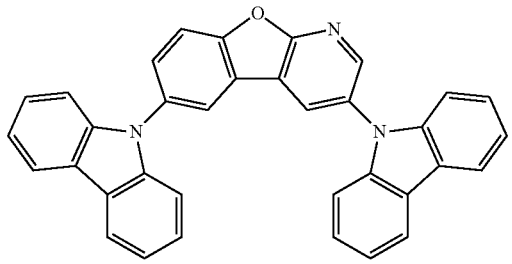 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 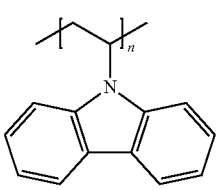 | Appl. Phys. Lett. 77, 2280 (2000) |
| Spirofluorene compounds | 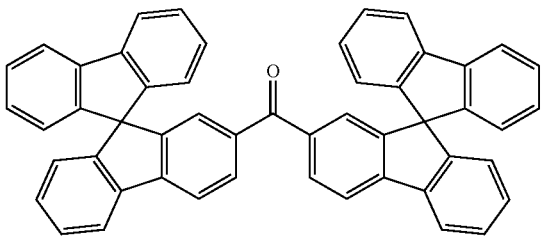 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 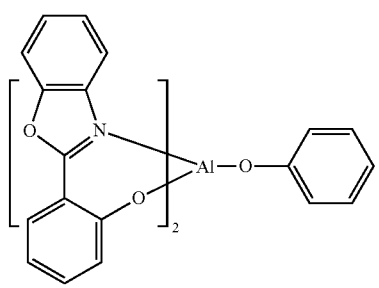 | WO2005089025 |
| | 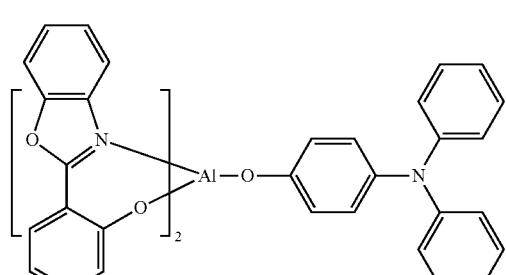 | WO2006132173 |
| | 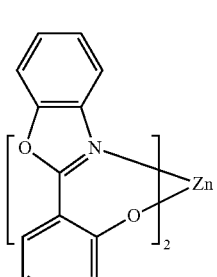 | JP200511610 |

TABLE 1-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |

TABLE 1-continued
| MATERIAL | EXAMPLES OF MATERIAL | PUBLICATIONS |
|---|---|---|
| | 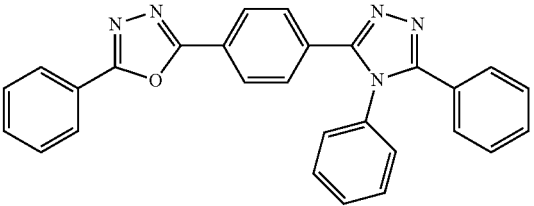 [SMILES: c1ccc(-c2nnc(-c3ccc(-c4nnc(-c5ccccc5)n4-c4ccccc4)cc3)o2)cc1] | WO2004107822 |
| Tetraphenylene complexes | 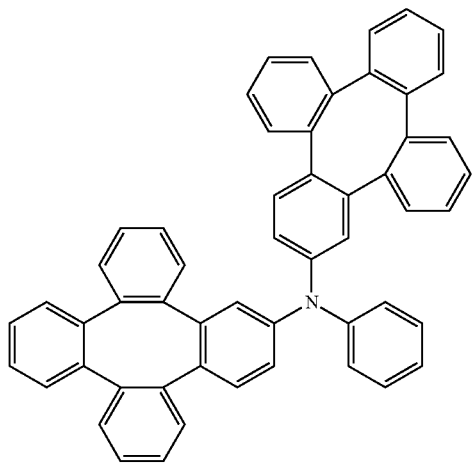 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 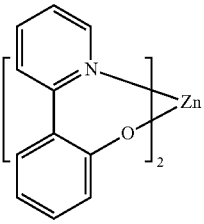 | WO2005030900 |
| Metal coordination complexes (e.g., Zn, Al with N^N ligands) | 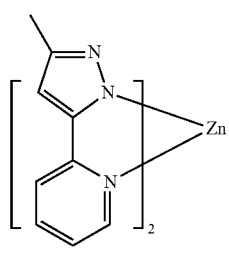 | US20040137268, US20040137267 |
| Blue hosts | | |
| Arylcarbazoles | 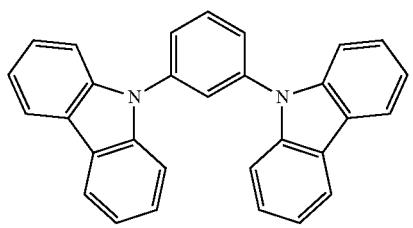 [SMILES: c1cc(-n2c3ccccc3c3ccccc32)cc(-n2c3ccccc3c3ccccc32)c1] | Appl. Phys. Lett, 82, 2422 (2003) |

TABLE 1-continued

| MATERIAL | EXAMPLES OF MATERIAL | PUBLICATIONS |
|---|---|---|
| | | US20070190359 |
| Dibenzothiophene/ Dibenzofuran-carbazole compounds | | WO2006114966, US20090167162 |
| | | US20090167162 |
| | | WO2009086028 |
| | | US20090030202, US20090017330 |
| | | US20100084966 |

TABLE 1-continued
| MATERIAL | EXAMPLES OF MATERIAL | PUBLICATIONS |
|---|---|---|
| Silicon aryl compounds | 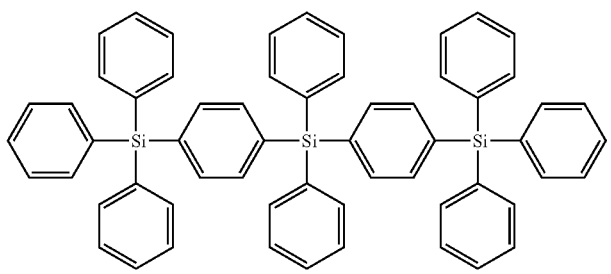 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 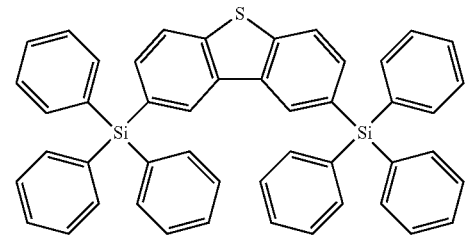 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 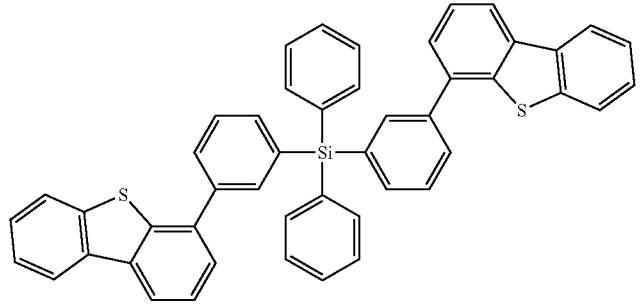 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 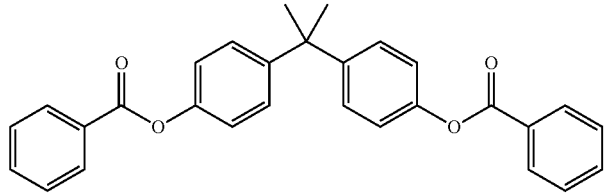 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 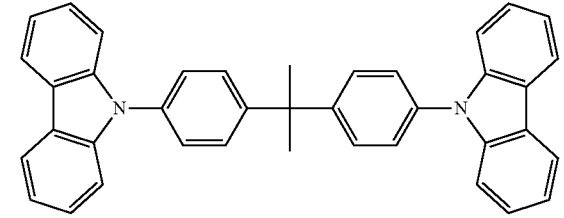 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 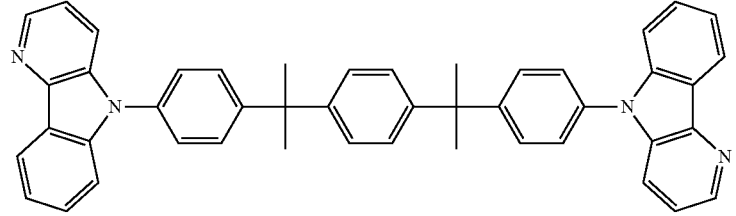 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 1-continued

| MATERIAL | EXAMPLES OF MATERIAL | PUBLICATIONS |
|---|---|---|
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 1-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

TABLE 1-continued

| MATERIAL | EXAMPLES OF MATERIAL | PUBLICATIONS |
|---|---|---|
| | | Adv. Mater. 19, 739 (2007) |
| | | WO2009100991 |
| | | WO2008101842 |
| | | U.S. Pat. No. 7,232,618 |
| Platinum(II) organometallic complexes | | WO2003040257 |

TABLE 1-continued
| MATERIAL | EXAMPLES OF MATERIAL | PUBLICATIONS |
|---|---|---|
| | 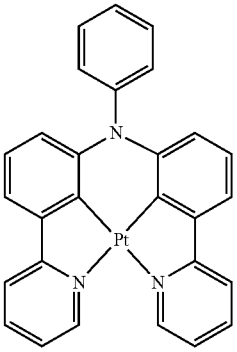 | US20070103060 |
| Osmium(III) complexes | 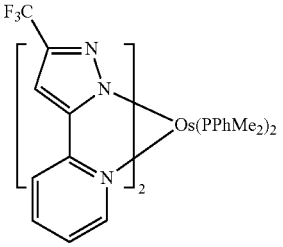 | Chem. Mater. 17, 3532 (2005) |
| Ruthenium(II) complexes | 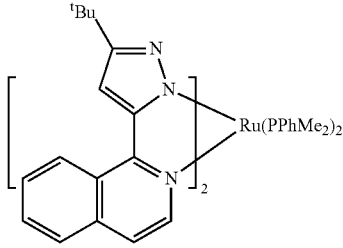 | Adv. Mater. 17, 1059 (2005) |
| Rhenium (I), (II), and (III) complexes | 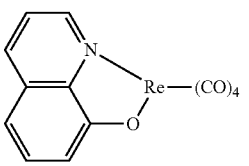 | US20050244673 |
Green dopants
| Iridium(III) organometallic complexes | 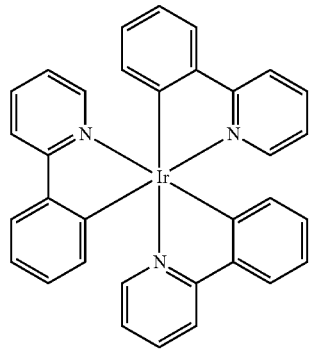 | Inorg. Chem. 40, 1704 (2001) |
|---|---|---|
| | and its derivatives | |

TABLE 1-continued
| MATERIAL | EXAMPLES OF MATERIAL | PUBLICATIONS |
|---|---|---|
| | 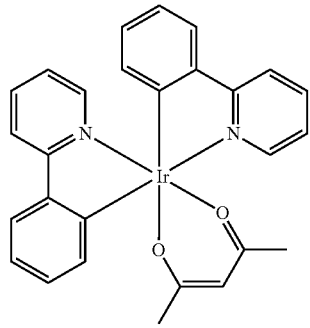 | US20020034656 |
| | 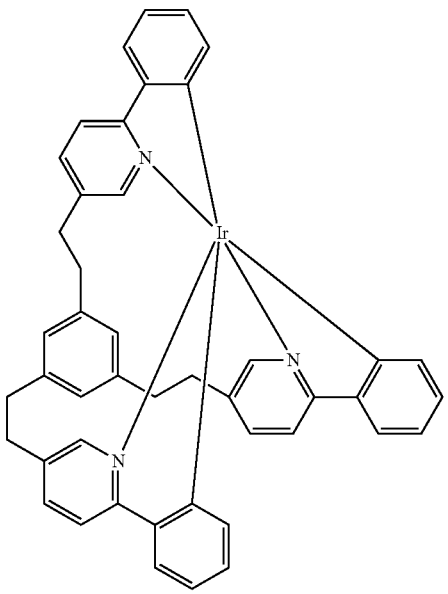 | U.S. Pat. No. 7,332,232 |
| | 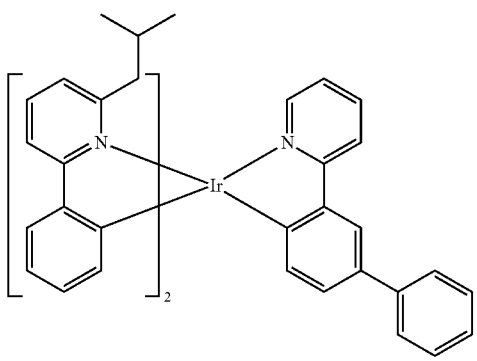 | US20090108737 |

TABLE 1-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE 1-continued
| MATERIAL | EXAMPLES OF MATERIAL | PUBLICATIONS |
|---|---|---|
| | 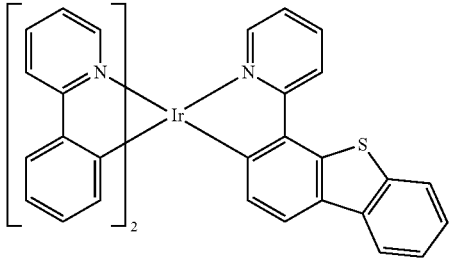 | US20100244004 |
| | 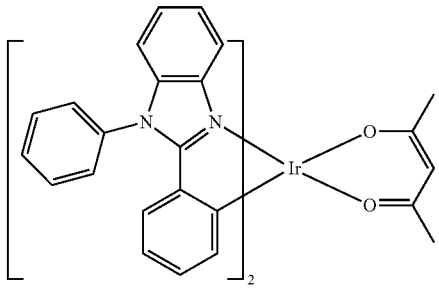 | U.S. Pat. No. 6,687,266 |
| | 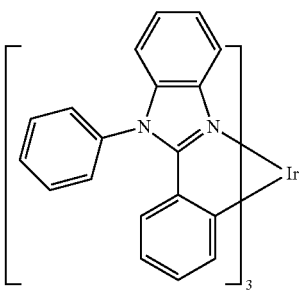 | Chem. Mater. 16, 2480 (2004) |
| | 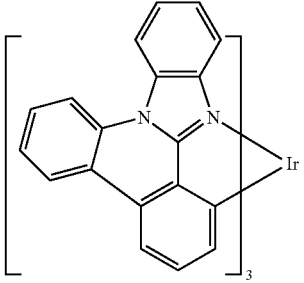 | US20070190359 |
| | 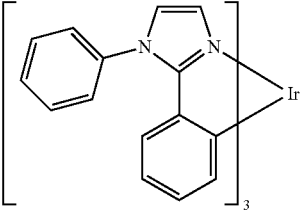 | US 20060008670 JP2007123392 |
| | 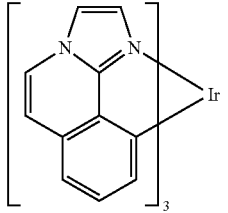 | WO2010086089, WO2011044988 |

TABLE 1-continued
| MATERIAL | EXAMPLES OF MATERIAL | PUBLICATIONS |
|---|---|---|
|  | 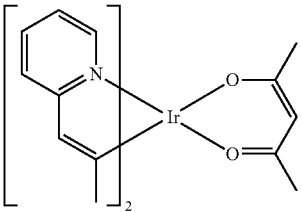 | Adv. Mater. 16, 2003 (2004) |
|  | 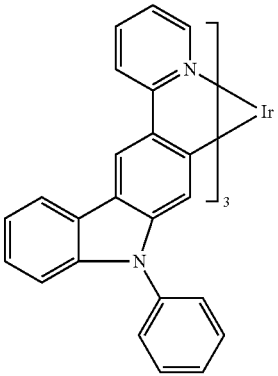 | Angew. Chem. Int. Ed. 2006, 45, 7800 |
|  | 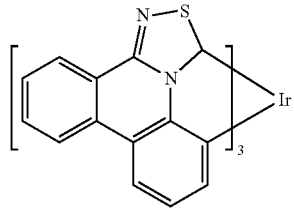 | WO2009050290 |
|  | 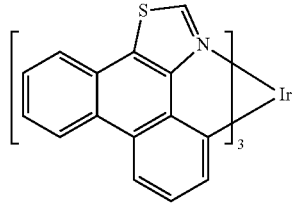 | US20090165846 |
|  | 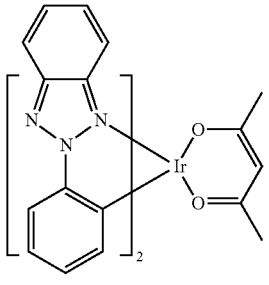 | US20080015355 |
|  | 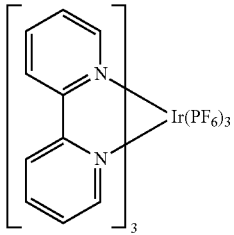 | US20010015432 |

TABLE 1-continued

| MATERIAL | EXAMPLES OF MATERIAL | PUBLICATIONS |
| --- | --- | --- |
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |

| MATERIAL | EXAMPLES OF MATERIAL | PUBLICATIONS |
|---|---|---|
| | 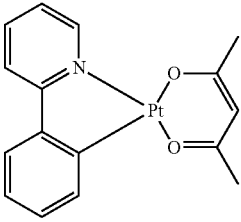 | WO2002015645 |
| | 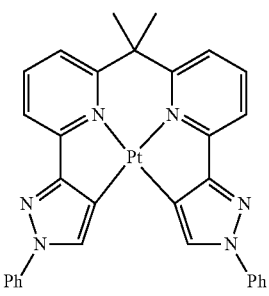 | US20060263635 |
| | 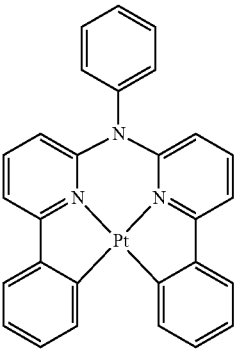 | US20060182992<br>US20070103060 |
| Cu complexes | 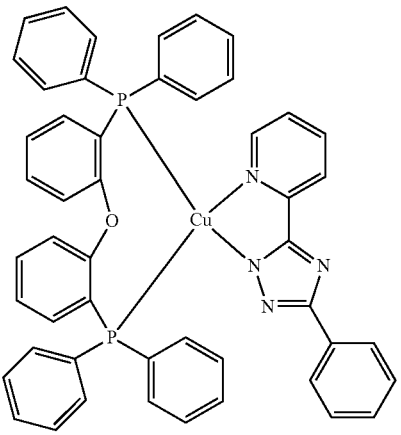 | WO2009000673 |

TABLE 1-continued
| MATERIAL | EXAMPLES OF MATERIAL | PUBLICATIONS |
|---|---|---|
|  | 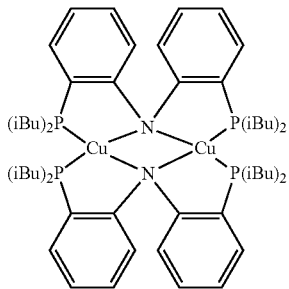 | US20070111026 |
| Gold complexes | 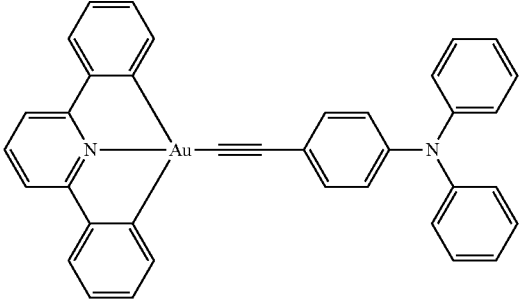 | Chem. Commun. 2906 (2005) |
| Rhenium(III) complexes | 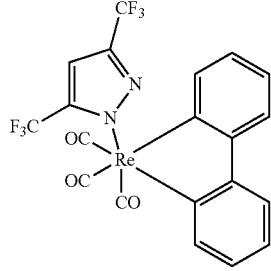 | Inorg. Chem. 42, 1248 (2003) |
| Osmium(II) complexes | 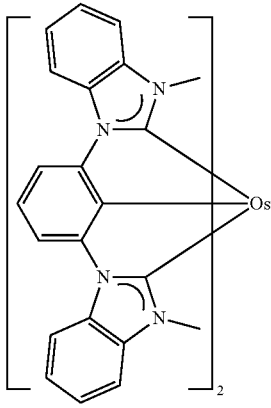 | U.S. Pat. No. 7,279,704 |

TABLE 1-continued

| MATERIAL | EXAMPLES OF MATERIAL | PUBLICATIONS |
| --- | --- | --- |
| Deuterated organometallic complexes | | US20030138657 |
| Organometallic complexes with two or more metal centers | | US20030152802 |
| | | U.S. Pat. No. 7,090,928 |

Blue dopants

| | | |
| --- | --- | --- |
| Iridium(III) organometallic complexes | | WO2002002714 |
| | | WO2006009024 |

TABLE 1-continued

| MATERIAL | EXAMPLES OF MATERIAL | PUBLICATIONS |
|---|---|---|
| | | US20060251923 US20110057559 US20110204333 |
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |

TABLE 1-continued

| MATERIAL | EXAMPLES OF MATERIAL | PUBLICATIONS |
|---|---|---|
| | | US20070190359, US20080297033 US20100148663 |
| | | U.S. Pat. No. 7,338,722 |
| | | US20020134984 |
| | | Angew. Chem. Int. Ed. 47, 4542 (2008) |
| | | Chem. Mater. 18, 5119 (2006) |

TABLE 1-continued
| MATERIAL | EXAMPLES OF MATERIAL | PUBLICATIONS |
|---|---|---|
| | 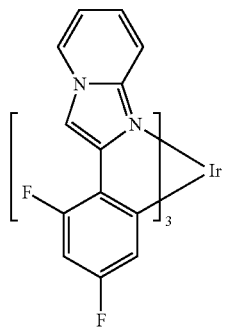 | Inorg. Chem. 46, 4308 (2007) |
| | 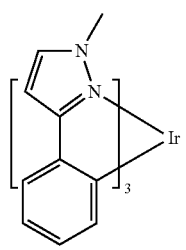 | WO2005123873 |
| | 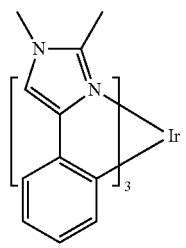 | WO2005123873 |
| | 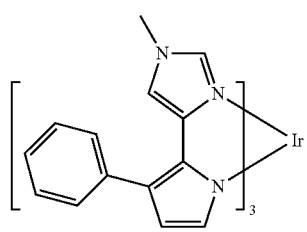 | WO2007004380 |
| | 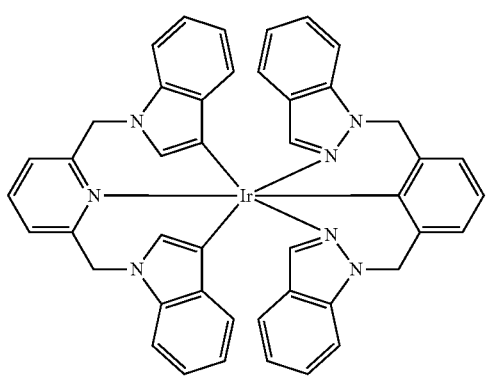 | WO2006082742 |

| MATERIAL | EXAMPLES OF MATERIAL | PUBLICATIONS |
|---|---|---|
| Osmium(II) complexes | 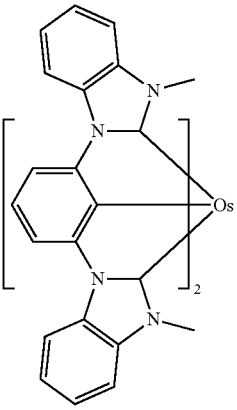 | U.S. Pat. No. 7,279,704 |
| | 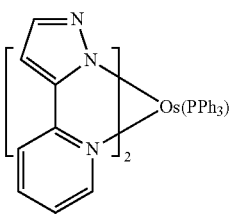 | Organometallics 23, 3745 (2004) |
| Gold complexes | 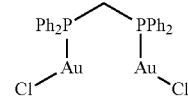 | Appl. Phys. Lett. 74, 1361 (1999) |
| Platinum(II) complexes | 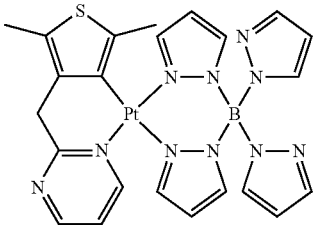 | WO2006098120, WO2006103874 |
| Pt tetradentate complexes with at least one metal-carbene bond | 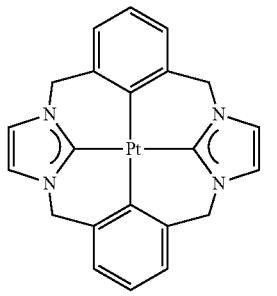 | U.S. Pat. No. 7,655,323 |
| Exciton/hole blocking layer materials | | |
| Bathocuprine compounds (e.g., BCP, BPhen) | 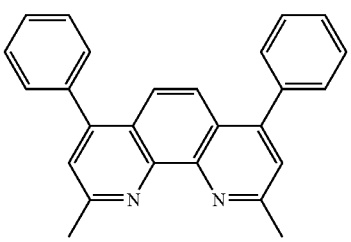 [SMILES: Cc1cc(-c2ccccc2)c2ccc3c(-c4ccccc4)cc(C)nc3c2n1] | Appl. Phys. Lett. 75, 4 (1999) |

TABLE 1-continued
| MATERIAL | EXAMPLES OF MATERIAL | PUBLICATIONS |
|---|---|---|
| | 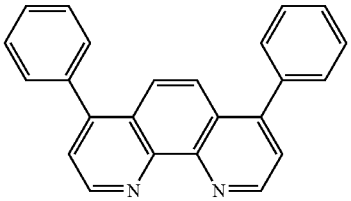 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 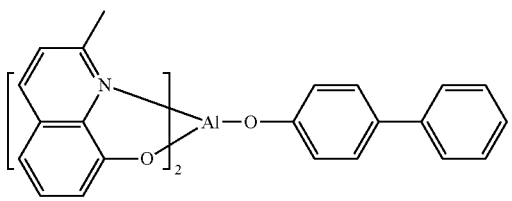 | Appl. Phys. Lett. 81, 162 (2002) |
| 5-member ring electron deficient heterocycles such as triazole, oxadiazole, imidazole, benzoimidazole | 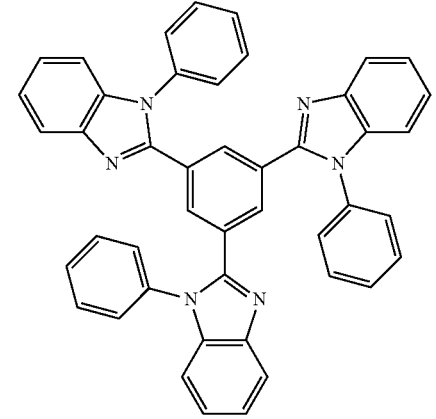 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 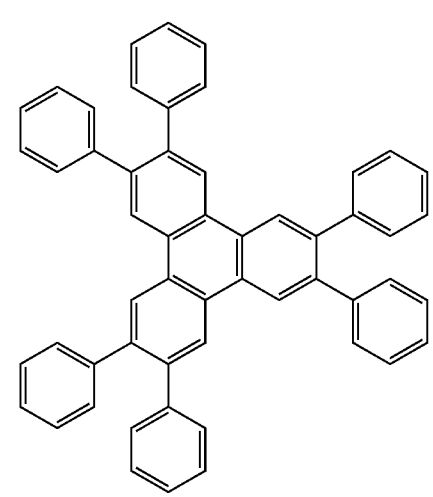 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
|---|---|---|
| Fluorinated aromatic compounds | 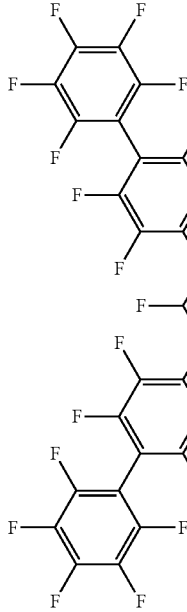 | Appl. Phys. Lett. 79, 156 (2001) |
| Phenothiazine-S-oxide | 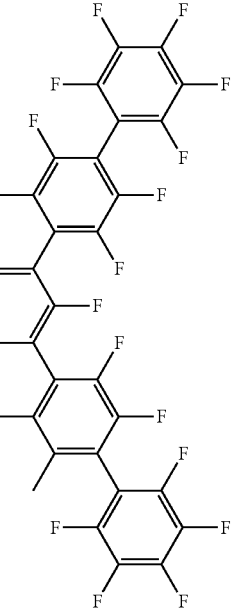 | WO2008132085 |
| Silylated five-membered nitrogen, oxygen, sulfur or phosphorus dibenzoheterocycles | 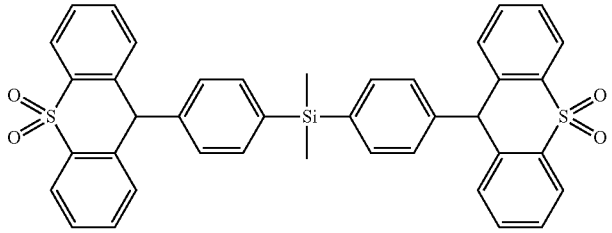 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2010079051 |
| Aza-carbazoles | 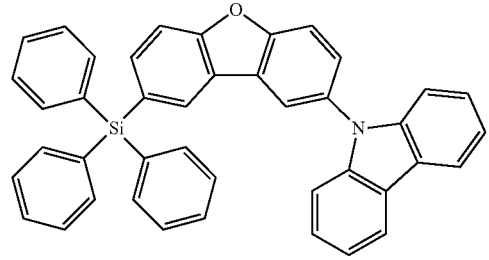 [SMILES: c1ccc([Si](c2ccccc2)(c2ccccc2)c2ccc3oc4ccc(-n5c6ccccc6c6ccccc65)cc4c3c2)cc1] | US20060121308 |
Electron transporting materials TABLE 1-continued

| MATERIAL | EXAMPLES OF MATERIAL | PUBLICATIONS |
| --- | --- | --- |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) U.S. Pat. No. 7,230,107 |

TABLE 1-continued

| MATERIAL | EXAMPLES OF MATERIAL | PUBLICATIONS |
| --- | --- | --- |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 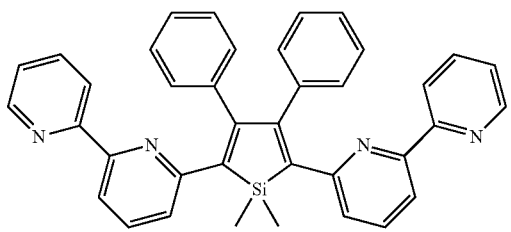 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 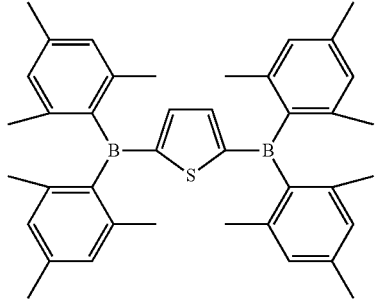 | J. Am. Chem. Soc. 120, 9714 (1998) |
| Fluorinated aromatic compounds | 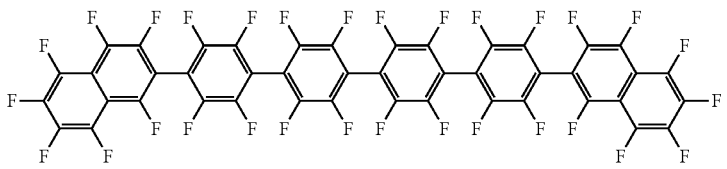 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 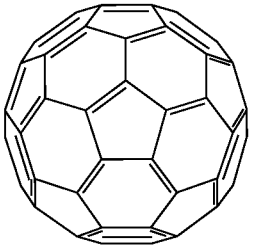 | US20090101870 |
| Triazine complexes | 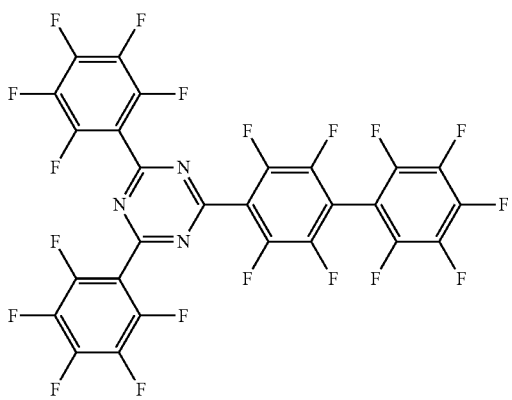 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 1-continued

| MATERIAL | EXAMPLES OF MATERIAL | PUBLICATIONS |
| --- | --- | --- |
| Zn (N^N) complexes | 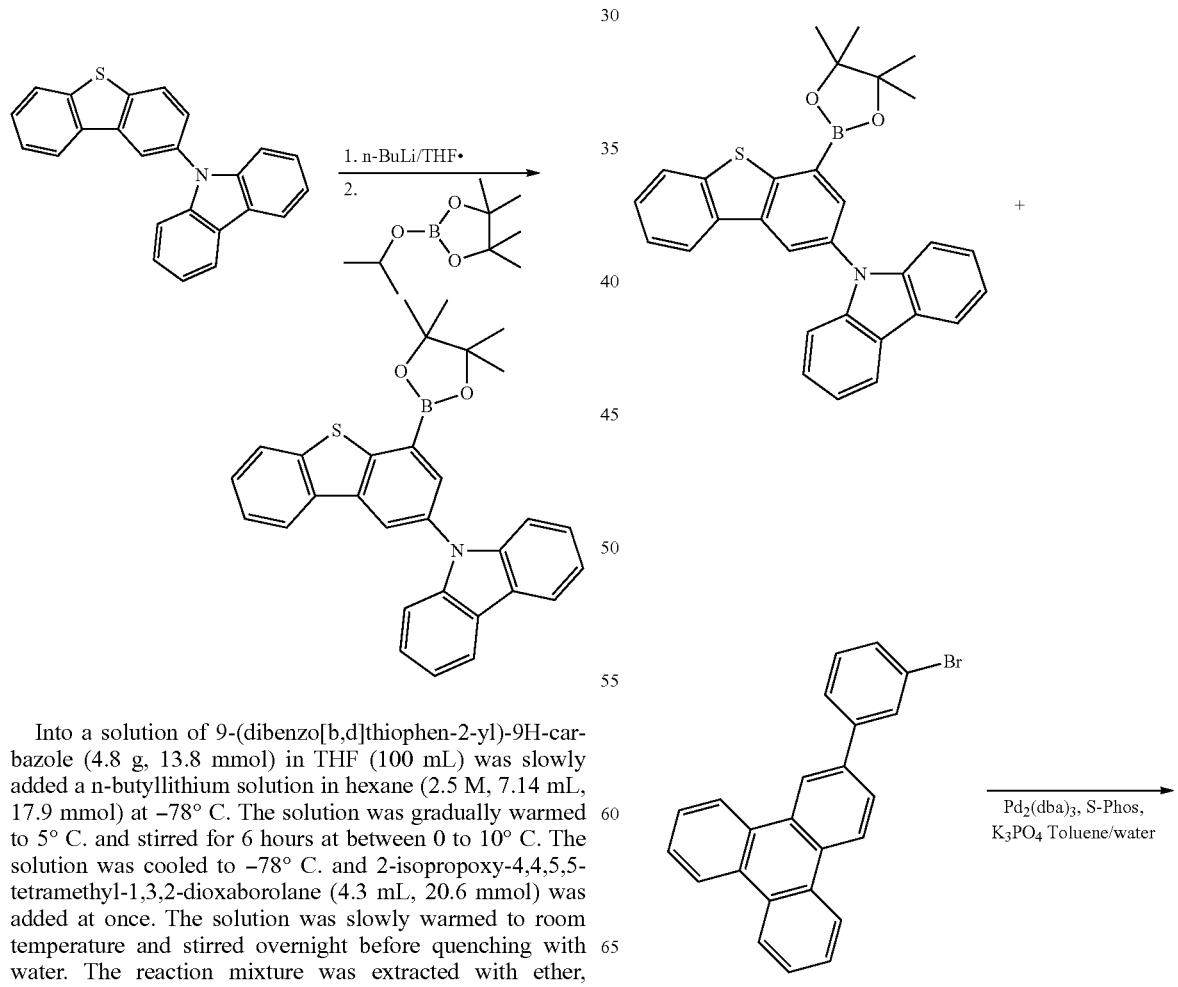 | U.S. Pat. No. 6,528,187 |

EXPERIMENTAL

Chemical abbreviations used throughout this document are as follows: S-Phos is dicyclohexyl(2',6'-dimethoxy-[1,1'-biphenyl]-2-yl)phosphine, $Pd_2(dba)_3$ is tri(dibenzylideneacetone) dipalladium(0), THF is tetrahydrofuran, and DCM is dichloromethane.

Example 1

Synthesis of Compound 43-S

Into a solution of 9-(dibenzo[b,d]thiophen-2-yl)-9H-carbazole (4.8 g, 13.8 mmol) in THF (100 mL) was slowly added a n-butyllithium solution in hexane (2.5 M, 7.14 mL, 17.9 mmol) at −78° C. The solution was gradually warmed to 5° C. and stirred for 6 hours at between 0 to 10° C. The solution was cooled to −78° C. and 2-isopropoxy-4,4,5,5-tetramethyl-1,3,2-dioxaborolane (4.3 mL, 20.6 mmol) was added at once. The solution was slowly warmed to room temperature and stirred overnight before quenching with water. The reaction mixture was extracted with ether, washed with brine and water, dried over $MgSO_4$, and the solvent was evaporated. The residue was purified by column chromatography on silica gel with heptane/DCM as eluent and trituration with heptane to yield 9-(4-(4,4,5,5-tetramethyl-1,3,2-dioxaborolan-2-yl)dibenzo[b,d]thiophen-2-yl)-9H-carbazole (3.8 g, 57%) as a white powder.

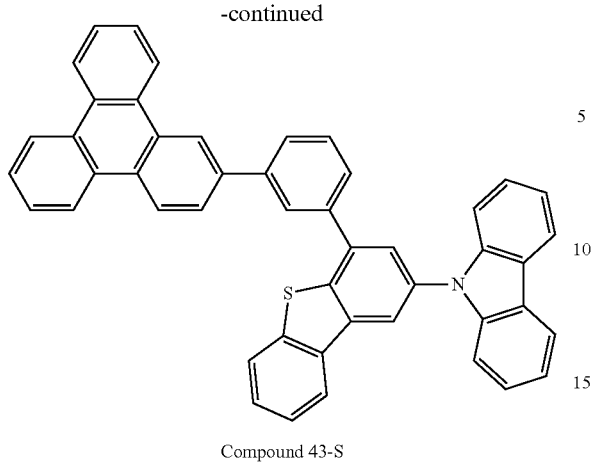

Compound 43-S

A solution of 9-(4-(4,4,5,5-tetramethyl-1,3,2-dioxaborolan-2-yl)dibenzo[b,d]thiophen-2-yl)-9H-carbazole (3.0 g, 6.3 mmol), 2-(3-bromophenyl)triphenylene (2.4 g, 6.31 mmol), Pd$_2$(dba)$_3$ (0.116 g, 0.126 mmol), S-Phos (0.104 g, 0.252 mmol), and K$_3$PO$_4$ (4.02 g, 18.93 mmol) in toluene (100 mL) and water (15 mL) was refluxed under nitrogen at 110° C. for 3 hour. After cooling to room temperature, the solution was diluted with water and the solid was collected by filtration. The crude product was redissolved in boiling toluene (800 mL) and filtered through a short plug of silica gel topped with a layer of anhydrous MgSO$_4$. The filtrate was concentrated and the white solid was collected and triturated with boiling xylene and dichloromethane successively to yield Compound 43-S (3.5 g, 85%) as a white solid.

Example 2

Synthesis of Compound 17-S

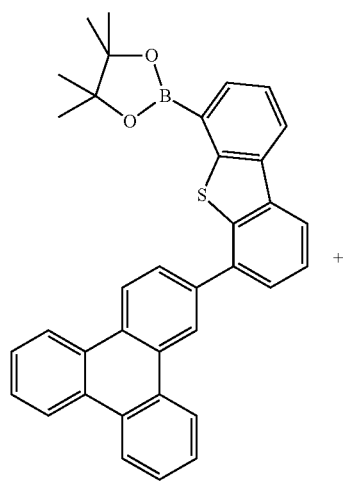

+

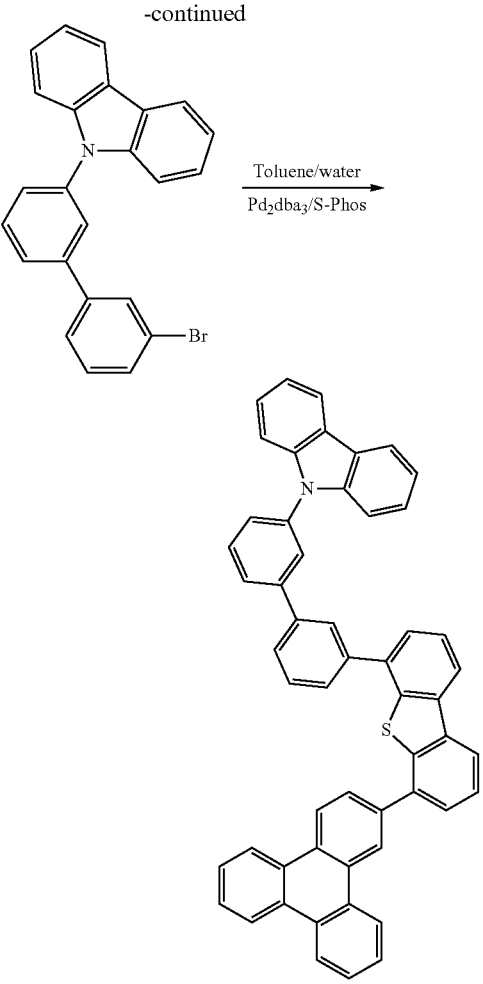

Compound 17-S

A mixture of 4,4,5,5-tetramethyl-2-(6-(triphenylen-2-yl)dibenzo[b,d]thiophen-4-yl)-1,3,2-dioxaborolane (2.7 g, 5.03 mmol), 9-(3'-bromo-[1,1'-biphenyl]-3-yl)-9H-carbazole (2.065 g, 5.18 mmol), tris(dibenzylideneacetone)palladium (0) (0.138 g, 0.151 mmol), and 2-dicyclohexylphosphino-2',6'-dimethoxybiphenyl (0.310 g, 0.755 mmol) was charged into 250 mL of toluene. Potassium phosphate tribasic monohydrate (3.47 g, 15.10 mmol) was dissolved in 25 mL of water and the solution was charged into the reaction mixture. The reaction mixture was degassed with nitrogen then was heated at reflux overnight. The reaction mixture was cooled to room temperature. The toluene layer was separated and dried under vacuum. The crude residue was passed through a silica gel column using 35-99% toluene/hexanes. The cleanest product fractions were combined and concentrated under vacuum. The cleanest fractions were recrystallized from toluene. 9-(3'-(6-(triphenylen-2-yl)dibenzo[b,d]thiophen-4-yl)-[1,1'-biphenyl]-3-yl)-9H-carbazole (Compound 17-S) (1.832 g, 2.52 mmol, 50% yield) was isolated as a white solid.

Example 3

Synthesis of Compound 7-S

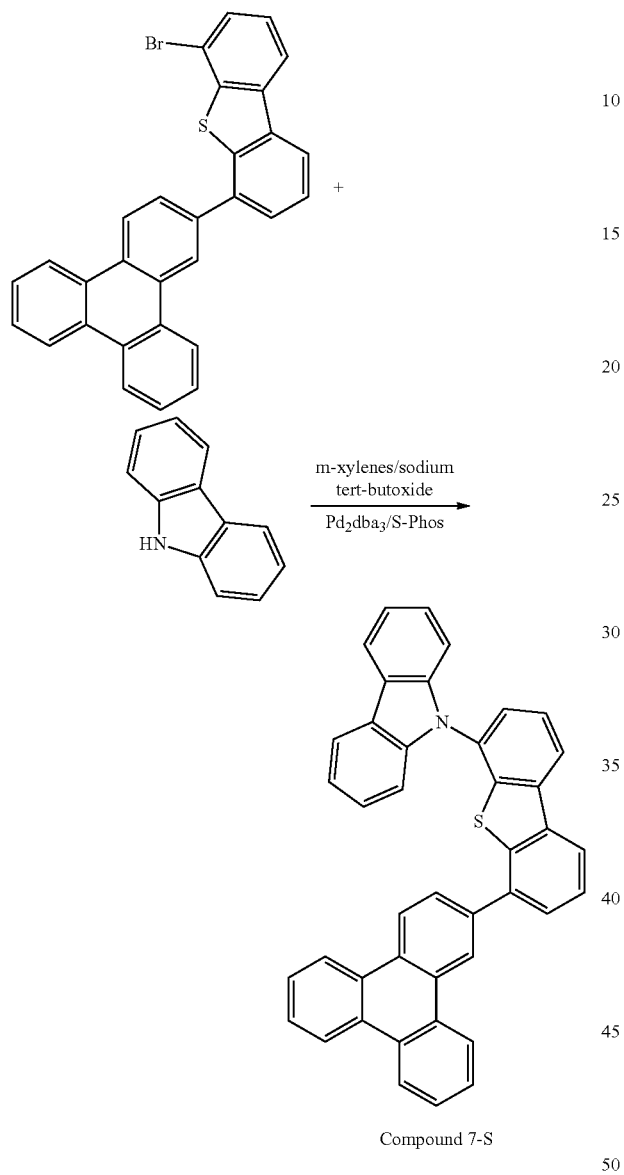

Compound 7-S 4-bromo-6-(triphenylen-2-yl)dibenzo[b,d]thiophene (5 g, 10.22 mmol), 9H-carbazole (1.999 g, 11.95 mmol), sodium tert-butoxide (1.964 g, 20.43 mmol), tris(dibenzylideneacetone)palladium(0) (0.280 g, 0.306 mmol), and 2-dicyclohexylphosphino-2',6'-dimethoxybiphenyl (0.628 g, 1.532 mmol) were charged into a 3-neck flask with 300 mL of m-xylenes. The reaction mixture was degassed using nitrogen. The reaction was then heated to reflux for 24 hours. The reaction mixture was cooled to room temperature and was diluted with 100 mL of water. The mixture was passed through a pad of celite. The organic layer was separated and was dried over magnesium sulfate. The mixture was filtered and concentrated under vacuum. The crude residue was passed through a silica gel column using 35-50% toluene/hexanes. The cleanest fractions were combined and concentrated under vacuum. The cleanest fractions were triturated with hot ethanol to remove excess carbazole. The solid was then triturated with hot heptanes/toluene. A white solid was collected via filtration and was recrystallized from toluene. 9-(6-(triphenylen-2-yl)dibenzo[b,d]thiophen-4-yl)-9H-carbazole (Compound 7-S) (3.04 g, 5.28 mmol, 51.7% yield) was isolated as a white solid.

Example 4

Synthesis of Compound 11-S

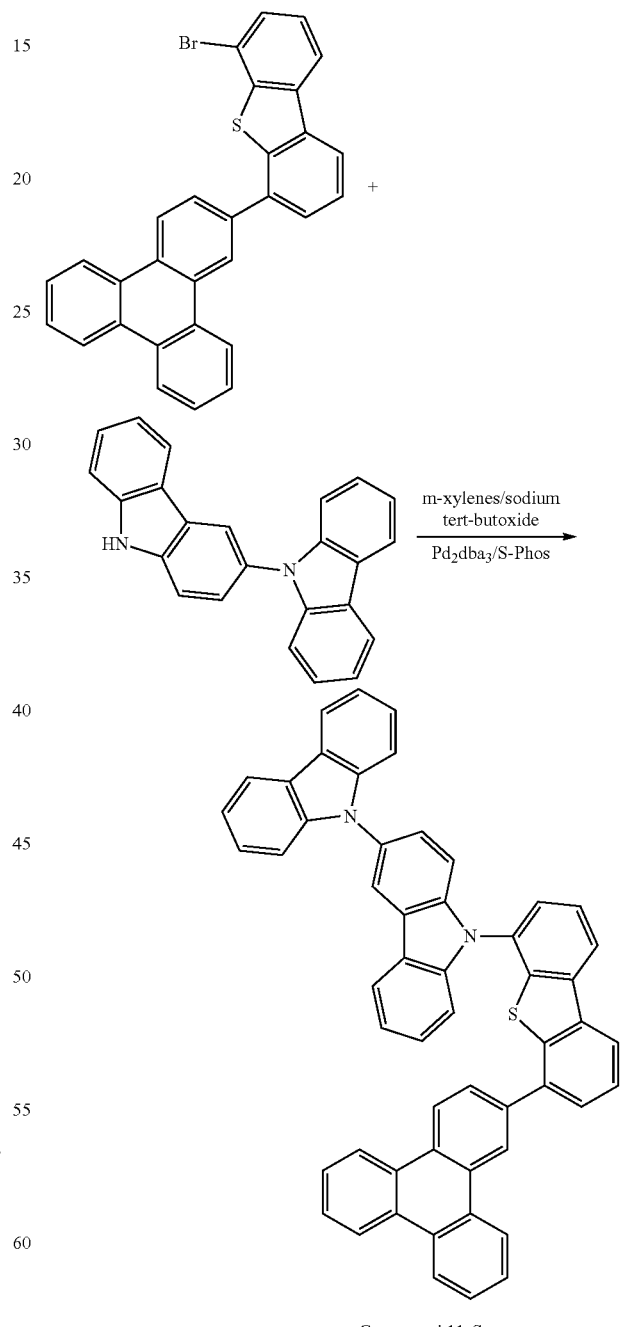

Compound 11-S 9H-3,9'-bicarbazole (1.88 g, 5.66 mmol), sodium tert-butoxide (1 g, 10.42 mmol), tris(dibenzylideneacetone)palladium(0) (0.22 g, 0.240 mmol), and 2-dicyclohexylphosphino-2',6'-dimethoxybiphenyl (0.5 g, 1.220 mmol) were charged into a reaction flask with 210 mL of o-xylenes. The mixture was degassed with nitrogen then was heated to reflux for 2½ days. The reaction mixture was cooled to room temperature. A solid was collected via filtration. The solid was dissolved in 1 L of hot toluene then was passed through a silica gel column. The column was flushed with hot toluene. The toluene filtrate was concentrated under vacuum. The crude solid was triturated with 300 mL of hot ethanol then was filtered under vacuum. The solid collected was then recrystallized twice from hot toluene to yield 9-(6-(triphenylen-2-yl)dibenzo[b,d]thiophen-4-yl)-9H-3,9'-bicarbazole (Compound 11-S) (2.25 g, 3.04 mmol, 59.5% yield) as a white solid.

0.476 mmol) were charged into a reaction flask with 150 mL of toluene. Potassium phosphate tribasic (4.42 g, 20.85 mmol) was dissolved in 15 mL of water then charged into the reaction mixture. The reaction mixture was degassed using nitrogen then was heated at reflux overnight. The reaction mixture was cooled to room temperature. A solid was collected via filtration. This solid was triturated with 300 mL of warm methanol. The solid was filtered and dried under vacuum. This solid was then dissolved in 800 mL of refluxing toluene then was passed through a pad of silica gel. The filtrate was concentrated under vacuum then was recrystallized twice from toluene. 9-(3-(6-(triphenylen-2-yl)dibenzo[b,d]furan-4-yl)phenyl)-9H-carbazole (Compound4-O) (1.75 g, 2.75 mmol, 47.8% yield) was isolated as a white solid.

Example 5

Synthesis of Compound 4-O

Example 6

Synthesis of Compound 4-S

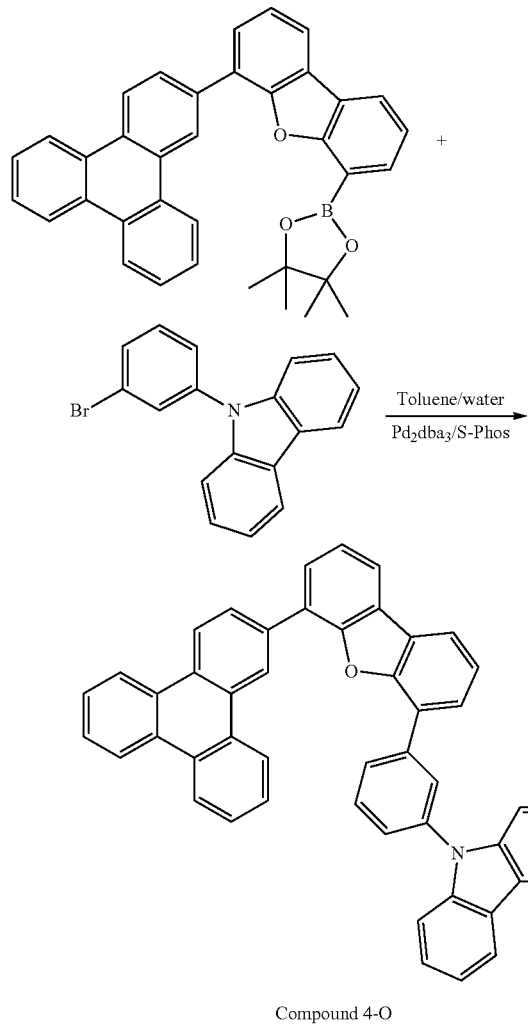

Compound 4-O

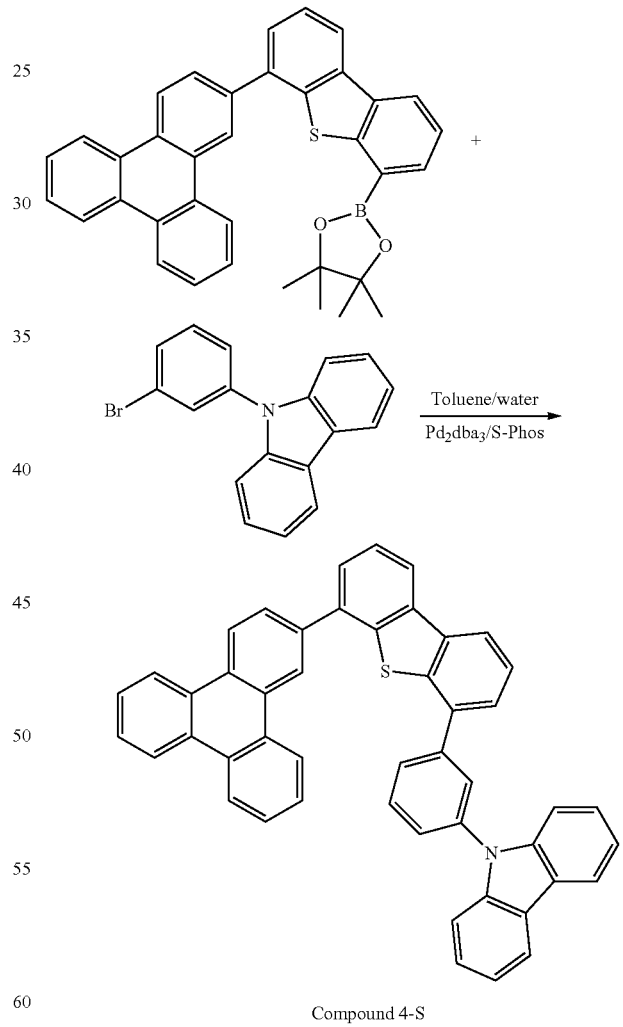

Compound 4-S 4,4,5,5-tetramethyl-2-(6-(triphenylen-2-yl)dibenzo[b,d]furan-4-yl)-1,3,2-dioxaborolane (3 g, 5.76 mmol), 9-(3-bromophenyl)-9H-carbazole (2 g, 6.21 mmol), tris(dibenzylideneacetone)palladium(0) (0.109 g, 0.119 mmol), and 2-dicyclohexylphosphino-2',6'-dimethoxybiphenyl (0.195 g, 4,4,5,5-tetramethyl-2-(6-(triphenylen-2-yl)dibenzo[b,d]thiophene-4-yl)-1,3,2-dioxaborolane (2.88 g, 5.37 mmol), 9-(3-bromophenyl)-9H-carbazole (1.78 g, 5.53 mmol), tris(dibenzylideneacetone)palladium(0) (0.098 g, 0.107 mmol), and 2-dicyclohexylphosphino-2',6'-dimethoxybiphenyl (0.176 g, 0.429 mmol) were charged into a reaction flask with 150 mL of toluene. Potassium phosphate tribasic (3.99 g, 18.79 mmol) was dissolved in 15 mL of water then was charged into the reaction mixture. The reaction mixture was degassed using nitrogen then was heated at reflux overnight. The reaction mixture was cooled to room temperature. A solid was collected via filtration and washed with methanol and ethyl acetate. This solid was then dissolved in ~500 mL of refluxing toluene then was passed through a pad of silica gel. The filtrate was concentrated under vacuum then was recrystallized from toluene. 9-(3-(6-(triphenylen-2-yl)dibenzo[b,d]thiophene-4-yl)phenyl)-9H-carbazole (Compound 4-S) (2.6 g, 74.3% yield) was isolated as a white solid.

(0.178 g, 0.435 mmol) were charged into a reaction flask with 120 mL of toluene. Potassium phosphate tribasic (4.04 g, 19.01 mmol) was dissolved in 10 mL of water then was charged into the reaction mixture. The reaction mixture was degassed using nitrogen for 30 minutes then was heated at reflux overnight. The reaction mixture was cooled to room temperature. A solid was collected via filtration. This solid was triturated with 300 mL of warm methanol and washed with ethyl acetate. The solid was filtered and dried under vacuum. This solid was then dissolved in 1200 mL of refluxing toluene then was passed through a pad of silica gel. The filtrate was concentrated under vacuum then was recrystallized from toluene. Compound 1-S (1.1 g, 31.1% yield) was isolated as a white solid.

Example 7

Synthesis of Compound 1-S

Example 8

Synthesis of Compound 20-S

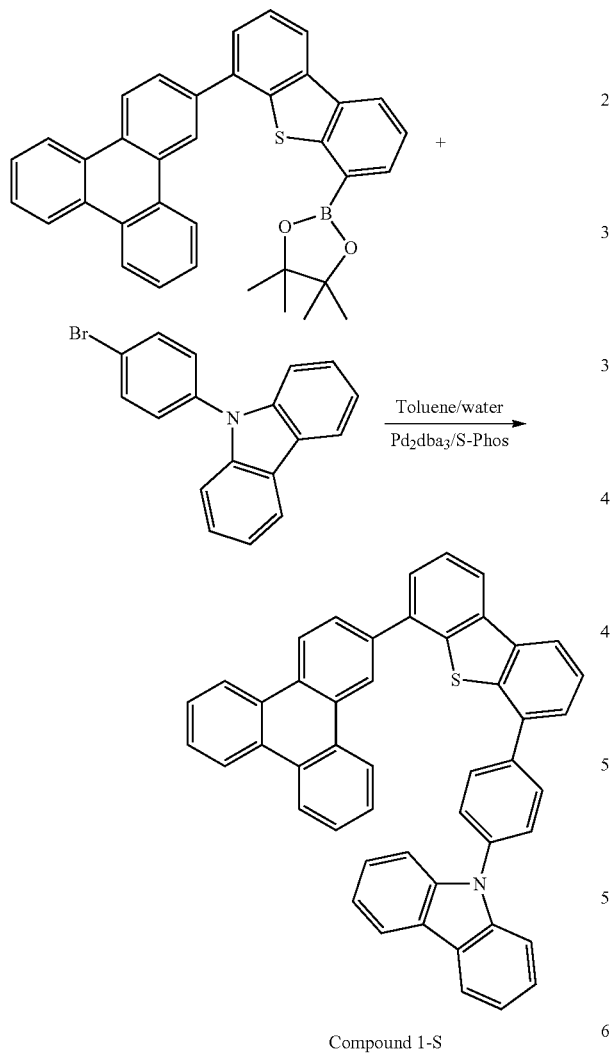

Compound 1-S

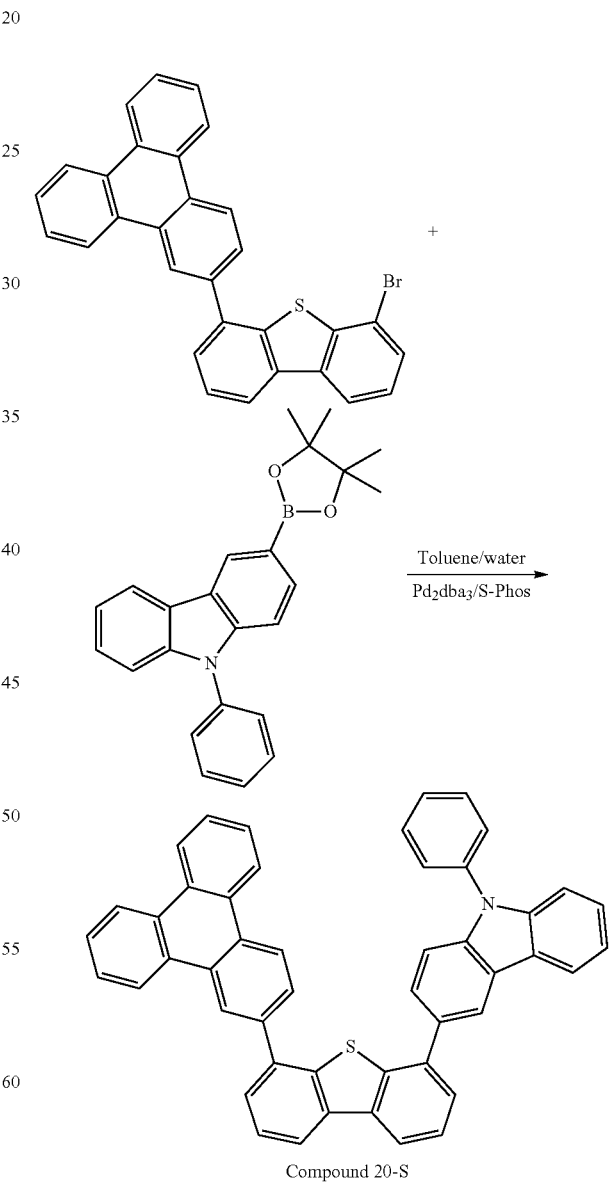

Compound 20-S 4,4,5,5-tetramethyl-2-(6-(triphenylen-2-yl)dibenzo[b,d]thiophene-4-yl)-1,3,2-dioxaborolane (2.94 g, 5.49 mmol), 9-(4-bromophenyl)-9H-carbazole (1.75 g, 5.43 mmol), tris(dibenzylideneacetone)palladium(0) (0.099 g, 0.109 mmol), and 2-dicyclohexylphosphino-2',6'-dimethoxybiphenyl A solution of tris(dibenzylideneacetone) dipalladium(0) (0.142 g, 0.155 mmol), 4-bromo-6-(triphenylen-2-yl)

dibenzo[b,d]thiophene (3.8 g, 7.76 mmol), 9-phenyl-3-(4,4,5,5-tetramethyl-1,3,2-dioxaborolan-2-yl)-9H-carbazole (3.01 g, 8.15 mmol), S-phos (0.255 g, 0.621 mmol), and $K_3PO_4$ (5.77 g, 27.2 mmol) in toluene (200 mL) and water (20 mL) was heated at reflux under $N_2$ for 48 hours. The reaction mixture was cooled to room temperature and diluted with dichloromethane. After washing with water, the organic layer was concentrated. The residual solid was triturated with methanol and then triturated with ethyl acetate. The solid was dissolved in refluxing toluene and filtered while hot through a silica gel plug topped with a layer of magnesium sulfate. The filtrate was concentrated leaving a white solid which was recrystallized from toluene yielding Compound 20-S (2.6 g, 43% yield) of a white solid.

Comparative Device Examples

All comparative device examples were fabricated by high vacuum (<$10^{-7}$ Torr) thermal evaporation. The anode electrode is 1,200 Å of indium tin oxide (ITO). The cathode consisted of 10 Å of LiF followed by 1,000 Å of Aluminum. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound H as the hole injection layer (HIL), 400 Å of 4,4'-bis[N-(1-naphthyl)-N-phenylamino]biphenyl (NPD) as the hole transporting layer (HTL), 300 Å of 15% of Compound B1 as dopant in Compound H1 and Compound H2 as the emissive layer (EML), 400 Å of Alq (tris-8-hydroxyquinoline aluminum) as the electron transport layer (ETL).

As used herein, Compound H, NPD, Alq, Compound B1, Compound H1, and Compound H2 have the following structures:

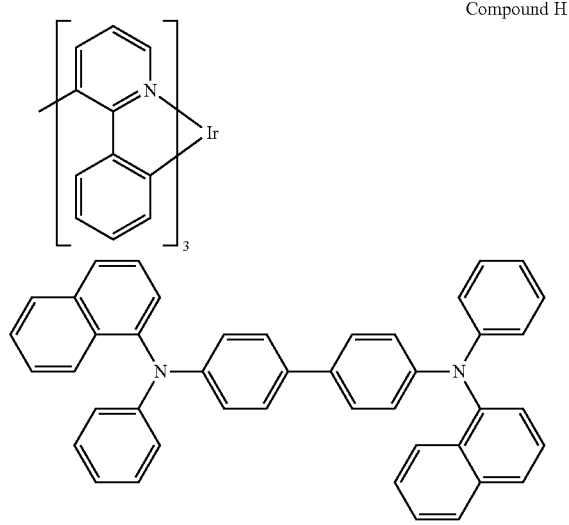

Compound H

NPD

Alq

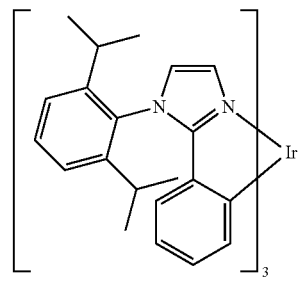

Compound B1

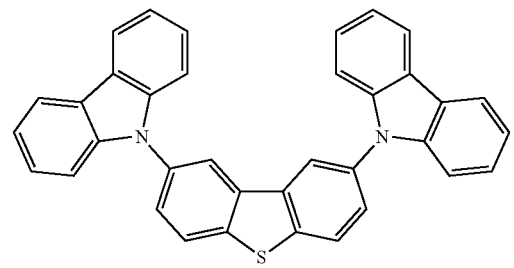

Compound H1

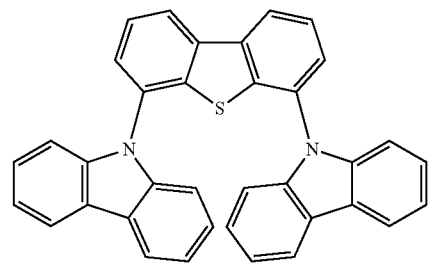

Compound H2

TABLE 2 summarizes the performance of the devices. The lifetime ($LT_{80\%}$) was defined as the time required for the device to decay to 80% of its initial luminance ($L_0$) of 2000 nits. Devices comprising Compounds H1 and H2 showed the same device lifetime, which indicates that the carbazole substitution position on dibenzothiophene does not affect device performance. Therefore, comparative devices examples using Compound C below as the host should give valid device results comparison.

TABLE 2

Device structures and results

| Example | EML (300 Å, doping %) | | CIE (x, y) | $LT_{80\%}$ (h) |
|---|---|---|---|---|
| Example 1 | Compound H1 | Compound B1 15% | (0.174, 0.370) | 167 |
| Example 2 | Compound H2 | Compound B1 15% | (0.176, 0.375) | 170 |

Device Examples

Device examples were fabricated by high vacuum (<$10^{-7}$ Torr) thermal evaporation. The anode electrode was 1,200 Å of indium tin oxide (ITO). The cathode consisted of 10 Å of LiF followed by 1,000 Å of Aluminum. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound A as the hole injection layer (HIL), 300 Å of 4,4'-bis[N-(1-naphthyl)-N-phenylamino]biphenyl (NPD) as the hole transporting layer (HTL), 300 Å of the invention compounds doped with Compound A as dopant with 10 weight percent of the iridium phosphorescent compound as the emissive layer (EML), 50 Å of compound BL as a blocking layer (BL), 450 Å of Alq (tris-8-hydroxyquinoline aluminum) as the electron transport layer (ETL). The comparative example with Compound C was fabricated similarly to the Device Examples except that in the Device Examples 1, 2, and 3, Compounds 4-S, 7-S, and 11-S, respectively, were used as the host in the EML.

The device structures are provided in TABLE 3. As used herein, Compound A, Compound C, NPD, Compound BL, and Alq have the following structures:

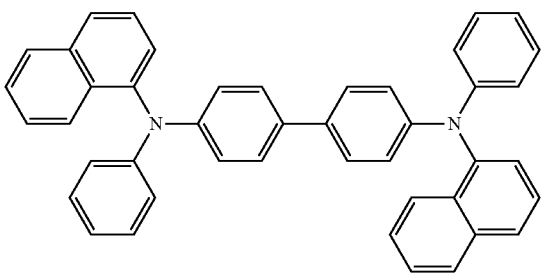

NPD

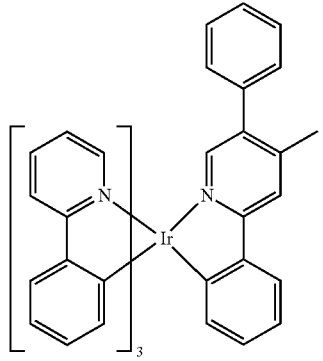

Compound A

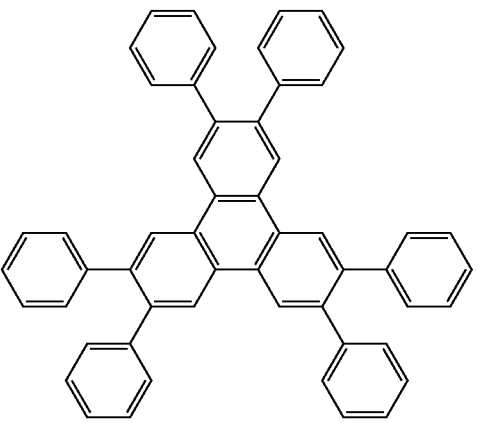

Compound BL

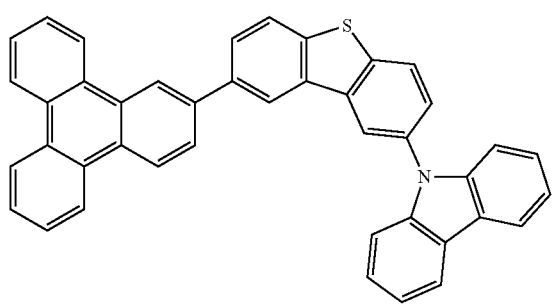

Compound C

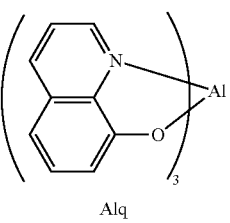

Alq

TABLE 3

Device Structures

| Example | HIL | HTL | EML (300 Å, doping %) | BL | ETL |
| --- | --- | --- | --- | --- | --- |
| Comparative Example 1 | Compound A 100 Å | NPD 300 Å | Compound C 10% | Compound A Compound BL 50 Å | Alq 400 Å |
| Inventive Example 1 | Compound A 100 Å | NPD 300 Å | Compound 7-S 10% | Compound A Compound BL 50 Å | Alq 450 Å |
| Inventive Example 2 | Compound A 100 Å | NPD 300 Å | Compound 4-S 10% | Compound A Compound BL 50 Å | Alq 450 Å |
| Inventive Example 3 | Compound A 100 Å | NPD 300 Å | Compound 11-S 10% | Compound A Compound BL 50 Å | Alq 450 Å |

TABLE 4

VTE Device Results

| | 1931 CIE | | |
| --- | --- | --- | --- |
| | x | y | $LT_{80\%}$ @ 40 mA/cm$^2$ |
| Comparative Example 1 | 0.37 | 0.60 | 100 |
| Inventive Example 1 | 0.37 | 0.60 | 397 |
| Inventive Example 2 | 0.37 | 0.60 | 343 |
| Inventive Example 3 | 0.36 | 0.60 | 147 |

TABLE 4 provides color coordinate and lifetime of the devices. The colors were recorded as green for all examples. The device lifetime $LT_{80}$, which is defined by 20% degradation from the initial luminance, was measured under a constant current density of 40 mA/cm$^2$. The $LT_{80}$ data in TABLE 4 was normalized by the lifetime of Comparative Example 1. As shown in TABLE 4, the $LT_{80}$ of device examples using inventive Compounds 7-S, 4-S, and 11-S, respectively, in the EML layer, are 297%, 243%, and 47% longer than the device example using comparative Compound C in the EML layer of the device.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having formula I:

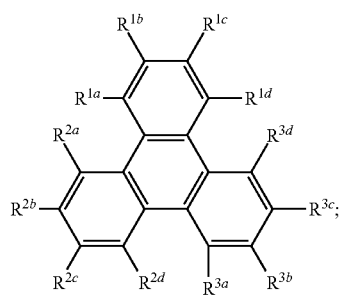

(I)

wherein at least one of $R^{3a}$, $R^{3b}$, $R^{3c}$, or $R^{3d}$ has formula II:

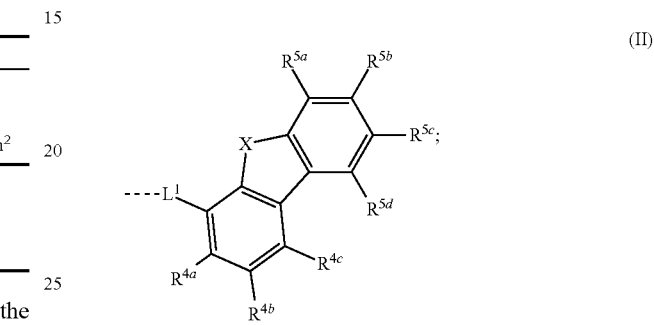

(II)

wherein at least one of $R^{4a}$, $R^{4b}$, $R^{4c}$, $R^{5a}$, $R^{5b}$, $R^{5c}$, or $R^{5d}$ has formula III:

-L$^2$-G    (III);

wherein L$^1$ is a direct bond;
wherein L$^2$ is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof;
wherein X is selected from the group consisting of O, S, and Se;
wherein G is a carbazole which may be optionally substituted;
wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and
wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

2. The compound of claim 1, wherein the compound has formula IV:

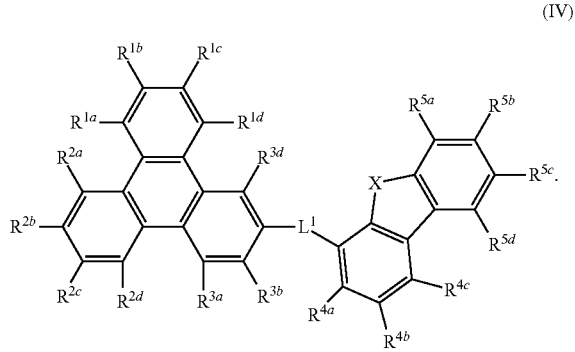

(IV)

3. The compound of claim 1, wherein the compound has formula V:

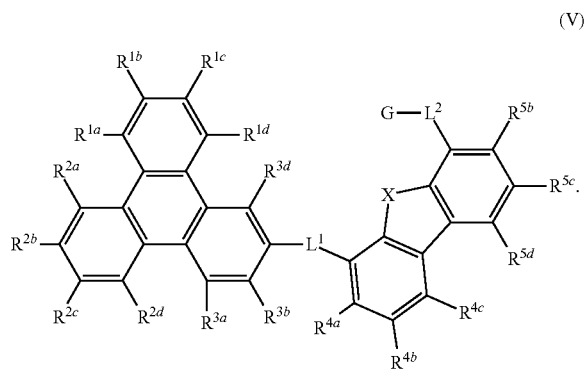

(V)

4. The compound of claim 1, wherein G is connected to $L^2$ at the nitrogen atom of the 9-position of carbazole.

5. The compound of claim 1, wherein G is connected to $L^2$ at a carbon atom at the 1-, 2-, 3-, or 4-position of carbazole.

6. The compound of claim 1, wherein one of $R^{4b}$, $R^{5a}$, or $R^{5c}$ is $L^2$-G.

7. The compound of claim 1, wherein $L^2$ is selected from the group consisting of a direct bond, a phenyl group, and a biphenyl group.

8. The compound of claim 1, wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, aryl, heteroaryl, and combinations thereof, wherein $R^{3a}$, $R^{3b}$, $R^{3c}$, and $R^{3d}$ that are not formula II are each independently selected from the group consisting of hydrogen, deuterium, aryl, heteroaryl, and combinations thereof, and wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, aryl, heteroaryl, and combinations thereof.

9. The compound of claim 1, wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, wherein $R^{3a}$, $R^{3b}$, $R^{3c}$, and $R^{3d}$ that are not formula II are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof, and wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, phenyl, biphenyl, terphenyl, tetraphenyl, pentaphenyl, pyridine, phenyl pyridine, pyridyl phenyl, triphenylene, carbazole, fluorene, dibenzofuran, dibenzothiophene, dibenzoselenophene, and combinations thereof.

10. The compound of claim 1, wherein $R^{1a}$, $R^{1b}$, $R^{1c}$, $R^{1d}$, $R^{2a}$, $R^{2b}$, $R^{2c}$, and $R^{2d}$ are hydrogen, wherein $R^{3a}$, $R^{3b}$, $R^{3c}$, and $R^{3d}$ that are not formula II are hydrogen, and wherein $R^{4a}$, $R^{4b}$, $R^{4c}$, $R^{5a}$, $R^{5b}$, $R^{5c}$, and $R^{5d}$ that are not formula III are hydrogen.

11. The compound of claim 1, wherein X is O.

12. The compound of claim 1, wherein X is S.

13. The compound of claim 1, wherein X is S, $L^2$ is a direct bond, and $R^{5a}$ is $L^2$-G.

14. The compound of claim 1, wherein X is S, $L^2$ is phenyl, and $R^{5a}$ is $L^2$-G.

15. The compound of claim 1, wherein the compound is selected from the group consisting of:

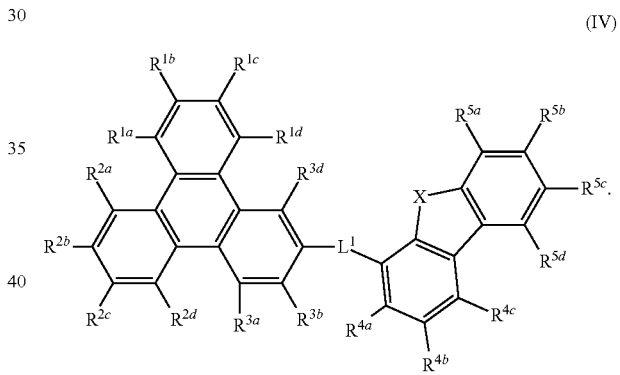

(IV)

16. A first device comprising an organic light emitting device, the organic light emitting device comprising:
an anode;
a cathode;
an organic layer, disposed between the anode and the cathode, wherein the organic layer comprises a compound having formula I:

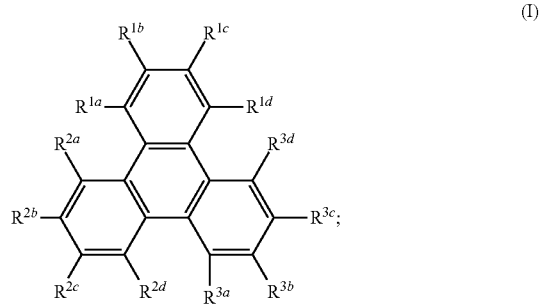

(I)

wherein at least one of $R^{3a}$, $R^{3b}$, $R^{3c}$, or $R^{3d}$ has formula II:

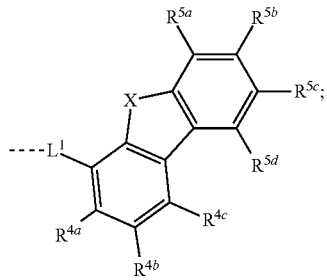
(II)

wherein at least one of $R^{4a}$, $R^{4b}$, $R^{4c}$, $R^{5a}$, $R^{5b}$, $R^{5c}$, or $R^{5d}$ has formula III:

-L²-G  (III);

wherein $L^1$ is a direct bond;
wherein $L^2$ is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, nitrile, and combinations thereof;
wherein X is selected from the group consisting of O, S, and Se;
wherein G is a carbazole which may be optionally substituted; and
wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and the organic layer is an emissive layer and the compound of formula I is a host.

17. The first device of claim 16, further comprising a blocking layer and the compound of formula I is a blocking material in the organic layer.

18. A formulation comprising a compound having formula I:

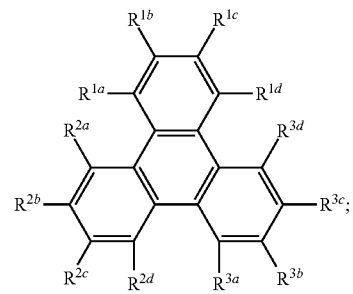
(I)

wherein at least one of $R^{3a}$, $R^{3b}$, $R^{3c}$, or $R^{3d}$ has formula II:

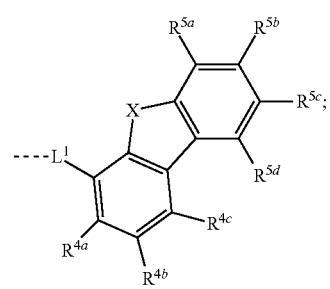
(II)

wherein at least one of $R^{4a}$, $R^{4b}$, $R^{4c}$, $R^{5a}$, $R^{5b}$, $R^{5c}$, or $R^{5d}$ has formula III:

-L²-G  (III);

wherein $L^1$ is a direct bond;
wherein $L^2$ is selected from the group consisting of a direct bond, an aryl group having from 6-30 carbon atoms, a heteroaryl group having from 3-30 carbon atoms, and combinations thereof; wherein the aryl group and the heteroaryl group are optionally further substituted with one or more groups selected from hydrogen, deuterium, alkyl, cycloalkyl, aralkyl, alkoxy, aryloxy, amino, silyl, aryl, heteroaryl, and combinations thereof;
wherein X is selected from the group consisting of O, S, and Se;
wherein G is a carbazole which may be optionally substituted;
wherein $R^{1a}$, $R^{1b}$, $R^{1c}$, $R^{1d}$, $R^{2a}$, $R^{2b}$, $R^{2c}$, and $R^{2d}$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;
wherein $R^{3a}$, $R^{3b}$, $R^{3c}$, and $R^{3d}$ that are not formula II are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and
wherein $R^{4a}$, $R^{4b}$, $R^{4c}$, $R^{5a}$, $R^{5b}$, $R^{5c}$, and $R^{5d}$ that are not formula III are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

\* \* \* \* \*

UNITED STATES PATENT AND TRADEMARK OFFICE
CERTIFICATE OF CORRECTION

PATENT NO. : 9,761,807 B2
APPLICATION NO. : 14/174396
DATED : September 12, 2017
INVENTOR(S) : Bin Ma et al.

It is certified that error appears in the above-identified patent and that said Letters Patent is hereby corrected as shown below:

In the Claims

In Claim 15, Column 156, Line 30-44, please delete:

"
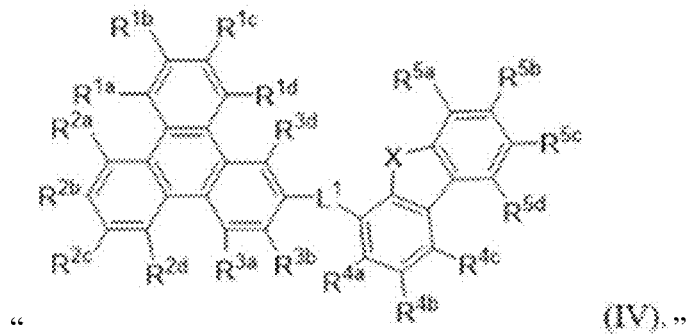
(IV),"

And insert

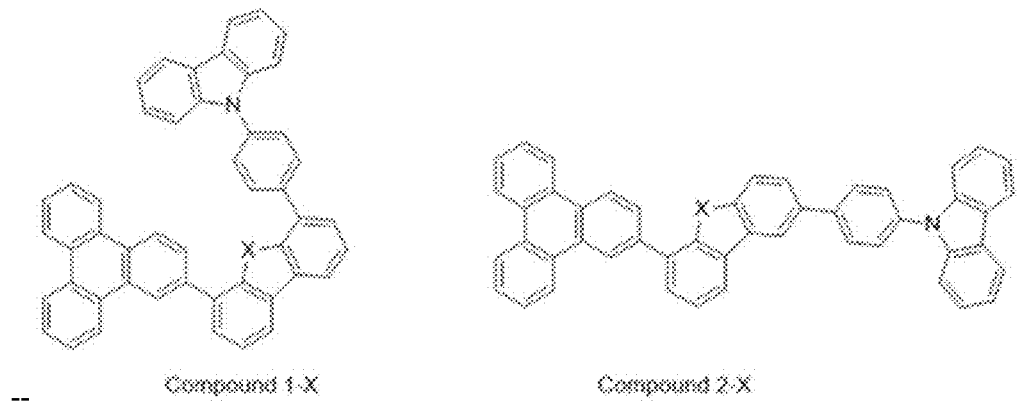

--

Signed and Sealed this
Twenty-sixth Day of June, 2018

Andrei Iancu
*Director of the United States Patent and Trademark Office*

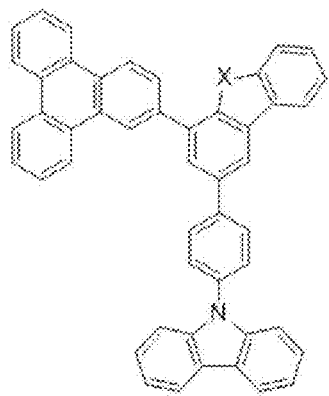
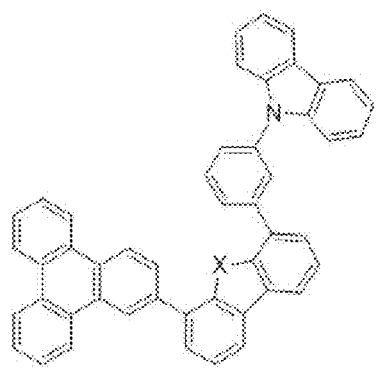
Compound 3-X
Compound 4-X
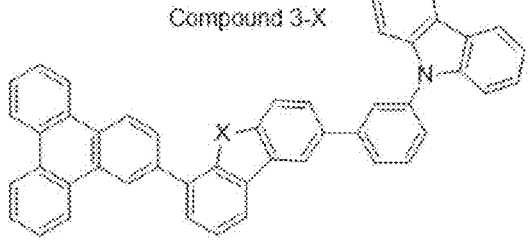
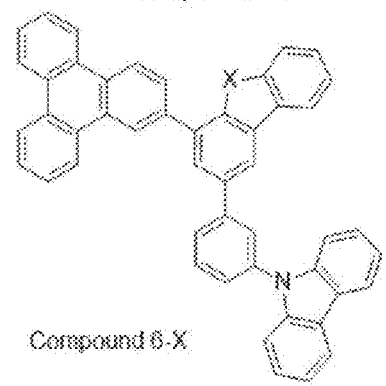
Compound 5-X
Compound 6-X
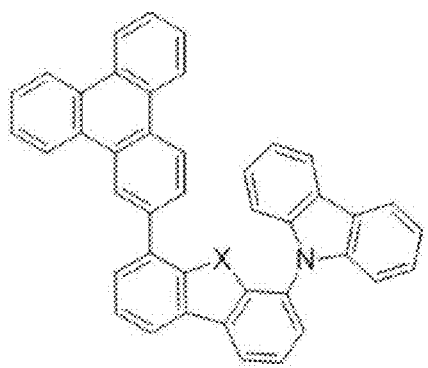
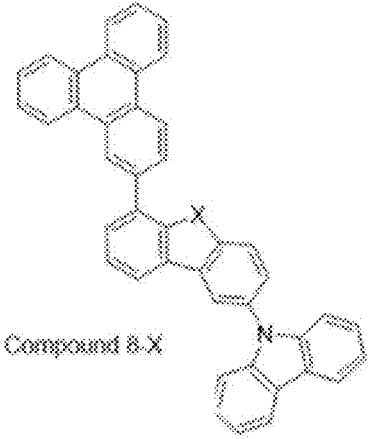
Compound 7-X
Compound 8-X
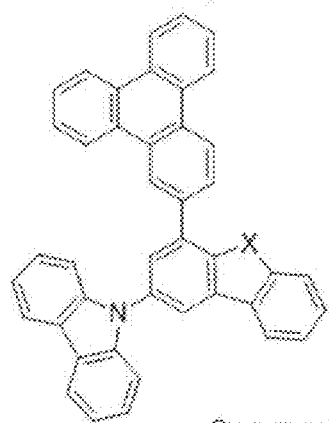
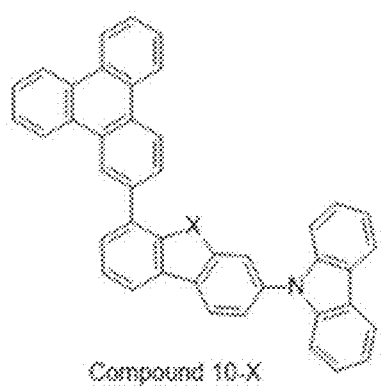
Compound 9-X
Compound 10-X CERTIFICATE OF CORRECTION (continued)
U.S. Pat. No. 9,761,807 B2

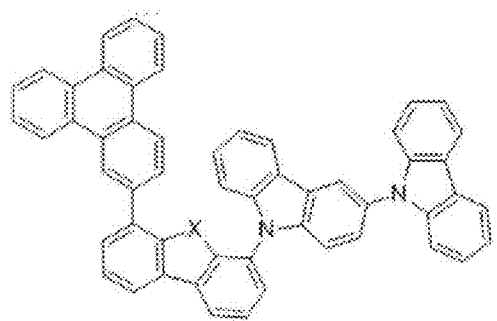
Compound 11-X

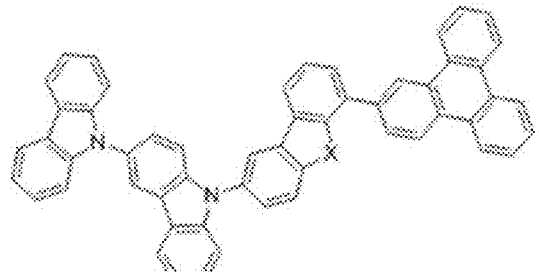
Compound 13-X

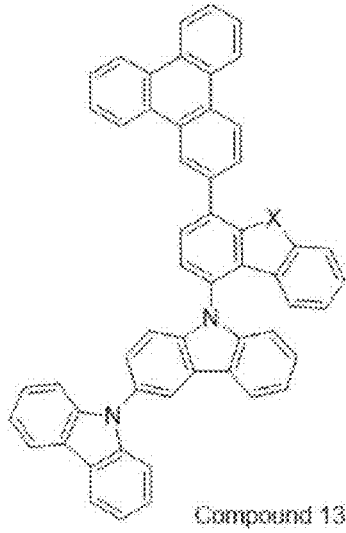
Compound 13-X

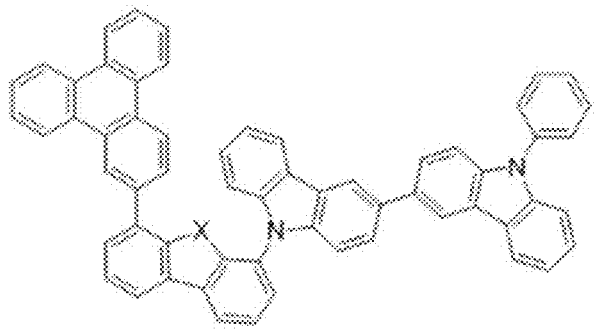
Compound 14-X

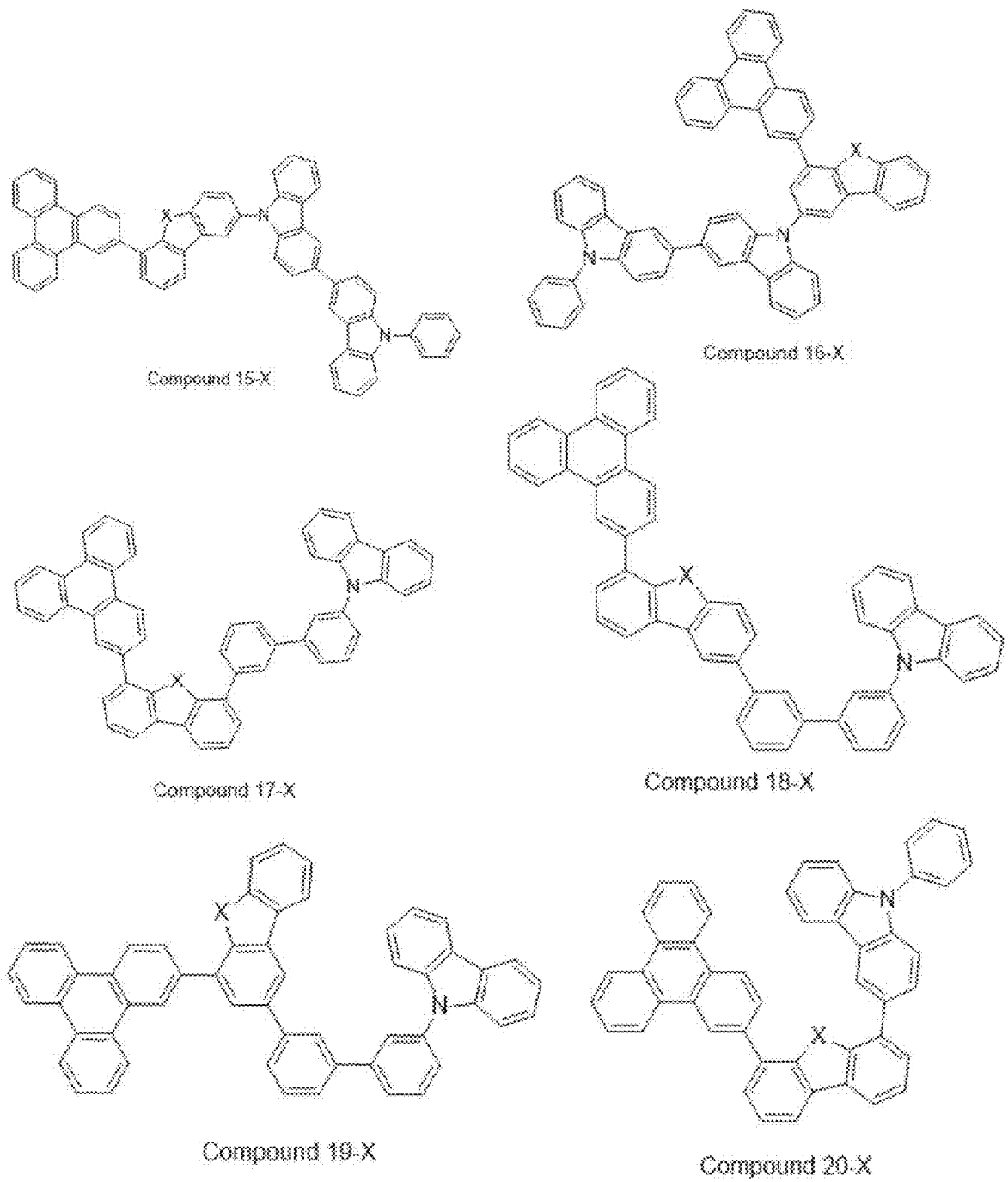
Compound 15-X
Compound 16-X
Compound 17-X
Compound 18-X
Compound 19-X
Compound 20-X

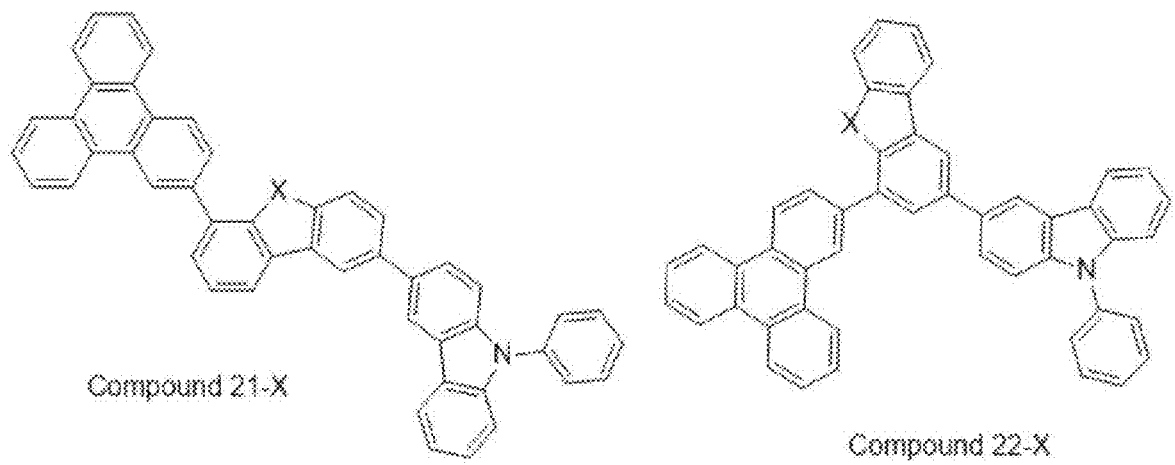
Compound 21-X
Compound 22-X
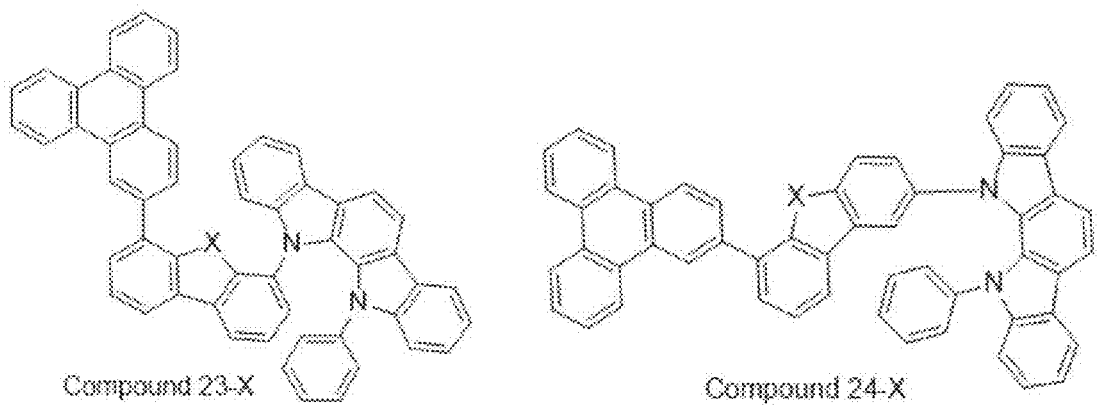
Compound 23-X
Compound 24-X
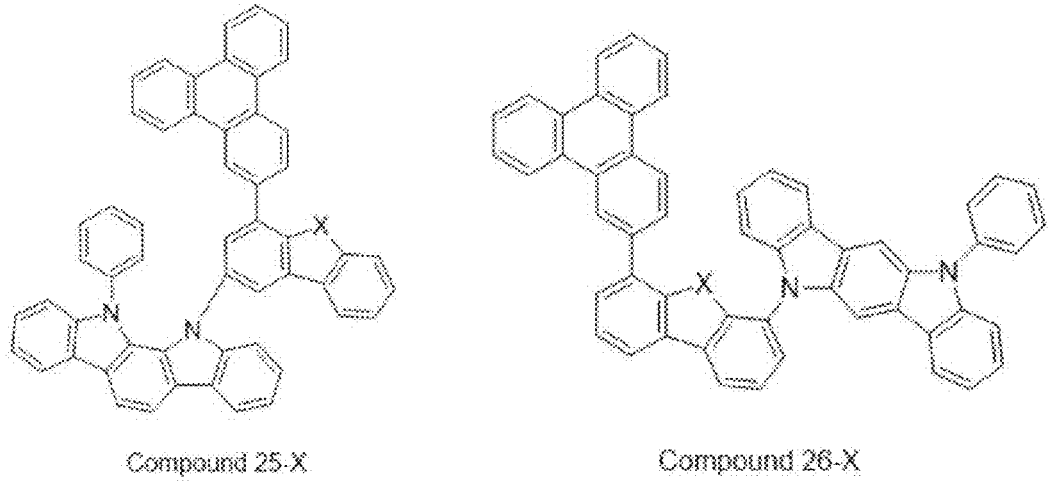
Compound 25-X
Compound 26-X

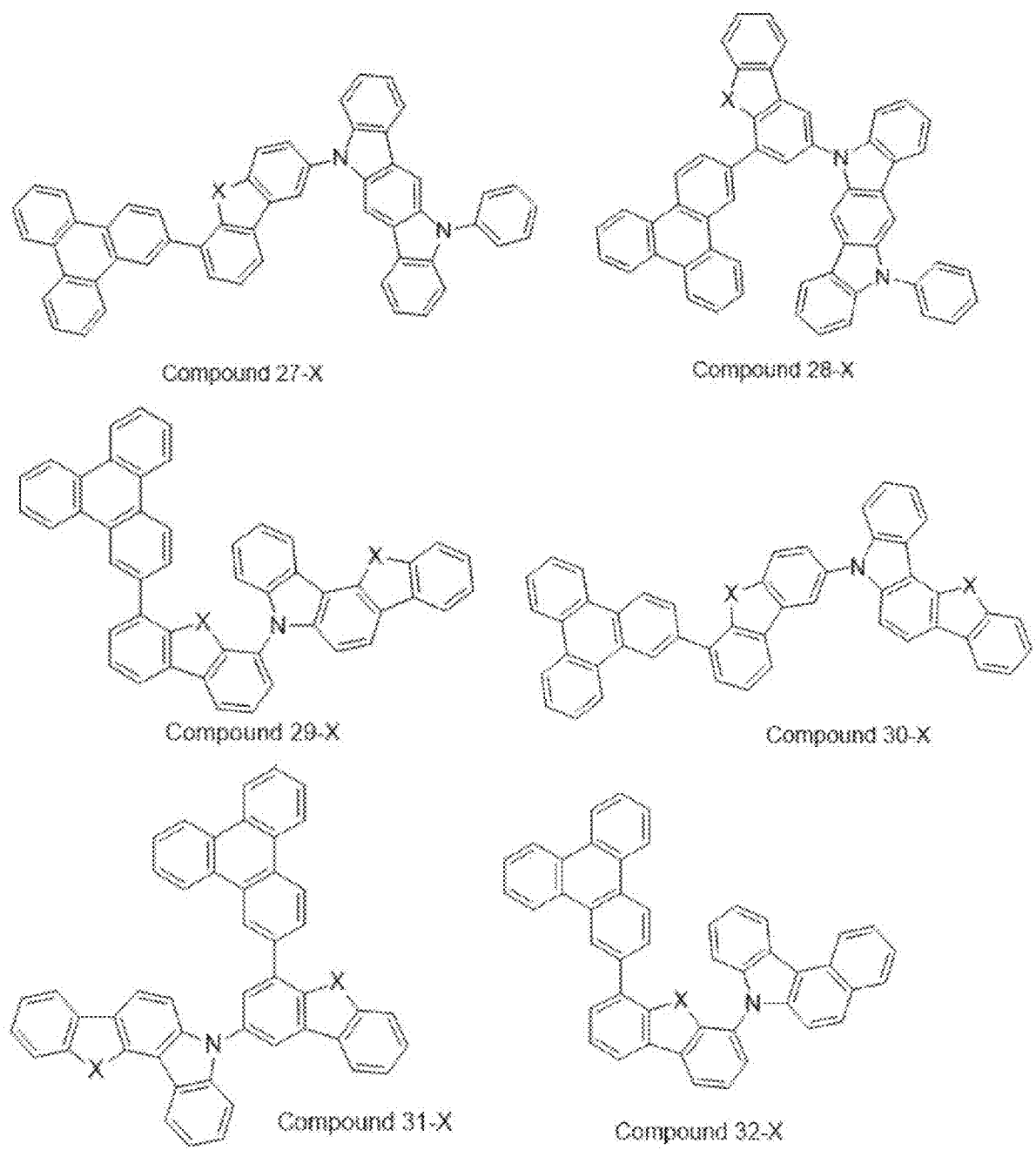
Compound 27-X
Compound 28-X
Compound 29-X
Compound 30-X
Compound 31-X
Compound 32-X

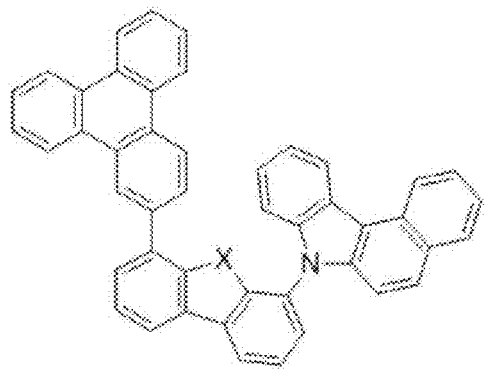
Compound 33-X
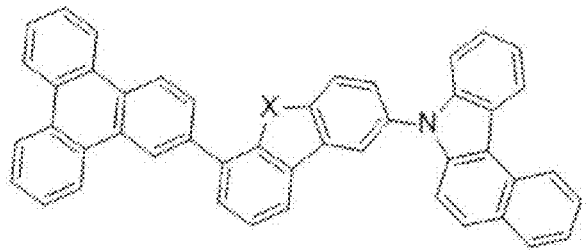
Compound 34-X
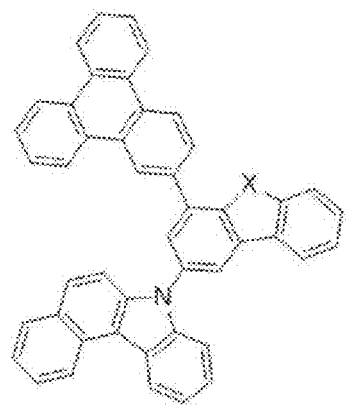
Compound 35-X
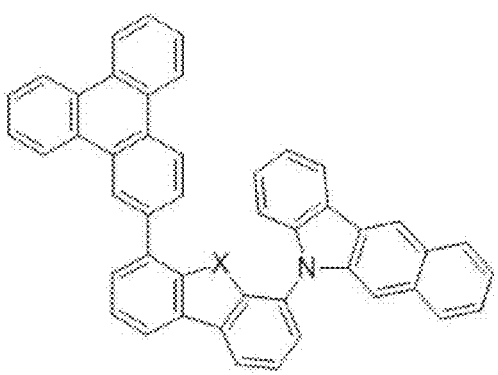
Compound 36-X
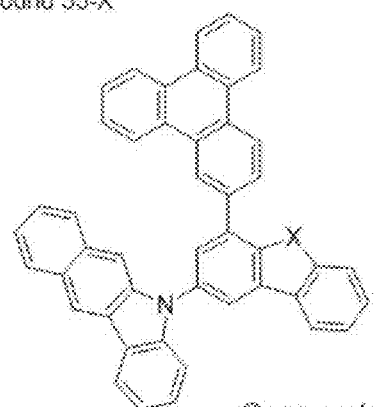
Compound 37-X
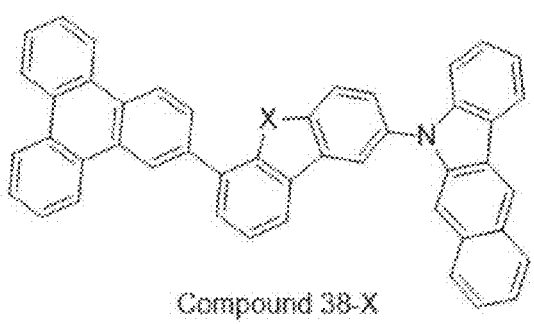
Compound 38-X

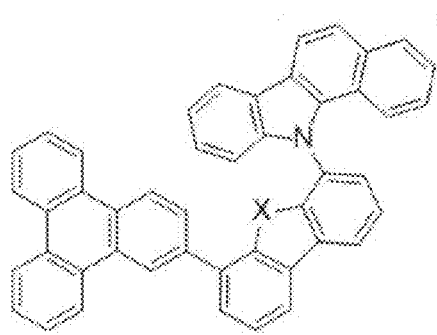
Compound 39-X
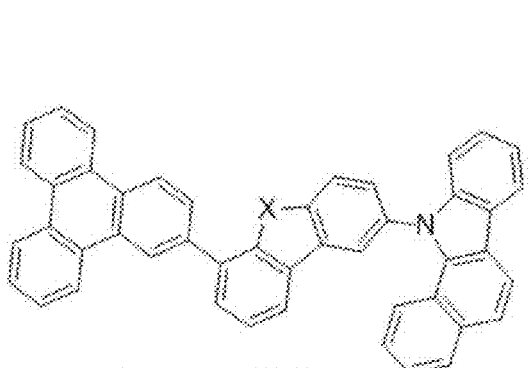
Compound 40-X
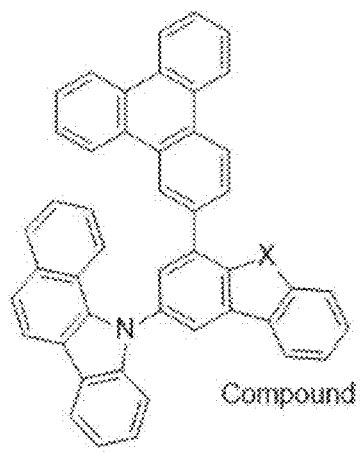
Compound 41-X
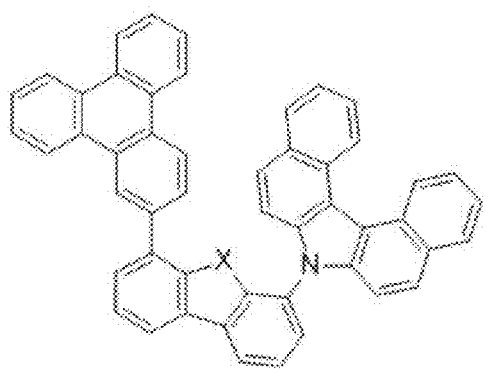
Compound 42-X
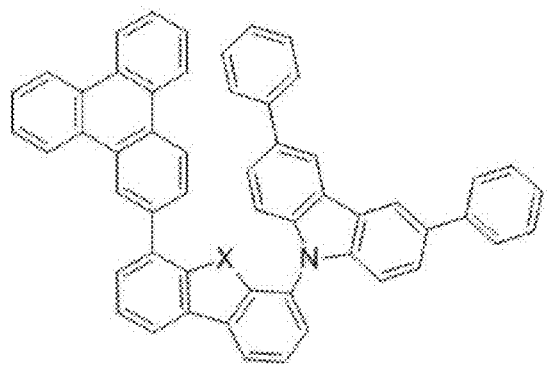
Compound 46-X